United States Patent
Wendt et al.

(10) Patent No.: US 7,115,596 B2
(45) Date of Patent: Oct. 3, 2006

(54) THIAZOLE COMPOUNDS AS INTEGRIN RECEPTOR ANTAGONISTS DERIVATIVES

(75) Inventors: John A. Wendt, South Lyon, MI (US); Heather Stenmark, Chicago, IL (US); Hongwei Wu, Buffalo Grove, IL (US); Yaping Wang, Acton, MA (US); Barbara B. Chen, Northbrook, IL (US); Thomas D. Penning, Elmhurst, IL (US); Victoria L. Downs, Pinckney, MI (US); Mark L. Boys, Brighton, MI (US); Mark Russell, Gurnee, IL (US); Dale P. Spangler, San Diego, CA (US)

(73) Assignee: Pharmacia Corporation, St. Louis, MO (US)

( * ) Notice: Subject to any disclaimer, the term of this patent is extended or adjusted under 35 U.S.C. 154(b) by 293 days.

(21) Appl. No.: 10/741,056

(22) Filed: Dec. 19, 2003

(65) Prior Publication Data

US 2005/0004189 A1    Jan. 6, 2005

Related U.S. Application Data

(60) Provisional application No. 60/435,030, filed on Dec. 20, 2002.

(51) Int. Cl.
```
A61K 31/55     (2006.01)
A61K 31/5025   (2006.01)
A61K 31/44     (2006.01)
A61K 31/425    (2006.01)
A61K 31/36     (2006.01)
C07D 401/00    (2006.01)
C07D 417/00    (2006.01)
C07D 413/00    (2006.01)
C07D 471/02    (2006.01)
C07D 207/00    (2006.01)
C07D 317/46    (2006.01)
```

(52) U.S. Cl. .......... 514/217.04; 514/249; 514/303; 514/365; 514/465; 540/597; 544/60; 544/124; 544/350; 546/118; 546/122; 546/269.7; 546/290; 548/181; 548/400; 549/435

(58) Field of Classification Search ........ 514/365, 514/217.04, 249, 303, 465; 548/146, 181, 548/400; 540/597; 544/60, 124, 350; 546/118, 546/122, 269.7, 290; 549/435
See application file for complete search history.

(56) References Cited

U.S. PATENT DOCUMENTS

| | | |
|---|---|---|
| 5,700,823 A | 12/1997 | Hirth et al. |
| 5,773,646 A | 6/1998 | Chandrakumar et al. |
| 5,849,736 A | 12/1998 | Wityak et al. |
| 5,852,210 A | 12/1998 | Chen et al. |

2003/0073688 A1   4/2003   Vianello et al.

FOREIGN PATENT DOCUMENTS

| | | |
|---|---|---|
| GB | 2327672 A | 2/1999 |
| WO | WO 92/07468 A1 | 5/1992 |
| WO | WO 94/08577 A1 | 4/1994 |
| WO | WO 97/44333 A1 | 11/1997 |
| WO | WO 98/18461 | 5/1998 |
| WO | WO 99/26945 A1 | 6/1999 |
| WO | WO 99/30709 A1 | 6/1999 |
| WO | WO 99/30713 A1 | 6/1999 |
| WO | WO 00/07544 A2 | 2/2000 |
| WO | WO 00/33838 A1 | 6/2000 |
| WO | WO 00/72801 A2 | 12/2000 |
| WO | WO 01/24797 A1 | 4/2001 |
| WO | WO 01/96334 A2 | 12/2001 |
| WO | WO 02/081497 A2 | 10/2002 |
| WO | WO 2002088118 A1 | 11/2002 |

OTHER PUBLICATIONS

Tavecchia et al. "Revised Structure of the Antibiotic GE 2270A" The Journal of Antibiotics, 1994, 1564-1567.*

Bal et al., "Oxidation of α,β-Unsaturated Aldehydes", Tetrahedron, 1981, 37: 2091-2096.

Bedford et al., "Nonquaternary Cholinesterase Reactivators. 3. 3(5)-Substituted 1,2,4-Oxadiazol-5(3)-aldoximes and 1,2,4-Oxidiazole-5(3)-thiocarbohydroximates as Reactivators of Organophosphonate-Inhibited Eel and Human Acetylcholinesterase in Vitro", Journal of Medicinal Chemistry, 1986, 29: 2174-2183.

Berge et al., "Pharmaceutical Salts", Journal of Pharmaceutical Sciences, 1977, 66(1): 1-19.

(Continued)

*Primary Examiner*—Kamal A. Saeed
*Assistant Examiner*—Joseph R. Kosack
(74) *Attorney, Agent, or Firm*—Matthew J. Pugmire; Bryan C. Zielinski

(57) ABSTRACT

The present invention relates to a class of compounds represented by the Formula I

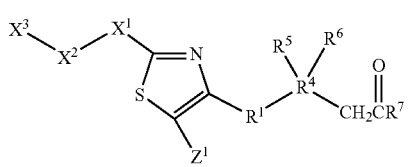

or a pharmaceutically acceptable salt thereof, pharmaceutical compositions comprising compounds of the Formula I, and methods of selectively inhibiting or antagonizing the $\alpha_v\beta_3$ and/or the $\alpha_v\beta_5$ integrin without significantly inhibiting the $\alpha_v\beta_6$ integrin.

6 Claims, No Drawings

OTHER PUBLICATIONS

Brown et al., "Lignanes. 18. Synthése Totale et Confirmation de la Structure de l'Acid Mégacérotonique", Tetrahedron, 1995, 51: 13061-13072.

Charo et al., "Inhibition of Fibrinogen Binding to GP IIb/IIIa by a GP IIIa Peptide", Journal of Biological Chemistry, 1991, 266(3): 1415-1421.

Cornforth et al., "A Synthesis of Acylamidomalondialdehydes" Journal of the Chemical Society, 1949, 1550.

Diederich et al., "A Water-Soluble Tetraoxa[7.1.7.1] paracyclophane: Synthesis and Host-Guest Interactions with Alicyclic and Cationic Aromatic Guest Molecules in Aqueour Solution", Chemische Berichte, 1985, 118: 3817-3829.

Ellison et al., "Cyclopentenone Synthesis Via Aldol Condensation. Synthesis of a Key Prostaglandin Intermediate", Tetrahedron Letters, 1975, 8: 499-502.

Hofman et al., "Studies Directed Towards the Total Synthesis of (+)-Himbacine", Journal of Synthetic Organic Chemistry, 1998, 479-489.

Huang et al., "Expression of the Human Integrin β6 Subunit in Alveolar Type II Cells and Bronchiolar Epithelial Cells Reverses Lung Inflammation in β6 Knockout Mice", American Journal of Respiratory Cell and Molecular Biology, 1998, 19(4): 636-42.

Kirk et al., "Syntheses and Adrenergic Agonist Properties of Ring-Fluorinated Isoproterenols", Journal Medicinal Chemistry, 1982, 25: 680-684.

Legters et al., "A Convenient Synthesis of Aziridine-2-carboxylic Esters", Journal of the Royal Netherlands Chemical Society, 1992, 111(1): 1-15.

Mcelvain et al., "Piperidine Derivatives. XXX. 1,4-Dialkyl-4-arylpiperidines", Journal of the American Chemical Society, 1958, 80: 3915-3923.

Muri et al., "Synthesis of New Benzylic Ethers of Oximes Derived from 1-Phenyl-Pyrazole Compounds", Synthetic Communications, 1998, 28(7): 1299-1321.

Niiya et al., "Increased Surface Expression of the Membrane Glycoprotein IIb/IIIa Complex Induced by Platelet Activation: Relationships to the Binding of Fibrinogen and Platelet Aggregation", Blood, 1987, 70: 475-483.

Pytela et al., "Arginine-Glycine-Aspartic Acid Adhesion Receptors", Methods in Enzymology, 1987, 144: 475-489.

Sundberg et al., "Improved Procedures for Preparation of 4-Hydroxy- and 2-Amino-4-Methoxy-2-Aminopyridines", Organic Preparations and Procedures Int., 1997, 29(1); 117-122.

Tokoroyama et al., "Folding Strain Stereocontrol in Cyclohexane Ring Formation by Means of an Intramolecular Ester Enolate Alkylation Reaction" Canadian Journal of Chemistry, 1996, 74(12): 2487-2502.

Vogel, "Physical Properties and Chemical Constitution. Part II Esters of ββ-Substituted Glutaric Acids", Journal of the Chemical Society, 1934, 1758-1765.

Yatohgo et al., "Novel Purification of Vitronectin from Human Plasma by Heparin Affinity chromatography", Cell Structure and Function, 1988, 13: 281-292.

Zelle et al., "A Simple, High-Yielding Method for the Methylenation of Catechols", Tetrahedron Letters, 1991, 32: 2461-2464.

Zucker, "Platelet Aggregation Measured by the Photometric Method", Methods in Enzymology, 1989, 169: 117-133.

International Search Report for PCT/US03/40629, dated May 7, 2004.

Plouvier et al., "Antitumor Combilexin. A Thiazole-Containing Analogue of Netropsin Linked to an Acridine Chromophore", Bioconjugate Chem, 1994, 5(5), 475-481.

International Search Report for PCT/US03/40898, dated May 7, 2004.

* cited by examiner

THIAZOLE COMPOUNDS AS INTEGRIN RECEPTOR ANTAGONISTS DERIVATIVES

CROSS-REFERENCE TO RELATED APPLICATION

This application claims priority from Provisional Application Ser. No. 60/435,030 filed on Dec. 20, 2002, which is hereby incorporated by reference in its entirety.

FIELD OF INVENTION

The present invention relates to pharmaceutical agents (compounds) that are $\alpha_v\beta_3$ and/or $\alpha_v\beta_5$ integrin antagonists and as such are useful in pharmaceutical compositions and in methods for treating conditions mediated by $\alpha_v\beta_3$ and/or $\alpha_v\beta_5$ integrins.

BACKGROUND OF THE INVENTION

The integrin $\alpha_v\beta_3$ (also known as vitronectin receptor), is a member of the integrin family of heterodimeric transmembrane glycoprotein complexes that mediate cellular adhesion events and signal transduction processes. Integrin $\alpha_v\beta_3$ is expressed in number of cell types and has been shown to mediate several biologically relevant processes, including adhesion of osteoclasts to the bone matrix, vascular smooth muscle cell migration and angiogenesis.

The integrin $\alpha_v\beta_3$ has been shown to play a role in various conditions or disease states including tumor metastasis, solid tumor growth (neoplasia), osteoporosis, Paget's disease, humoral hypercalcemia of malignancy, osteopenia, angiogenesis, including tumor angiogenesis, retinopathy including macular degeneration, arthritis, including rheumatoid arthritis, periodontal disease, psoriasis and smooth muscle cell migration (e.g. restenosis artherosclerosis). The compounds of the present invention are $\alpha_v\beta_3$ antagonists and can be used, alone or in combination with other therapeutic agents, in the treatment or modulation of various conditions or disease states described above. Additionally, it has been found that such agents would be useful as antivirals, antifungals and antimicrobials.

The integrin $\alpha_v\beta_5$ plays a role in neovascularization. Therefore the compounds of this invention which act as antagonists of the $\alpha_v\beta_5$ integrin will inhibit neovascularization and will be useful for treating and preventing angiogenesis metastasis, tumor growth, macular degeneration and diabetic retinopathy.

Antagonists of $\alpha_v\beta_3$ or dual $\alpha_v\beta_3/\alpha_v\beta_5$ antagonists can be useful therapeutic agents for treating many pathological conditions, including the treatment or prevention of osteopenia or osteoporosis, or other bone disorders, such as Paget's disease or humoral hypercalcemia of malignancy; neointimal hyperplasia, which can cause artherosclerosis or restenosis after vascular procedures; periodontal disease; treatment and prevention of viral infections or other pathogens; the treatment of neoplasia; pathological angiogenesis or neovascularization such as tumor metastasis, diabetic retinopathy, macular degeneration, rheumatoid arthritis, or osteoarthritis.

Compounds that antagonize the $\alpha_v\beta_5$ and/or the $\alpha_v\beta_3$ receptor have been reprinted in the literature. For example, WO 01/96334 provides heteroarylalkanoic acid compounds useful as $\alpha_v\beta_3$ and/or $\alpha_v\beta_5$ inhibitors.

SUMMARY OF THE INVENTION

In general, the present invention is directed to selective integrin receptor antagonist compounds or a pharmaceutically acceptable salt, isomer, tautomer or prodrug thereof corresponding to Formula (I):

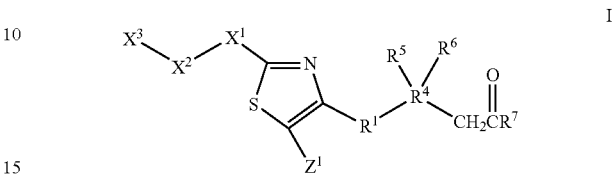

or a pharmaceutically acceptable salt thereof;
wherein:

$R^1$ is selected from the group consisting of —CH($R^2$)—, —N($R^3$)—, —O—, —S—, —S(O)$_2$—, —NHS(O)$_2$—, —S(O)$_2$NH— and —C(O)—;

$R^2$ is selected from the group consisting of hydrogen, hydroxy, and optionally substituted hydrocarbyl or alkoxy, wherein the optional substituents are selected from the group consisting of alkyl, halogen, hydroxy, alkoxy, amino, alkylamino, dialkylamino, cyano, acyl, —S—, —SO—, —SO$_2$—, sulfonamido, aryl, and heteroaryl, or $R^2$ in combination with $R^7$ and forms a lactone;

$R^3$ is selected from the group consisting of hydrogen and optionally substituted hydrocarbyl, heteroaryl, or acyl wherein the optional substituents are selected from the group consisting of alkyl, halogen, hydroxy, alkoxy, amino, alkylamino, dialkylamino, cyano, acyl, —S—, —SO—, —SO$_2$—, sulfonamido, aryl, and heteroaryl;

$R^4$ is carbon or nitrogen;

$R^5$ is selected from the group consisting of hydrogen, halo, and optionally substituted hydrocarbyl or heteroaryl, wherein the optional substituents are selected from the group consisting of alkyl, halogen, hydroxy, alkoxy, alkoxyalkyl, amino, alkylamino, dialkylamino, cyano, acyl, —S—, —SO—, —SO$_2$—, sulfonamido, heteroaryl, and optionally substituted aryl, wherein the optional substituent is halo, or $R^5$ together with $R^4$ and $R^6$ forms a heterocycle or aryl ring;

$R^6$ is an electron pair when $R^4$ is nitrogen, or $R^6$ is heteroaryl when $R^4$ is carbon, or $R^6$ is hydrogen, halo, or optionally substituted hydrocarbyl, wherein the optional substituents are selected from the group consisting of alkyl, halogen, hydroxy, alkoxy, amino, alkylamino, dialkylamino, cyano, acyl, —S—, —SO—, —SO$_2$—, sulfonamido, aryl, and heteroaryl, or $R^6$ together with $R^4$ and $R^5$ forms a heterocycle or aryl ring;

$R^7$ is selected from the group consisting of —OR$^8$, —SR$^8$, and —NR$^8$R$^9$;

$R^8$ is selected from the group consisting of hydrogen and optionally substituted hydrocarbyl, wherein the optional substituents are selected from the group consisting of alkyl, halogen, hydroxy, alkoxy, amino, alkylamino, dialkylamino, cyano, acyl, —S—, —SO—, —SO$_2$—, sulfonamido, aryl, and heteroaryl;

$R^9$ is selected from the group consisting of hydrogen, hydroxy, and optionally substituted hydrocarbyl or alkoxy, wherein the optional substituents are selected from the group consisting of alkyl, halogen, hydroxy, alkoxy, amino, alkylamino, dialkylamino, cyano, acyl, —S—, —SO—, —SO$_2$—, sulfonamido, aryl, and heteroaryl;

$X^1$ is selected from the group consisting of —O—, —CH$_2$—, —CH$_2$O—, —NH—, —C(O)—, —S—, —S(O)—, —CH(OH)—, —S(O)$_2$—, alkenyl, and alkynyl;

$X^2$ is a linker comprising a chain of 1 to 5 atoms, optionally substituted, selected from the group consisting of C, O, S and N;

$X^3$ is heterocyclic; and $Z^1$ is selected from the group consisting of hydrogen, hydroxy, cyano, and optionally substituted hydrocarbyl or heteroaryl, wherein the optional substituents are selected from the group consisting of alkyl, halogen, hydroxy, alkoxy, amino, alkylamino, dialkylamino, cyano, acyl, —S—, —SO—, —SO$_2$—, sulfonamido, aryl, and heteroaryl.

The present invention is further directed to a process of treating conditions mediated by $\alpha_v\beta_3$ and/or $\alpha_v\beta_5$ integrins in a mammal. The process comprises administering to a mammal in need thereof a therapeutically effective dose of a compound of Formula I.

Other aspects of the invention will be in part apparent and in part pointed out hereinafter.

Definitions

The term "acyl" denotes a radical provided by the residue after removal of hydroxyl from an organic acid. Examples of such acyl radicals include alkanoyl and aroyl radicals. Examples of such lower alkanoyl radicals include formyl, acetyl, propionyl, butyryl, isobutyryl, valeryl, isovaleryl, pivaloyl, hexanoyl, and trifluoroacetyl.

The term "alkyl" embraces linear, cyclic or branched hydrocarbon radicals having one to about twenty carbon atoms or, preferably, one to about twelve carbon atoms. More preferred alkyl radicals are "lower alkyl" radicals having one to about ten carbon atoms. In another embodiment, the alkyl radicals are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like.

The term "cycloalkyl" embraces saturated carbocyclic radicals having three to twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl.

The term "haloalkyl" embraces radicals wherein any one or more of the alkyl carbon atoms is substituted with halo as defined below. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio.

The term "alkenyl" embraces linear or branched hydrocarbon radicals having at least one carbon-carbon double bond of two to about twenty carbon atoms or, preferably, two to about twelve carbon atoms. More preferred alkyl radicals are "lower alkenyl" radicals having two to about ten carbon atoms. In another embodiment, the alkenyl radicals are lower alkenyl radicals having two to about six carbon atoms. Examples of alkenyl radicals include ethenyl, propenyl, allyl, propenyl, butenyl and 4-methylbutenyl. The terms "alkenyl" and "lower alkenyl" embrace radicals having "cis" and "trans" orientations, or alternatively, "E" and "Z" orientations.

The term "alkynyl" denotes linear or branched radicals having two to about twenty carbon atoms or, preferably, two to about twelve carbon atoms. More preferred alkynyl radicals are "lower alkynyl" radicals having two to about ten carbon atoms. In another embodiment, the alkynyl radicals are "lower alkynyl" radicals having two to six carbon atoms. Examples of such radicals include propargyl, butynyl, and the like.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The "substituted aryl" moieties described herein are aryl moieties which are substituted with at least one atom, including moieties in which a carbon chain atom is substituted with a hetero atom such as nitrogen, oxygen, silicon, phosphorous, boron, sulfur, or a halogen atom. These substituents include halogen, heteroaryl, hydrocarbyloxy such as alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "aralkyl" embraces aryl-substituted alkyl radicals such as benzyl, diphenylmethyl, triphenylmethyl, phenylethyl, and diphenylethyl. The "substituted aryl" moieties described herein are aryl moieties which are substituted with at least one atom, including moieties in which a carbon chain atom is substituted with a hetero atom such as nitrogen, oxygen, silicon, phosphorous, boron, sulfur, or a halogen atom. These substituents include halogen, heteroaryl, hydrocarbyloxy such as alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "amino" is used herein to typically refer to the group —NT$^2$T$^3$, where each of T$^2$ and T$^3$ is independently selected from the group consisting of hydrogen, hydrocarbyl, substituted hydrocarbyl, aryl, or heteroaryl. In another embodiment, T$^2$ and T$^3$ form a mono or polycyclic amino ring. The term "cyclicamino" embraces saturated heterocyclic radicals having three to eight atoms, at least one of which is nitrogen, but may also contain other heteroatoms such as oxygen, silicon, phosphorous, boron, sulfur, or a halogen.

The term "aminoalkyl" embraces alkyl radicals substituted with one or more amino radicals. More preferred are "lower aminoalkyl" radicals. Aminoalkyl refers to a radical of the formula:

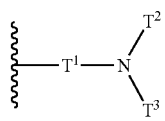

wherein T¹ is alkyl, and T² and T³ are as defined in definition of amino.

The term "alkylamino" denotes amino groups that have been substituted with one or two alkyl radicals. Preferred is "lower N-alkylamino" radicals having alkyl portions having 1 to 6 carbon atoms. Alkylamino refers to a radical of the formula:

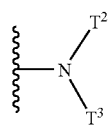

wherein T² and T³ are as defined in definition of amino. Suitable lower alkylamino may be mono or dialkylamino such as N-methylamino, N-ethylamino, or N,N-dimethylamino.

The term "arylamino" denotes amino groups, which have been substituted with one or two aryl radicals, such as N,N-diphenylamino. The "arylamino" radicals may be further substituted on the aryl ring portion of the radical.

The term "carbonyl", whether used alone or with other terms, such as "alkoxycarbonyl", denotes —(C=O)—.

The terms "carboxy" or "carboxyl", whether used alone or with other terms, such as "carboxyalkyl", denotes —CO₂H.

The term "carboxyalkyl" embraces alkyl radicals substituted with a carboxy radical. Examples of carboxyalkyl radicals include carboxymethyl, carboxyethyl and carboxypropyl.

The term "halo" means halogens such as fluorine, chlorine, bromine or iodine.

The term "heteroaryl" embraces unsaturated heterocyclyl radicals. Examples of unsaturated heterocyclyl radicals, also termed "heteroaryl" radicals include unsaturated 3 to 8 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 8-membered heteromonocyclic group containing an oxygen atom, for example, pyranyl, furyl, etc.; unsaturated 3 to 8-membered heteromonocyclic group containing a sulfur atom, for example, thienyl, etc.; unsaturated 3- to 8-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 8-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like. The term also embraces radicals where heterocyclyl radicals are fused with aryl radicals or a non-aromatic cyclic system. Examples of such fused bicyclic radicals include benzofuran, benzothiophene, and the like.

The "substituted heteroaryl" moieties described herein are heteroaryl moieties which are substituted with at least one atom, including moieties in which a carbon chain atom is substituted with a hetero atom such as nitrogen, oxygen, silicon, phosphorous, boron, sulfur, or a halogen atom. These substituents include halogen, heteroaryl, hydrocarbyloxy such as alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "heteroatom" shall mean atoms other than carbon and hydrogen.

The term "heterocyclo" and "heterocyclic" embraces optionally substituted saturated, partially unsaturated and unsaturated heteroatom-containing ring-shaped radicals containing 3 to 10 members, including at least 1 carbon atom and up to 9 additional members independently selected from carbon, nitrogen, sulfur and oxygen. This includes, for example, the following structures:

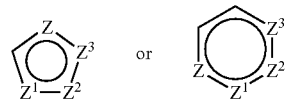

wherein Z, Z¹, Z² or Z³ is C, S, O, or N, with the proviso that one of Z, Z¹, Z² or Z³ is other than carbon, but is not O or S when attached to another Z atom by a double bond or when attached to another O or S atom. Furthermore, optional substituents are understood to be attached to Z, Z¹, Z² or Z³ only when each is C.

Examples of saturated heterocyclyl radicals include saturated 3 to 8-membered heteromonocylic group containing 1 to 4 nitrogen atoms (e.g. pyrrolidinyl, imidazolidinyl, piperidino, piperazinyl, etc.); saturated 3 to 8-membered heteromonocyclic group containing 1 to 2 oxygen atoms and 1 to 3 nitrogen atoms (e.g. morpholinyl, etc.); saturated 3 to 8-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole.

The "substituted heterocyclo" moieties described herein are heterocyclo moieties which are substituted with at least one atom, including moieties in which a carbon chain atom is substituted with a hetero atom such as nitrogen, oxygen, silicon, phosphorous, boron, sulfur, or a halogen atom. These substituents include halogen, heterocyclo, hydrocarbyloxy such as alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "heterocyclylalkyl" embraces saturated and partially unsaturated heterocyclyl-substituted alkyl radicals, such as pyrrolidinylmethyl, and heteroaryl-substituted alkyl radicals, such as pyridylmethyl, quinolylmethyl, thienylmethyl, furylethyl, and quinolylethyl. The heteroaryl in said heteroaralkyl is optionally substituted with halo, alkyl, alkoxy, haloalkyl and haloalkoxy.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom, including moieties in which a carbon chain atom is substituted with a hetero atom such as nitrogen, oxygen, silicon, phosphorous, boron, sulfur, or a halogen atom. These substituents include halogen, heterocyclo, hydrocarbyloxy such as alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term substituted hydrocarbyloxy as used herein alone or as part of another group, denotes a substituted hydrocarbyl group as described above bonded through an oxygen linkage (—O—).

The term "hydroxyalkyl" embraces linear or branched alkyl radicals having one to about ten carbon atoms any one of which are optionally substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl.

The term "lactone" refers to an anhydro cyclic ester produced by intramolecular condensation of a hydroxy acid with the elimination of water.

The term "sulfonamide" or "sulfonamido" refers to a radical of the formula:

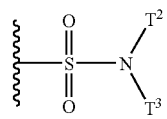

wherein T² and T³ are as defined in definition of amino.

The term "sulfonyl", whether used alone or linked to other terms such as alkylsulfonyl, denotes respectively divalent radicals —SO₂—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals are optionally substituted with one or more halo atoms, such as fluoro, chloro or bromo, to provide haloalkylsulfonyl radicals.

The term "trifluoroalkyl" refers to an alkyl radical as defined above substituted with three halo radicals as defined above.

The term "methylenedioxy" refers to the radical:

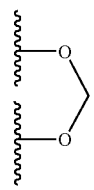

The term "ethylenedioxy" refers to the radical:

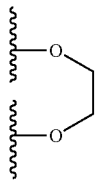

The term "composition" as used herein means a product that results from the mixing or combining of more than one element or ingredient.

The term "pharmaceutically acceptable carrier", as used herein means a pharmaceutically acceptable material, composition or vehicle, such as a liquid or solid filler, diluent, excipient, solvent or encapsulating material, involved in carrying or transporting a chemical agent.

The term "pharmaceutically acceptable salt" refers to a salt prepared by contacting a compound of Formulas I–IV with an acid whose anion is generally considered suitable for human consumption. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid. Representative salts include the following: benzenesulfonate, hydrobromide and hydrochloride. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. All of the pharmacologically acceptable salts may be prepared by conventional means. (See Berge et al., *J Pharm. Sci.*, 66(1), 1–19 (1977) for additional examples of pharmaceutically acceptable salts.)

The term "therapeutically effective amount" shall mean that amount of drug or pharmaceutical agent that will elicit the biological or medical response of a tissue, system or animal that is being sought by a researcher or clinician.

As used herein, the term "treatment" is meant the medical management of a subject, e.g. an animal or human, with the intent that a prevention, cure, stabilization, or amelioration of the symptoms or condition will result. This term includes active treatment, that is, treatment directed specifically toward improvement of the disorder; palliative treatment, that is, treatment designed for the relief of symptoms rather than the curing of the disorder; preventive treatment, that is, treatment directed to prevention of disorder; and supportive treatment, that is, treatment employed to supplement another specific therapy directed toward the improvement of the disorder. The term "treatment" also includes symptomatic treatment, that is, treatment directed toward constitutional symptoms of the disorder. "Treating" a condition with the compounds of the invention involves administering such a compound, alone or in combination and by any appropriate means, to an animal, cell, lysate or extract derived from a cell, or a molecule derived from a cell.

The following is a list of abbreviations and the corresponding meanings as used interchangeably herein:
$^1$H-NMR=proton nuclear magnetic resonance
AcOH=acetic acid
BOC=tert-butoxycarbonyl
BuLi=butyl lithium
Cat.=catalytic amount
CDI=Carbonyldiimidazole
$CH_2Cl_2$=dichloromethane
$CH_3CN$=acetonitrile
$CH_3I$=iodomethane
CHN analysis=carbon/hydrogen/nitrogen elemental analysis
CHNCl analysis=carbon/hydrogen/nitrogen/chlorine elemental analysis
CHNS analysis=carbon/hydrogen/nitrogen/sulfur elemental analysis
DEAD=diethylazodicarboxylate
DIAD=diisopropylazodicarboxylate
DI water=deionized water
DMA=N,N-dimethylacetamide
DMAC=N,N-dimethylacetamide
DMF=N,N-dimethylformamide
EDC=1-(3-dimethylaminopropyl)-3-ethylcarbodiimide hydrochloride
Et=ethyl
$Et_2O$=diethyl ether
$Et_3N$=triethylamine
EtOAc=ethyl acetate
EtOH=ethanol
FAB MS=fast atom bombardment mass spectroscopy
g=gram(s)
HOBT=1-hydroxybenzotriazole hydrate
HPLC=high performance liquid chromatography
i-Pr=iso propyl
i-Prop=iso propyl
$K_2CO_3$=potassium carbonate
$KMnO_4$=potassium permanganate
KOH=potassium hydroxide
KSCN=potassium thiocyanate
L=Liter
LiOH=lithium hydroxide
Me=methyl
MeOH=methanol
mg=milligram
$MgSO_4$=magnesium sulfate
ml=milliliter
mL=milliliter
MS=mass spectroscopy
NaH—sodium hydride
$NaHCO_3$=sodium bicarbonate
NaOH=sodium hydroxide
NaOMe=sodium methoxide
$NH_4^+HCO_2^-$=ammonium formate
NMR=nuclear magnetic resonance
Pd=palladium
Pd/C=palladium on carbon
Ph=phenyl
Pt=platinum
Pt/C=platinum on carbon
RPHPLC=reverse phase high performance liquid chromatography
RT=room temperature
t-BOC=tert-butoxycarbonyl
TFA=trifluoroacetic acid
THF=tetrahydrofuran
TLC—thin layer chromatography
TMS=trimethylsilyl
Δ=heating the reaction mixture The compounds as shown above can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

DETAILED DESCRIPTION OF THE PREFERRED EMBODIMENTS

In one embodiment, the compounds of the present invention correspond to formula (I)

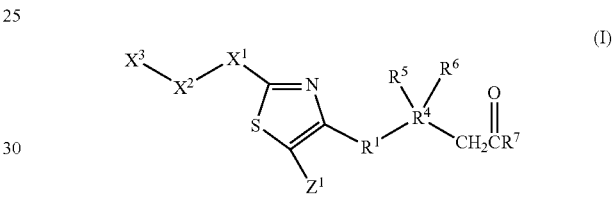

wherein:
$R^1$ is selected from the group consisting of —CH($R^2$)—, —N($R^3$)—, —O—, —S—, —S(O)$_2$—, —NHS(O)$_2$—, —S(O)$_2$NH— and —C(O)—;
$R^2$ is selected from the group consisting of hydrogen, hydroxy, and optionally substituted hydrocarbyl or alkoxy, wherein the optional substituents are selected from the group consisting of alkyl, halogen, hydroxy, alkoxy, amino, alkylamino, dialkylamino, cyano, acyl, —S—, —SO—, —SO$_2$—, sulfonamido, aryl, and heteroaryl, or $R^2$ in combination with $R^7$ and forms a lactone;
$R^3$ is selected from the group consisting of hydrogen and optionally substituted hydrocarbyl, heteroaryl, or acyl wherein the optional substituents are selected from the group consisting of alkyl, halogen, hydroxy, alkoxy, amino, alkylamino, dialkylamino, cyano, acyl, —S—, —SO—, —SO$_2$—, sulfonamido, aryl, and heteroaryl;
$R^4$ is carbon or nitrogen;
$R^5$ is selected from the group consisting of hydrogen, halo, and optionally substituted hydrocarbyl or heteroaryl, wherein the optional substituents are selected from the group consisting of alkyl, halogen, hydroxy, alkoxy, alkoxyalkyl, amino, alkylamino, dialkylamino, cyano, acyl, —S—, —SO—, —SO$_2$—, sulfonamido, heteroaryl, and optionally substituted aryl, wherein the optional substituent is halo, or $R^5$ together with $R^4$ and $R^6$ forms a monocyclic or bicyclic ring system;
$R^6$ is an electron pair when $R^4$ is nitrogen, or $R^6$ is heteroaryl when $R^4$ is carbon, or $R^6$ is hydrogen, halo, or optionally substituted hydrocarbyl, wherein the optional substituents are selected from the group consisting of alkyl, halogen, hydroxy, alkoxy, amino, alkylamino, dialkylamino, cyano, acyl, —S—, —SO—, —SO$_2$—, sulfonamido, aryl, and heteroaryl, or R⁶ together with R⁴ and R⁵ forms a monocyclic or bicyclic ring system;

R⁷ is selected from the group consisting of —OR⁸, —SR⁸, and —NR⁸R⁹ or R⁷ in combination with R2 forms a lactone;

R⁸ is selected from the group consisting of hydrogen and optionally substituted hydrocarbyl, wherein the optional substituents are selected from the group consisting of alkyl, halogen, hydroxy, alkoxy, amino, alkylamino, dialkylamino, cyano, acyl, —S—, —SO—, —SO₂—, sulfonamido, aryl, and heteroaryl;

R⁹ is selected from the group consisting of hydrogen, hydroxy, and optionally substituted hydrocarbyl or alkoxy, wherein the optional substituents are selected from the group consisting of alkyl, halogen, hydroxy, alkoxy, amino, alkylamino, dialkylamino, cyano, acyl, —S—, —SO—, —SO₂—, sulfonamido, aryl, and heteroaryl;

X¹ is selected from the group consisting of a bond, —O—, —CH₂—, —CH₂O—, —NH—, —C(O)—, —S—, —S(O)—, —CH(OH)—, —S(O)₂—, alkenyl, and alkynyl;

X² is a linker comprising a chain of 1 to 5 atoms, optionally substituted, selected from the group consisting of C, O, S and N;

X³ is heterocyclic; and

Z¹ is selected from the group consisting of hydrogen, hydroxy, cyano, and optionally substituted hydrocarbyl or heteroaryl, wherein the optional substituents are selected from the group consisting of alkyl, halogen, hydroxy, alkoxy, amino, alkylamino, dialkylamino, cyano, acyl, —S—, —SO—, —SO₂—, sulfonamido, aryl, and heteroaryl.

In one embodiment for compounds having formula I, Z¹ is alkyl or substituted alkyl. In yet another embodiment, Z¹ is aryl, substituted aryl, or heteroaryl. In the previous two embodiments, substituents are selected from the group consisting of alkyl, halogen, hydroxy, alkoxy, amino, alkylamino, dialkylamino, cyano, acyl, —S—, —SO—, —SO₂—, sulfonamido, aryl, and heteroaryl. In a further embodiment, Z¹ is hydrogen.

In another embodiment for compounds having formula I, X² is a carbon chain comprising 1 to 3 carbon atoms. In yet another embodiment, X² is optionally substituted. In the previous embodiment, substituents are selected from the group consisting of alkyl, halogen, hydroxy, alkoxy, amino, alkylamino, dialkylamino, cyano, acyl, —S—, —SO—, —SO₂—, sulfonamido, aryl, and heteroaryl. In still another embodiment, X² comprises a carbon-carbon unsaturated bond.

In a further embodiment for compounds having formula I, X³ is selected from the group consisting of:

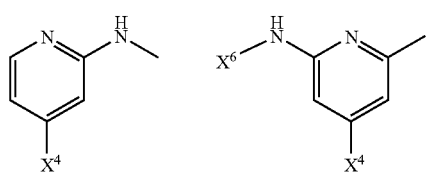

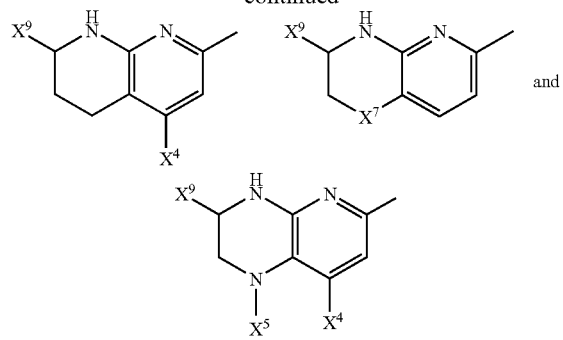

wherein:

X⁴ is hydrogen, hydroxy, alkoxy, hydrocarbyl, substituted hydrocarbyl, amino, alkylamino, dialkylamino, cyclicamino, heteroaryl, or —NHSO₂R¹¹ wherein R¹¹ is alkyl or aryl;

X⁵, X⁶, and X⁸ are independently hydrogen, hydrocarbyl, substituted hydrocarbyl, or heteroaryl;

X⁷ is —CH₂—, —CH₂O—, —OCH₂—, —S—, —SO—, —SO₂—, —O—, —C(O)—, —CH(OH)—, —NH—, or —NX⁸; and X⁹ is =O, or —OH.

In another embodiment for compounds having formula I, X¹ is oxygen. In a further embodiment, X¹ is —S—, —SO—, or —SO₂—. In still another embodiment, X¹ is —NH—. In yet another embodiment X¹ is —CH₂—.

In another embodiment for compounds having formula I, R¹ is —CH(R²)— wherein R² is hydrogen, hydroxy, or alkoxy. In yet another embodiment, R¹ is —N(R³)— wherein R³ is selected from the group consisting of hydrogen, alkyl, substituted alkyl, substituted aryl, and heteroaryl.

In a further embodiment, R¹ is —S—, —SO—, —SO₂—, NHS(O)₂—, or

—S(O)₂NH—. In still further embodiment, R¹ is oxygen.

In another embodiment for compounds having formula I, R⁴ is carbon. In yet another embodiment, R⁴ is nitrogen.

In a further embodiment for compounds having formula I, R⁵ is hydrogen. In another embodiment, R⁵ is alkyl or substituted alkyl. In yet another embodiment, R⁵ is aryl or heteroaryl.

In another embodiment for compounds having formula I, R⁶ is an electron pair.

In yet another embodiment, R⁶ is selected from the group consisting of hydrogen, alkyl, substituted alkyl, aryl, and heteroaryl.

In another embodiment for compounds having formula I, R⁷ is hydroxy.

The present invention is further directed to compounds that correspond to formula (II).

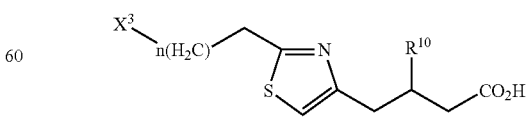

wherein:
X³ is heterocyclic;
n is 0–3; and $R^{10}$ is aryl, substituted aryl, aralkyl, substituted aralkyl, heteroaralkyl, substituted heteroaralkyl, heteroaryl.

In one embodiment for compounds having formula II, $X^3$ is selected from the group consisting of:

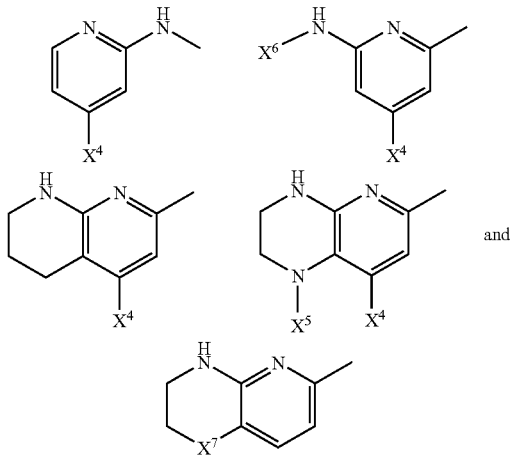

wherein:
$X^4$ is hydrogen, hydroxy, alkoxy, hydrocarbyl, substituted hydrocarbyl, amino, or heteroaryl;
$X^5$, $X^6$, and $X^8$ are independently hydrogen, hydrocarbyl, substituted hydrocarbyl, or heteroaryl; and
$X^7$ is —$CH_2$—, —$CH_2O$—, —$OCH_2$—, —S—, —O—, —C(O)—, —CH(OH)—, —NH—, or —$NX^8$.

In another embodiment for compounds having formula II, $R^{10}$ is aryl, substituted aryl, or heteroaryl. In a further embodiment, $R^{10}$ is monocyclic. In still further embodiment, $R^{10}$ is bicyclic. In yet another embodiment, $R^{10}$ optionally contains 0 to 5 heteroatoms. In the previous four embodiments, substituents are selected from the group consisting of alkyl, haloalkyl, aryl, heteroaryl, halogen, alkoxyalkyl, aminoalkyl, hydroxy, nitro, alkoxy, hydroxyalkyl, thioalkyl, amino, alkylamino, arylamino, alkylsulfonamide, acyl, acylamino, alkylsulfone, sulfonamide, allyl, alkenyl, methylenedioxy, ethylenedioxy, alkynyl, carboxamide, cyano, and —$(CH_2)_m$COR wherein m is 0–2 and R is hydroxy, alkoxy, alkyl and amino.

In another embodiment for compounds having formula II, the compound is the "R" or "S" isomer.

The present invention is further directed to compounds that correspond to formula (III).

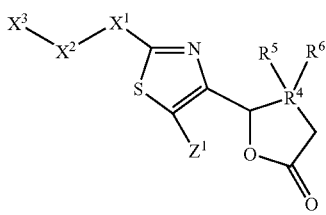

III wherein:
$R^4$ is carbon or nitrogen;
$R^5$ is hydrogen, hydrocarbyl, substituted hydrocarbyl, halo or heteroaryl, or $R^5$ together with $R^4$ and $R^6$ form a monocyclic or bicyclic ring system;
$R^6$ is an electron pair when $R^4$ is nitrogen, or $R^6$ is hydrogen, hydrocarbyl, substituted hydrocarbyl, halo or heteroaryl when $R^4$ is carbon, or $R^6$ together with $R^4$ and $R^5$ form a monocyclic or bicyclic ring system;
$X^1$ is a bond, —O—, —$CH_2$—, —$CH_2O$—, —NH—, —C(O)—, —S—, —S(O)—, —CH(OH)—, or —$S(O)_2$—;
$X^2$ is linker comprising a chain of 1 to 6 atoms, optionally substituted, optionally unsaturated, selected from the group consisting of C, O, S, and N;
$X^3$ is heterocyclic; and
$Z^1$ is hydrogen, hydrocarbyl, substituted hydrocarbyl, heteroaryl, hydroxy, or cyano.

In one embodiment for compounds having formula III, $Z^1$ is alkyl or substituted alkyl. In yet another embodiment, $Z^1$ is aryl, substituted aryl, or heteroaryl. In the previous two embodiments, substituents are selected from the group consisting of alkyl, halogen, hydroxy, alkoxy, amino, alkylamino, dialkylamino, cyano, acyl, —S—, —SO—, —$SO_2$—, sulfonamido, aryl, and heteroaryl. In a further embodiment, $Z^1$ is hydrogen.

In another embodiment for compounds having formula III, $X^2$ is a carbon chain comprising 1 to 3 carbon atoms. In yet another embodiment, $X^2$ is optionally substituted. In the previous embodiment, substituents are selected from the group consisting of alkyl, halogen, hydroxy, alkoxy, amino, alkylamino, dialkylamino, cyano, acyl, —S—, —SO—, —$SO_2$—, sulfonamido, aryl, and heteroaryl. In still another embodiment, $X^2$ comprises a carbon-carbon unsaturated bond.

In a further embodiment for compounds having formula III, $X^3$ is selected from the group consisting of:

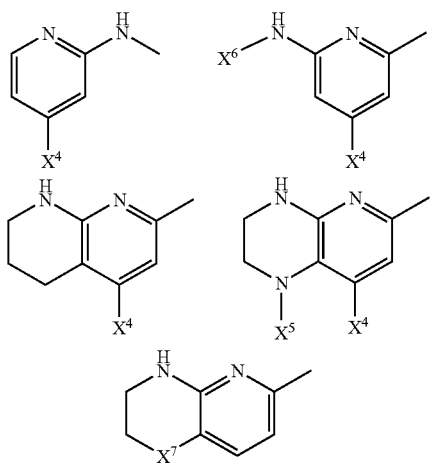

wherein:
$X^4$ is hydrogen, hydroxy, alkoxy, hydrocarbyl, substituted hydrocarbyl, amino, alkylamino, dialkylamino, cyclicamino, heteroaryl, or —$NHSO_2R^{11}$ wherein $R^{11}$ is alkyl or aryl;
$X^5$, $X^6$ and $X^8$ are independently hydrogen, hydrocarbyl, substituted hydrocarbyl, or heteroaryl; and
$X^7$ is —$CH_2$—, —$CH_2O$—, —$OCH_2$—, —S—, —SO—, —$SO_2$—, —O—, —C(O)—, —CH(OH)—, —NH—, or —$NX^8$.

In another embodiment for compounds having formula III, $X^1$ is oxygen. In a further embodiment, $X^1$ is —S—, —SO—, or —SO$_2$—. In still another embodiment, $X^1$ is —NH—. In yet another embodiment $X^1$ is —CH$_2$—.

In another embodiment for compounds having formula III, $R^4$ is carbon. In yet another embodiment, $R^4$ is nitrogen.

In a further embodiment for compounds having formula III, $R^5$ is hydrogen. In another embodiment, $R^5$ is alkyl or substituted alkyl. In yet another embodiment, $R^5$ is aryl or heteroaryl.

In another embodiment for compounds having formula III, $R^6$ is an electron pair. In yet another embodiment, $R^6$ is selected from the group consisting of hydrogen, alkyl, substituted alkyl, aryl, and heteroaryl.

In a further embodiment for compounds having formula III, $R^4$, $R^5$, and $R^6$ form a ring. In yet another embodiment, the ring formed by $R^4$, $R^5$, and $R^6$ is monocyclic. In still another embodiment, the ring formed by $R^4$, $R^5$, and $R^6$ is bicyclic.

The present invention is further directed to compounds that correspond to formula (IV).

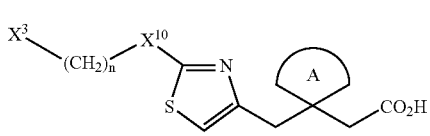

IV wherein:
$X^3$ is heterocyclic;
n is 0–3;
$X^{10}$ is —O—, —S—, —SO—, —SO$_2$—, or —CH$_2$—; and
A is aryl, substituted aryl, or heteroaryl.

In one embodiment for compounds having formula IV, $X^3$ is selected from the group consisting of:

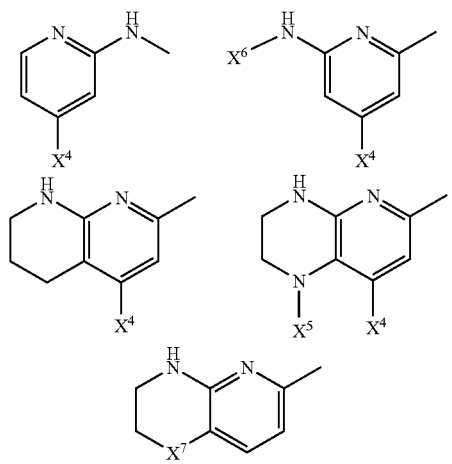

wherein:
$X^4$ is hydrogen, hydroxy, alkoxy, hydrocarbyl, substituted hydrocarbyl, amino, or heteroaryl;
$X^5$, $X^6$, and $X^8$ are independently hydrogen, hydrocarbyl, substituted hydrocarbyl, or heteroaryl; and
$X^7$ is —CH$_2$—, —CH$_2$O—, —OCH$_2$—, —S—, —O—, —C(O)—, —CH(OH)—, —NH—, or —NX$^8$.

In another embodiment for compounds having formula IV, A is aryl, substituted aryl, or heteroaryl. In a further embodiment, A is monocyclic. In still further embodiment, A is bicyclic. In yet another embodiment, A optionally contains 0 to 3 heteroatoms. In the previous four embodiments, substituents are selected from the group consisting of alkyl, haloalkyl, aryl, heteroaryl, halogen, alkoxyalkyl, aminoalkyl, hydroxy, nitro, alkoxy, hydroxyalkyl, thioalkyl, amino, alkylamino, arylamino, alkylsulfonamide, acyl, acylamino, alkylsulfone, sulfonamide, allyl, alkenyl, methylenedioxy, ethylenedioxy, alkynyl, carboxamide, cyano, and —(CH$_2$)$_m$COR wherein m is 0–2 and R is hydroxy, alkoxy, alkyl and amino.

The present invention includes within its scope prodrugs of the compounds of this invention. Any compound corresponding to any of formulas (I)–(IV), having one or more prodrug moieties as part of the molecule, can be converted under physiological conditions to the biologically active drug by a number of chemical and biological mechanisms. In general terms, these prodrug conversion mechanisms are hydrolysis, reduction, oxidation, and elimination.

In general, such prodrugs will be functional derivatives of the compounds of this invention which are readily convertible in vivo into the required compound. For example, prodrugs of a carboxylic acid include an ester, an amide, or an ortho-ester. Thus, in the methods of treatment of the present invention, the term "administering" shall encompass the treatment of the various conditions described with the compound specifically disclosed or with a compound which may not be specifically disclosed, but which converts to the compound of Formula I in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

A further aspect of the invention encompasses conversion of the prodrug to the biologically active drug by elimination of the prodrug moiety. Generally speaking, in this embodiment the prodrug moiety is removed under physiological conditions with a chemical or biological reaction. The elimination results in removal of the prodrug moiety and liberation of the biologically active drug. Any compound of the present invention corresponding to formulas (I)–(IV) may undergo any combination of the above detailed mechanisms to convert the prodrug to the biologically active compound. For example, a particular compound may undergo hydrolysis, oxidation, elimination, and reduction to convert the prodrug to the biologically active compound. Equally, a particular compound may undergo only one of these mechanisms to convert the prodrug to the biologically active compound.

The compounds of the present invention can have chiral centers and occur as racemates, racemic mixtures, diastereomeric mixtures, and as individual diastereomers or enantiomers, with all isomeric forms included in the present invention. Therefore, where a compound is chiral, the separate enantiomers or diastereomers, substantially free of the other, are included within the scope of the present invention; further included are all mixtures of the enantiomers or diastereomers. The compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, I-isomers, the racemic mixtures thereof and other mixtures thereof, as falling within the scope of compounds having any of formulas (I)–(IV). The terms "cis" and "trans", as used herein, denote a form of geometric isomerism in which two carbon atoms connected by a double bond will each have a hydrogen atom on the same side of the double bond ("sis") or on opposite sides of the double bond ("trans"). Some of the compounds described contain alkenyl groups, and are meant to include both cis and trans or "E" and "Z" geometric forms. Furthermore, some of the compounds described contain one or more stereocenters and are meant to include R, S, and mixtures or R and S forms for each stereocenter present. Also included within the scope of the invention are polymorphs, or hydrates or other modifiers of the compounds of invention.

Moreover, the family of compounds or isomers having any of formulas (I)–(IV) also include the pharmaceutically acceptable salts thereof. Pharmaceutically acceptable salts of such tautomeric, geometric or stereoisomeric forms are also included within the invention. The term "pharmaceutically-acceptable salt" embraces salts commonly used to form alkali metal salts and to form addition salts of free acids or free bases. The nature of the salt is not critical, provided that it is pharmaceutically acceptable. Suitable pharmaceutically acceptable acid addition salts of the compounds may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, and galacturonic acid. Suitable pharmaceutically-acceptable base addition salts of the compounds include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compound by reacting, for example, the appropriate acid or base with the selected compound of any of formulas (I)–(IV).

The present invention also comprises a pharmaceutical composition comprising a therapeutically effective amount of the compound of the invention in association with at least one pharmaceutically acceptable carrier, adjuvant or diluent. Pharmaceutical compositions of the present invention can comprise the active compounds of formulas (I)–(IV) in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended.

For the selective inhibition or antagonism of $\alpha_v\beta_3$ and/or $\alpha_v\beta_5$ integrins, compounds of the present invention may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, transmuscular infusion techniques or intraperitonally.

The compounds of the present invention are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar to the medicinal arts.

Accordingly, the present invention provides a method of treating conditions mediated by selectively inhibiting or antagonizing the $\alpha_v\beta_3$ and/or $\alpha_v\beta_5$ cell surface receptor which method comprises administering a therapeutically effective amount of a compound selected from the class of compounds depicted in the above formulas, wherein one or more compound is administered in association with one or more non-toxic, pharmaceutically acceptable carriers and/or diluents and/or adjuvants (collectively referred to herein as "carrier" materials) and if desired other active ingredients. More specifically, the present invention provides a method for selective antagonism of the $\alpha_v\beta_3$ and/or $\alpha_v\beta_5$ cell surface receptors over $\alpha_{IIb}\beta_3$ or $\alpha_v\beta_6$ integrin receptors. Most preferably the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating retinopathy including macular degeneration and diabetic retinopathy, inhibiting arthritis, psoriasis and periodontal disease, and inhibiting smooth muscle cell migration including restenosis. In another embodiment, the present invention provides a method for treating osteoporosis. In yet another embodiment, the present invention provides a method for treating tumor metastasis. In another embodiment, the present invention provides a method of treating inappropriate angiogenesis.

Based upon standard laboratory experimental techniques and procedures well known and appreciated by those skilled in the art, as well as comparisons with compounds of known usefulness, the compounds of Formula I can be used in the treatment of patients suffering from the above pathological conditions. One skilled in the art will recognize that selection of the most appropriate compound of the invention is within the ability of one with ordinary skill in the art and will depend on a variety of factors including assessment of results obtained in standard assay and animal models.

Treatment of a patient afflicted with one of the pathological conditions comprises administering to such a patient an amount of compound of the Formula I which is therapeutically effective in controlling the condition or in prolonging the survivability of the patient beyond that expected in the absence of such treatment. As used herein, the term "inhibition" of the condition refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

As stated previously, the compounds of the invention can be used in a variety of biological, prophylactic or therapeutic areas. It is contemplated that these compounds are useful in prevention or treatment of any disease state or condition wherein the $\alpha_v\beta_3$ and/or $\alpha_v\beta_5$ integrin plays a role.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 1.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100, 200 and 500 milligrams of the active ingredient for the symptomatic adjustment of the dosage to the patient to be treated. A medicament typically contains from about 0.01 mg to about 500 mg of the active ingredient, preferably, from about 1mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regiment.

For administration to a mammal in need of such treatment, the compounds in a therapeutically effective amount are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions useful in the present invention may be subjected to conventional pharmaceutical operations such as sterilization and/or may contain conventional pharmaceutical adjuvants such as preservatives, stabilizers, wetting agents, emulsifiers, buffers, etc.

EXAMPLES

In general, the compounds in the present invention were synthesized following the method shown in Scheme 1. Compound 1 was treated with $Z^{11}Z^{22}CHN^2$ (where $Z^{11}$ is either hydrogen, hydrocarbyl, or substituted hydrocarbyl and $Z^{22}$ is hydrogen or trialkylsilyl), followed by HY (where Y is either Cl, Br, or I). Compound 3 was treated with $H_2S$, $P_2S_5$, $Na_2S$ or NaHS to yield compound 4. Condensation of compound 2 and compound 4 generates the substituted heterocyclic compound $5^a$, where $R^7$ is alkoxy. Saponification of $5^a$ yields compound $5^b$ where $R^7$ is hydroxy.

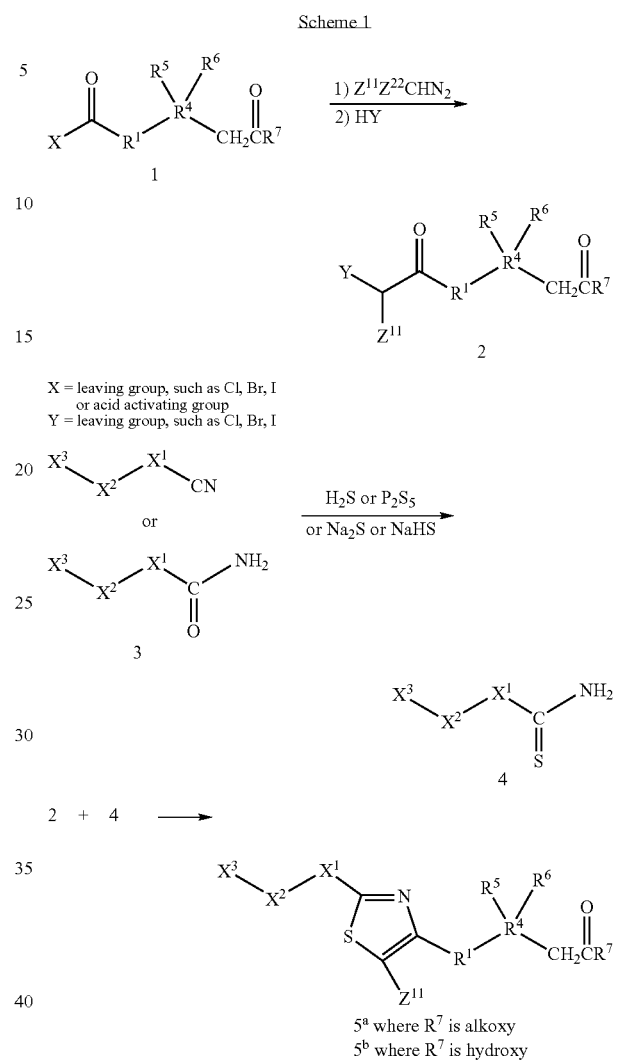

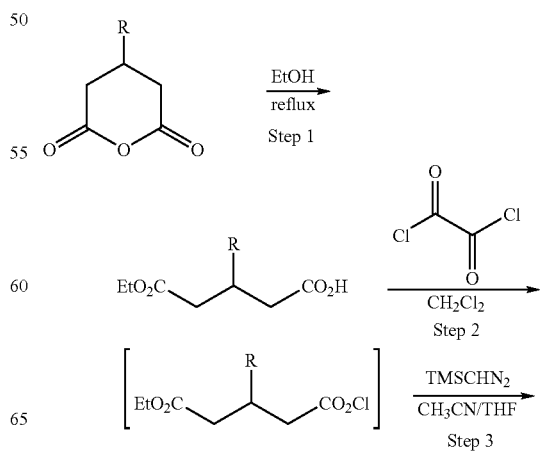

-continued

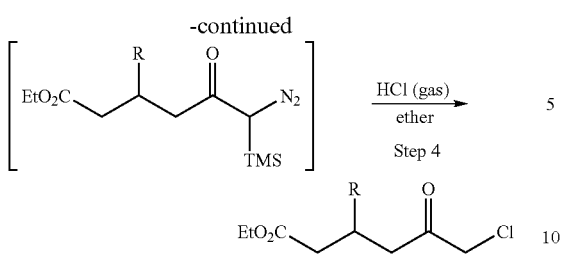

Step 4

Example A

Ethyl 6-chloro-3-[2-(4-chlorophenyl)-1,3-thiazol-5-yl]-5-oxohexanoate

R =

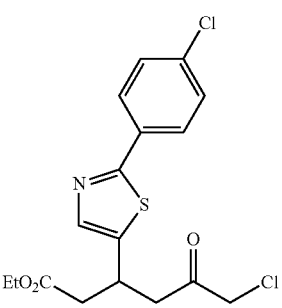

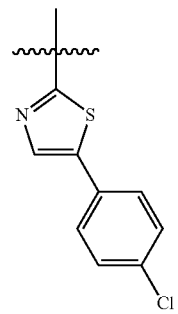

Step 1

3-[2-(4-chlorophenyl)-1,3-thiazol-5-yl]-5-ethoxy-5-oxopentanoic acid

4-[2-(4-chlorophenyl)-1,3-thiazol-5-yl]dihydro-2H-pyran-2,6(3H)-dione (3.0 g; 9.68 mmol) was dissolved in absolute EtOH (35 mL) and heated to reflux for 48 hours. The reaction was cooled and concentrated in vacuo to give the desired crude product. $^1$H NMR (DMSO-$d_6$) δ1.13 (t, 3H), 2.62–2.91 (m, 4H), 3.78–3.87 (m, 1H), 4.03 (q, 2H), 7.52–7.58 (m, 2H), 7.72 (s, 1H), 7.86–7.93 (m, 2H).

Step 2

Ethyl 5-chloro-3-[2-(4-chlorophenyl)-1,3-thiazol-5-yl]-5-oxopentanoate

3-[2-(4-chlorophenyl)-1,3-thiazol-5-yl]-5-ethoxy-5-oxopentanoic acid (9.68 mmol) was dissolved in CH$_2$Cl$_2$ (10 mL) and cooled to 0° C. Oxalyl Chloride (2.0M in CH$_2$Cl$_2$; 25 mL) was added slowly. One drop of DMF was added to the reaction mixture. The reaction was warmed to room temperature and stirred for 18 hours. The reaction was concentrated in vacuo to give the crude product.

Step 3

4-[2-(4-chlorophenyl)-1,3-thiazol-5-yl]-6-ethoxy-2,6-dioxo-1-(trimethylsilyl)hexane-1-diazonium Ethyl 5-chloro-3-[2-(4-chlorophenyl)-1,3-thiazol-5-yl]-5-oxopentanoate (9.68 mmol) was dissolved in a 1:1 mixture of CH$_3$CN/THF (20 mL) and cooled to 0° C. Trimethylsilyl) diazomethane (2.0M in hexanes; 7.26 mL, 14.52 mmol) was slowly added over 5 minutes. The reaction was warmed to room temperature and stirred for 18 hours. The reaction was concentrated in vacuo to give the crude product.

Step 4

Ethyl 6-chloro-3-[2-(4-chlorophenyl)-1,3-thiazol-5-yl]-5-oxohexanoate

4-[2-(4-chlorophenyl)-1,3-thiazol-5-yl]-6-ethoxy-2,6-dioxo-1-(trimethylsilyl)hexane-1-diazonium (9.684 mmol) was dissolved in diethyl ether (20 mL) and cooled to 0° C. HCl gas was bubbled into the solution periodically for 5 minutes. The reaction was warmed to room temperature and stirred for 18 hours. The reaction was concentrated in vacuo and the residue was purified via silica gel chromatography (eluent: 10% ethyl acetate in hexane) to give a yellow sticky solid. Yield: 230 mg (6% over 4 steps). $^1$H NMR (DMSO-$d_6$) δ1.12 (t, 3H), 2.64–2.85 (m, 2H), 3.04–3.10 (m, 2H), 3.88–3.97 (m, 1H), 4.03 (q, 2H), 4.45–4.58 (AB q, 2H), 7.52–7.57 (m, 2H), 7.71 (s, 1H), 7.85–7.92 (m, 2H).

Example B

Ethyl 6-chloro-3-(3-fluoro-4-methoxyphenyl)-5-oxohexanoate

R =

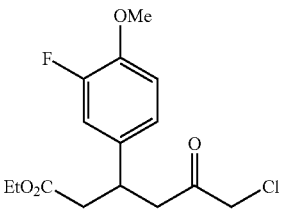

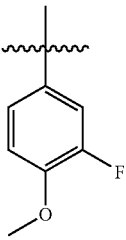

The title compound was prepared according to the method as described for preparing EXAMPLE A using the appropriate anhydride. $^1$H NMR (DMSO-$d_6$) δ1.07 (t, 3H), 2.52–2.60 (m, 2H), 2.85–2.93 (m, 2H), 3.42–3.52 (m, 1H), 3.78 (s, 3H), 3.95 (q, 2H), 4.35–4.50 (AB q, 2H), 6.98–7.08 (m, 2H), 7.12–7.18 (m, 1H).

Example C

Ethyl 6-chloro-5-oxo-3-(2-phenyl-1,3-thiazol-5-yl)hexanoate

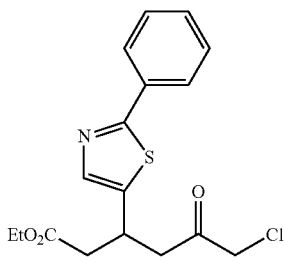

R =

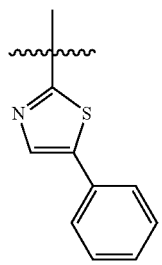

The title compound was prepared according to the method as described for preparing EXAMPLE A using the appropriate anhydride. $^1$H NMR (DMSO-d$_6$) δ1.12 (t, 3H), 2.64–2.85 (m, 2H), 3.03–3.09 (m, 2H), 3.88–3.97 (m, 1H), 4.03 (q, 2H), 4.45–4.58 (AB q, 2H), 7.40–7.52 (m, 3H), 7.68 (s, 1H), 7.83–7.90 (m, 2H).

Example D

Ethyl 6-chloro-3-(3-fluorophenyl)-5-oxohexanoate

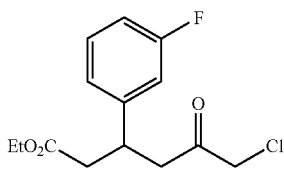

R =

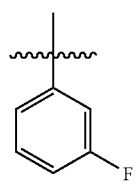

The title compound was prepared according to the method as described for preparing EXAMPLE A using the appropriate anhydride. $^1$H NMR (DMSO-d$_6$) δ 1.05 (t, 3H), 2.50–2.78 (m, 4H), 3.40–3.50 (m, 1H), 3.95 (q, 2H), 6.98–7.05 (m, 1H), 7.08–7.15 (m, 2H), 7.28–7.35 (m, 1H).

Elemental Analysis Calculated for C$_{14}$H$_{16}$NClFO$_3$ C, 58.64; H, 5.62. Found C, 58.41; H, 5.79.

Example E

Ethyl 6-chloro-3-(3,5-dimethoxyphenyl)-5-oxohexanoate

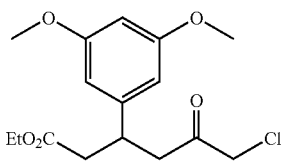

R =

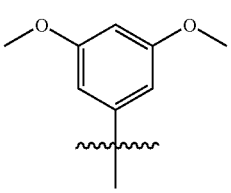

The title compound was prepared according to the method as described for preparing EXAMPLE A using the appropriate anhydride. $^1$H NMR (DMSO-d$_6$) δ 1.08 (t, 3H), 2.50–2.68 (m, 2H), 2.84–3.98 (m, 2H), 3.40–3.50 (m, 1H), 3.70 (s, 3H), 3.97 (q, 2H), 4.35–4.50 (AB q, 2H), 6.31–6.34 (m, 1H), 6.38–6.42 (m, 2H).

Elemental Analysis Calculated for C$_{16}$H$_{21}$ClO$_5$ C, 58.45; H, 6.44; Cl, 10.78. Found C, 58.39; H, 6.42; Cl, 10.63.

Example F

Ethyl 3-(1,3-benzodioxol-5-yl)-6-chloro-5-oxohexanoate

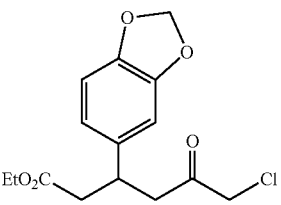

R =

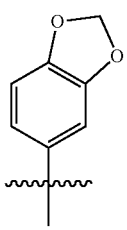

The title compound was prepared according to the method as described for preparing EXAMPLE A using the appropriate anhydride. $^1$H NMR (DMSO-d$_6$) δ1.05 (t, 3H), 2.45–2.66 (m, 2H), 2.87(d, 2H), 3.42–3.48 (m, 1H), 3.90–3.95 (m, 2H), 4.40 (ABq, 2H), 5.95 (s, 2H), 6.67 (dd, 1H), 6.77 (d, 1H), 6.85 (d, 1H).

Elemental Analysis Calculated for $C_{15}H_{17}O_5Cl$ C, 57.61; H, 5.48; Cl, 11.34. Found C, 57.41; H, 5.64; Cl, 11.07.

Example G

Ethyl 6-chloro-3-(4-methylphenyl)-5-oxohexanoate

R =

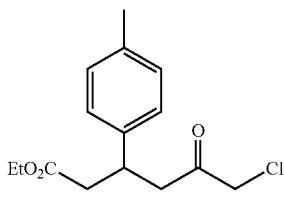

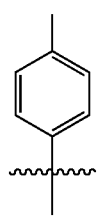

The title compound was prepared according to the method as described for preparing EXAMPLE A using the appropriate anhydride. $^1$H NMR (DMSO-$d_6$) δ 7.10(m, 4H), 4.40(m, 2H), 3.95(m, 2H), 3.50(s, 1H), 2.90(d, 2H), 2.60(m, 4H), 2.23(s, 3H), 1.05(m, 3H). Mass Spectrum: (MH$^+$) =283.05

Example H

Ethyl 6-chloro-3-(2-methyl-1,3-benzothiazol-5-yl)-5-oxohexanoate

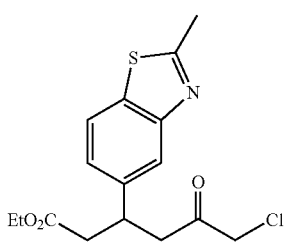

R =

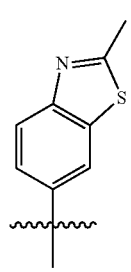

The title compound was prepared according to the method as described for preparing EXAMPLE A using the appropriate anhydride. $^1$H NMR (DMSO-$d_6$) δ 7.95(d, 1H), 7.82(d, 1H), 7.30(m, 1H), 4.55(m, 1H), 3.90(m, 2H), 3.65 (m, 1H), 2.95(m, 2H), 2.75(s, 3H), 2.62(m, 2H), 1.05(m, 3H). Mass Spectrum: (MH$^+$)=340.0.

Example I

Ethyl 6-chloro-3-(4-chlorophenyl)-5-oxohexanoate

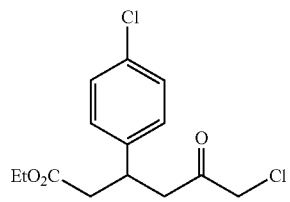

R =

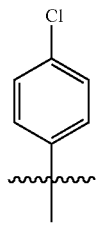

The title compound was prepared according to the method as described for preparing EXAMPLE A using the appropriate anhydride. $^1$H NMR (DMSO-$d_6$) δ 7.35–7.25(m, 4H), 4.50–4.45(AB q, 2H), 3.95(q, 2H), 3.57–3.48(m, 1H), 2.95–2.92(m, 2H), 2.73–2.48(m, 2H), 1.05(t, 3H).

Example J

Ethyl 6-chloro-5-oxo-3-quinolin-3-ylhexanoate

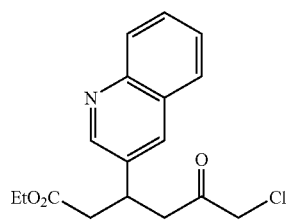

R =

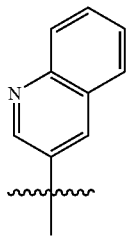

The title compound was prepared according to the method as described for preparing EXAMPLE A using the appropriate anhydride. $^1$H NMR (DMSO-$d_6$) δ 9.42(m, 1H), 9.05(m, 1H), 8.50(m, 1H), 8.25(m, 1H), 8.05(m, 1H), 7.89 (m, 1H), 4.55–4.40(AB q, 2H), 3.95(t, 2H), 3.85–3.75(m, 1H), 3.25–3.08(m, 2H), 2.98–2.80(m, 2H), 1.05(t, 3H).

Example K

Ethyl 6-chloro-3-(3,4-difluorophenyl)-5-oxohexanoate

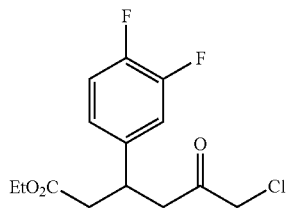

The title compound was prepared according to the method as described for preparing EXAMPLE A using the appropriate anhydride. $^1$H NMR (DMSO-$d_6$) δ 7.3–7.45 (m, 2H), 7.15(m, 1H), 4.45(m, 2H), 3.93 (m, 2H), 3.52 (m, 1H), 2.92 (m, 2H), 2.5–2.7 (m, 2H), 1.05 (t, 3H). Mass Spectrum: (MH$^+$)=305.0

Example L

Ethyl 6-chloro-3-(6-methoxypyridin-3-yl)-5-oxohexanoate

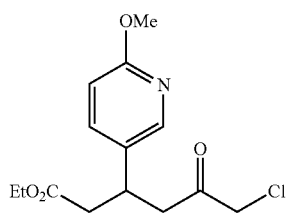

The title compound was prepared according to the method as described for preparing EXAMPLE A using the appropriate anhydride. $^1$H NMR (DMSO-$d_6$) δ 8.02 (d, 1H), 7.64 (q, 1H), 6.72 (d, 1H), 4.47 (q, 2H), 3.85 (m, 2H), 3.5 (m, 1H), 2.63 (m, 2H), 1.05 (t, 3H); Mass Spectrum: (MH$^+$)=300.10.

Example M

(S)-Ethyl 3-(1,3-benzodioxol-5-yl)-6-chloro-5-oxo-hexanoate

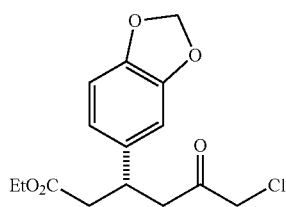

R =

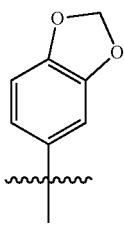

Step 1

Ethyl (3S)-3-(1,3-benzodioxol-5-yl)-5-chloro-5-oxopentanoate (S)-3-(1,3-benzodioxol-5-yl)-5-ethoxy-5-oxopentanoic acid (2.01, 7.2 mmol) was dissolved in methylene chloride (50 mL) at O° C. under argon. An excess of oxalyl chloride (3 mL) was added along with a drop of dimethylformamide (catalyst). The reaction mixture was stirred 24 hours and concentrated to a crude brown oil. Yield=2.23 g (>100%).

Step 2

The crude brown oil was dissolved in a 1:1 mixture of THF and CH$_3$CN (50 mL total). This mixture was cooled to 0° C. and 7.2 mL (2.0M hexane solution, 14.4 mmol) of trimethylsilyldiazomethane was added. This reaction mixture was warmed to room temperature and stirred for 24 hours. The yellow solution concentrated in vacuo to provide the crude-diazo ketone as yellow oil.

Step 3

(S)-Ethyl 3-(1,3-benzodioxol-5-yl)-6-chloro-5-oxo-hexanoate

The oil was dissolved in diethyl ether (40 mL) and cooled to 0° C. HCl (g) was bubbled vigorously through the ethereal solution for 10 minutes. This solution was warmed to room temperature and concentrated in vacuo to afford a reddish oil. This oil was purified by silica gel chromatography using the Biotage Flash 40M column using 9:1 hexanes/ethyl acetate as the elutant to afford 1.89 g (84% overall) as a light yellow solid. $^1$H NMR (DMSO-$d_6$) δ1.05 (t, 3H), 2.45–2.66 (m, 2H), 2.87(d, 2H), 3.42–3.48 (m, 1H), 3.90–3.95 (m, 2H), 4.40 (ABq, 2H), 5.95 (s, 2H), 6.67 (dd, 1H), 6.77 (d, 1H), 6.85 (d, 1H).

Elemental Analysis Calculated for $C_{15}H_{17}O_5Cl$ Expected: C, 57.61; H, 5.48. Found: C, 57.70; H, 5.56.

Example N

Ethyl 6-chloro-3-(2-cyclopropyl-1,3-thiazol-5-yl)-5-oxohexanoate

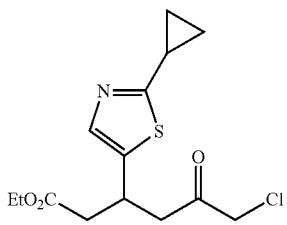

The title compound was prepared according to the method as described for preparing EXAMPLE A using the appropriate anhydride. 44% yield. $^1$H NMR (CDCl$_3$) δ 7.18 (s, 1H), 4.05 (m, 2H), 3.95 (s, 2H), 3.9 (m, 1H), 3.05–2.85 (m, 2H), 2.65–2.55 (m, 2H), 2.15 (m, 1H), 1.15 (m, 3H), 1.05 (m, 2H), 0.95 (m, 2H).

Example O

Ethyl 6-chloro-3-[2-(methoxymethyl)-1,3-thiazol-5-yl]-5-oxohexanoate

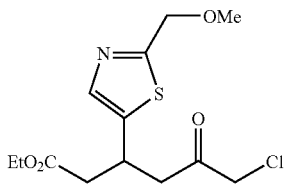

The title compound was prepared according to the method as described for preparing EXAMPLE A using the appropriate anhydride. 52% yield. $^1$H NMR (CDCl$_3$) δ 7.39 (s, 1H), 4.52 (s, 2H), 4.0 (q, 2H), 3.95 (m, 1H), 3.52 (s, 2H), 3.32 (s, 3H), 3.05–2.95 (m, 2H), 2.7–2.55 (m, 2H), 1.15 (t, 3H).

Scheme 3

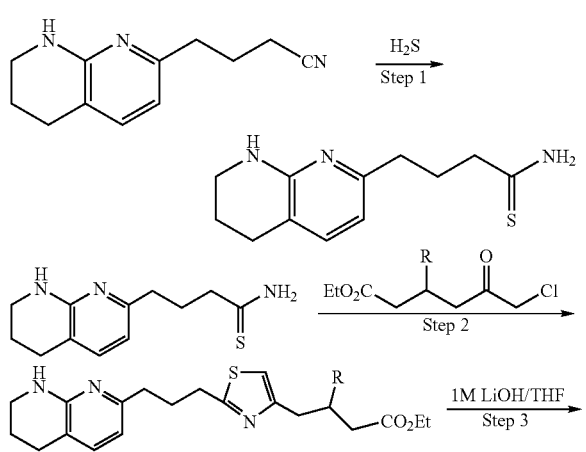

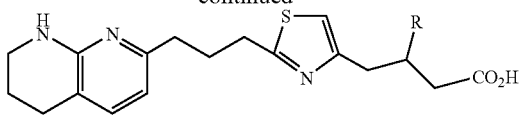

Procedures for Scheme 3

Example 1

3-[2-(4-chlorophenyl)-1,3-thiazol-5-yl]-4-{2-[3-(5,6,7,8-tetrahydro-1,8-naphthyridin-2-yl)propyl]-1,3-thiazol-4-yl}butanoic acid hydrochloride

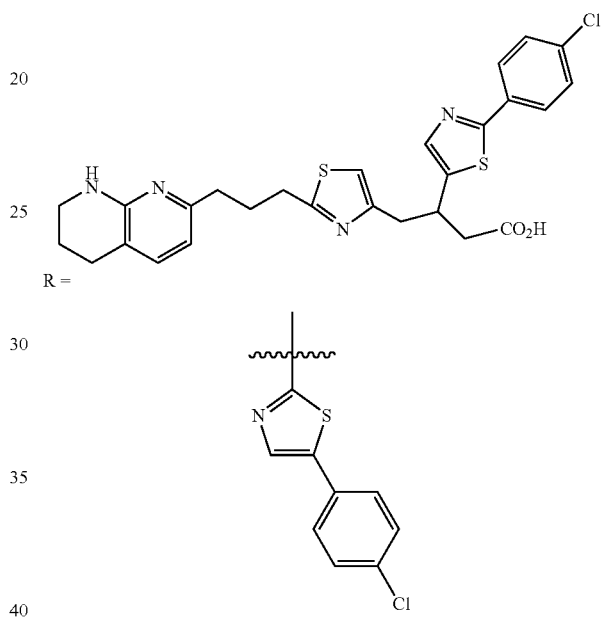

Step 1

4-(5,6,7,8-tetrahydro-1,8-naphthyridin-2-yl)butanethioamide

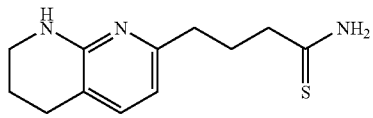

4-(5,6,7,8-tetrahydro-1,8-naphthyridin-2-yl)butanenitrile (5.00 g; 24.8 mmoles) was dissolved in pyridine (20 mL) and triethylamine (2.0 mL). Hydrogen sulfide was bubbled into the solution for 5 min, the flask was sealed and allowed to stand at ambient temperature for 8 days. The solvent was removed under a stream of nitrogen and the residue was purified by chromatography on silica gel, eluting with CH$_2$Cl$_2$/MeOH (100:8). Following evaporation of solvent the product 4-(5,6,7,8-tetrahydro-1,8-naphthyridin-2-yl)butanethioamide was obtained as a red-brown sticky oil (3.1 g, 53%). $^1$H NMR (DMSO-d$_6$) 9.32 (s, 1H), 9.18 (s, 1H), 7.02 (d, 1H), 6.30 (s, 1H), 6.23 (d, 1H), 3.22 (m, 2H), 2.60 (m, 2H), 2.44 (m, 4H), 1.95 (m, 2H), 1.75 (m, 2H). Mass Spectrum: (MH$^+$)=236.

Step 2

Ethyl 3-[2-(4-chlorophenyl)-1,3-thiazol-5-yl]-4-{2-[3-(5,6,7,8-tetrahydro-1,8-naphthyridin-2-yl)propyl]-1,3-thiazol-4-yl}butanoate hydrochloride thyl 6-chloro-3-[2-(4-chlorophenyl)-1,3-thiazol-5-yl]-5-oxohexanoate, Scheme 2, Example A, (230 mg, 0.595 mmol) and 4-(5,6,7,8-tetrahydro-1,8-naphthyridin-2-yl)butanethioamide, Scheme 3, Step 1, (140 mg, 0.595 mmol) was dissolved in 1,4-dioxane (5 mL) and heated to 120° C. for 18 hours. The solvent was removed and the residue purified via reverse phase HPLC to give the product (180 mg, 44%). $^1$H NMR (DMSO-d$_6$) δ1.10 (t, 3H), 1.77–1.85 (m, 2H), 2.02–2.11 (m, 2H), 2.68–2.90 (m, 6H), 2.95–3.18 (m, 4H), 3.38–3.46 (m, 2H), 3.86–3.95 (m, 2H), 4.00 (q, 2H), 6.55 (d, 1H), 7.18 (s, 1H), 7.48–7.55 (m, 2H), 7.57 (d, 1H), 7.62 (s, 1H), 7.80–7.85 (m, 2H).

Step 3

3-[2-(4-Chlorophenyl)-1,3-thiazol-5-yl]-4-{2-[3-(5,6,7,8-tetrahydro-1,8-naphthyridin-2-yl)propyl]-1,3-thiazol-4-yl}butanoic acid hydrochloride Ethyl 3-[2-(4-chlorophenyl)-1,3-thiazol-5-yl]-4-{2-[3-(5,6,7,8-tetrahydro-1,8-naphthyridin-2-yl )propyl]-1,3-thiazol-4-yl}butanoate hydrochloride (Scheme 3, Step 2), (180 mg, 0.281 mmol) was dissolved in THF. Upon cooling to 0° C., 0.84 mL LiOH (1M) was added and allowed to stir at room temperature overnight. The reaction was acidified to pH=1 with HCl and concentrated in vacuo. The residue was purified via reverse phase HPLC to yield the title compound (239 mg, 78%). $^1$H NMR (DMSO-d$_6$) δ1.77–1.87 (m, 2H), 2.02–2.12 (m, 2H), 2.61–2.82 (m, 6H), 2.95–3.18 (m, 4H), 3.39–3.45 (m, 2H), 3.85–3.95 (m, 1H), 6.55 (d, 1H), 7.18 (s, 1H), 7.48–7.54 (m, 2H), 7.56 (d, 1H), 7.62 (s, 1H), 7.80–7.85 (m, 2H).

Elemental Analysis Calculated for $C_{27}H_{27}ClN_4O_2S_2$·2 HCl·3 H$_2$O Expected: C, 48.69; H, 5.30; N, 8.41. Found: C, 48.37; H, 5.33; N, 8.29.

The following compounds (Examples 2–14 and 16–20) were synthesized in the same manner as Scheme 3, Example 1, using the appropriate α-chloroketone prepared in Scheme 2.

Example 2

3-(3-fluoro-4-methoxyphenyl)-4-{2-[3-(5,6,7,8-tetrahydro-1,8-naphthyridin-2-yl)propyl]-1,3-thiazol-4-yl}butanoic acid hydrochloride

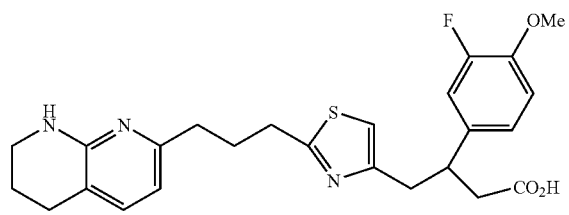

Step 2

Ethyl 3-(3-fluoro-4-methoxyphenyl)-4-{2-[3-(5,6,7,8-tetrahydro-1,8-naphthyridin-2-yl)propyl]-1,3-thiazol-4-yl}butanoate hydrochloride Yield=83%. $^1$H NMR (DMSO-d$_6$) δ1.04 (t, 3H), 1.78–1.87 (m, 2H), 2.03–2.13 (m, 2H), 2.54–2.78 (m, 6H), 2.88–3.03 (m, 4H), 3.38–3.50 (m, 3H), 3.77 (s, 3H), 3.91 (q, 2H), 6.58 (d, 1H), 6.91–6.95 (m, 2H), 6.98 (d, 1H), 7.07–7.14 (m, 1H), 7.60 (d, 1H).

Step 3

3-(3-fluoro-4-methoxyphenyl)-4-{2-[3-(5,6,7,8-tetrahydro-1,8-naphthyridin-2-yl)propyl]-1,3-thiazol-4-yl}butanoic acid hydrochloride Yield=88%. $^1$H NMR (DMSO-d$_6$) δ1.78–1.85 (m, 2H), 2.02–2.12 (m, 2H), 2.48–2.63 (m, 2H), 2.70–2.77 (m, 4H), 2.88–3.04 (m, 4H), 3.38–3.47 (m, 3H), 3.76 (s, 3H), 6.58 (d, 1H), 6.91–6.95 (m, 1H), 6.96–7.04 (m, 2H), 7.05–7.10 (m, 1H), 7.60 (d, 1H).

Elemental Analysis Calculated for $C_{25}H_{28}FN_3O_3S$·1.0 HCl·2.0 H$_2$O Expected: C, 55.39; H, 6.14; N, 7.75. Found: C, 55.43; H, 6.25; N, 7.72.

Example 3

3-(2-phenyl-1,3-thiazol-5-yl)-4-{2-[3-(5,6,7,8-tetrahydro-1,8-naphthyridin-2-yl)propyl]-1,3-thiazol-4-yl}butanoic acid hydrochloride

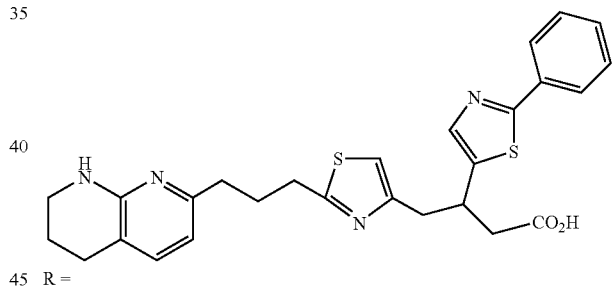

R =

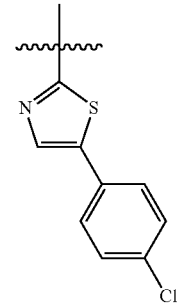

Step 2

Ethyl 3-(2-phenyl-1,3-thiazol-5-yl)-4-{2-[3-(5,6,7,8-tetrahydro-1,8-naphthyridin-2-yl)propyl]-1,3-thiazol-4-yl}butanoate hydrochloride Yield=83%. $^1$H NMR (DMSO-d$_6$) δ1.10 (t, 3H), 1.78–1.86 (m, 2H), 2.05–2.14 (m, 2H), 2.68–2.89 (m, 6H), 2.96–3.19 (m, 4H), 3.39–3.46 (m, 2H), 3.89–3.97 (m,1H), 4.00 (q, 2H), 6.55 (d, 1H), 7.19 (s, 1H), 7.42–7.49 (m, 3H), 7.55 (d, 1H), 7.61 (s, 1H), 7.79–7.85 (m, 2H).

Step 3

3-(2-phenyl-1,3-thiazol-5-yl)-4-{2-[3-(5,6,7,8-tetrahydro-1,8-naphthyridin-2-yl)propyl]-1,3-thiazol-4-yl}butanoic acid hydrochloride Yield=77%. $^1$H NMR (DMSO-$d_6$) δ1.78–1.87 (m, 2H), 2.02–2.12 (m, 2H), 2.61–2.82 (m, 6H), 2.95–3.18 (m, 4H), 3.38–3.47 (m, 2H), 3.85–3.94 (m, 1H), 6.55 (d, 1H), 7.14 (s, 1H), 7.41–7.48 (m, 3H), 7.55 (d, 1H), 7.57 (s, 1H), 7.77–7.84 (m, 2H).

Elemental Analysis Calculated for $C_{27}H_{28}N_4O_2S_2 \cdot 1.4$ HCl·0.5 H$_2$O Expected C, 55.56; H, 5.25; N, 9.60. Found C, 55.54; H, 5.64; N, 9.66.

Example 4

3-(3-fluorophenyl)-4-{2-[3-(5,6,7,8-tetrahydro-1,8-naphthyridin-2-yl)propyl]-1,3-thiazol-4-yl}butanoic acid hydrochloride

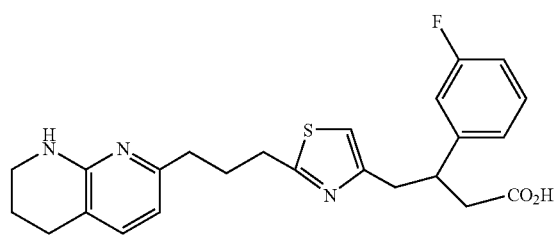

R =

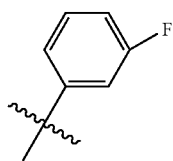

Step 2

Ethyl 3-(3-fluorophenyl)-4-{2-[3-(5,6,7,8-tetrahydro-1,8-naphthyridin-2-yl)propyl]-1,3-thiazol-4-yl}butanoate hydrochloride Yield=76%. $^1$H NMR (DMSO-$d_6$) δ 1.02 (t, 3H), 1.77–1.86 (m, 2H), 2.02–2.12 (m, 2H), 2.60–2.77 (m, 6H), 2.92–3.06 (m, 4H), 3.38–3.45 (m, 2H), 3.48–3.58 (m, 1H), 3.92 (q, 2H), 6.58 (d, 1H), 6.92–7.10 (m, 3H), 7.03 (s, 1H), 7.22–7.30 (m, 1H), 7.60 (d, 1H).

Elemental Analysis Calculated for $C_{24}H_{27}N_3O_2SiF \cdot 1.0$ HCl,·2.0 H$_2$O Expected C, 57.82; H, 6.53; N, 7.78. Found C, 57.87; H, 6.55; N, 7.68.

Step 3

3-(3-Fluorophenyl)-4-{2-[3-(5,6,7,8-tetrahydro-1,8-naphthyridin-2-yl)propyl]-1,3-thiazol-4-yl}butanoic acid hydrochloride Yield=94%. $^1$H NMR (DMSO-$d_6$) δ 1.69–1.78 (m, 2H), 1.91–2.01 (m, 2H), 2.23–2.38 (m, 2H), 2.44–2.52 (m, 2H), 258–2.65 (m, 2H), 2.70–3.08 (m, 4H), 3.20–3.27 (m, 2H), 3.47–3.57 (m, 1H), 6.25 (s, 1H), 6.84 (s, 1H), 6.84–6.91 (m, 1H), 6.95–7.00 (m, 1H), 7.02 (d, 1H), 7.15–7.24 (m, 1H).

High Resolution Mass Spectral Data:
Calculated Mass: 439.1733; Found Mass: 439.1730

Example 5

3-(3,5-dimethoxyphenyl)-4-{2-[3-(5,6,7,8-tetrahydro-1,8-naphthyridin-2-yl)propyl]-1,3-thiazol-4-yl}butanoic acid hydrochloride

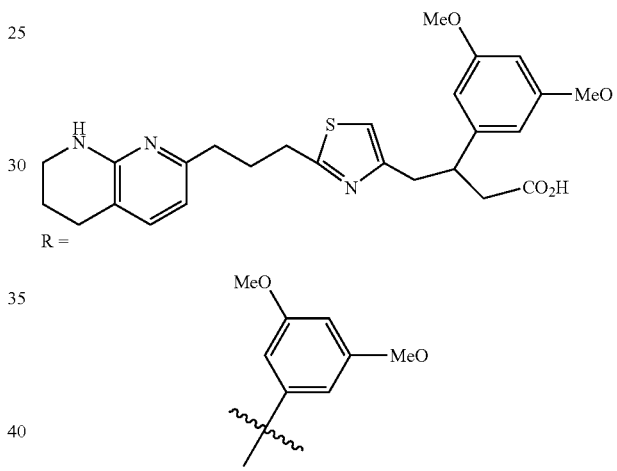

Step 2

Ethyl 3-(3,5-dimethoxyphenyl)-4-{2-[3-(5,6,7,8-tetrahydro-1,8-naphthyridin-2-yl)propyl]-1,3-thiazol-4-yl}butanoate hydrochloride Yield=55%. $^1$H NMR (CDCl$_3$) δ 8.50 (s, N—H), 7.38 (d, 1H), 6.85(s, 1H), 6.55(d, 1H), 6.38(d, 2H), 6.28(m, 1H), 4.05(m, 2H), 3.75(s, 6H), 3.60(m, 1H), 3.50(m, 2H), 3.30(m, 4H), 2.85(m, 2H), 2.75(m, 2H), 2.70(m, 2H), 2.45(m, 2H), 1.95(m, 2H), 1.15(m, 3H).

Step 3

3-(3,5-Dimethoxyphenyl)-4-{2-[3-(5,6,7,8-tetrahydro-1,8-naphthyridin-2-yl)propyl]-1,3-thiazol-4-yl}butanoic acid hydrochloride Yield=79%. $^1$H NMR (DMSO-$d_6$) δ 8.10(s, 1H), 7.59(d, 1H), 7.05(s, 1H), 6.59(d, 1H), 6.35(d, 2H), 6.28(m, 1H), 3.58(s, 6H), 3.45(m, 3H), 3.05(m, 4H), 2.75(m, 4H), 2.55(m, 2H), 2.10(m, 2H), 1.83(m, 2H). Mass Spectrum: (MH$^+$) =482.40

Example 6

3-(1,3-benzodioxol-5-yl)-4-{2-[3-(5,6,7,8-tetrahydro-1,8-naphthyridin-2-yl)propyl]-1,3-thiazol-4-yl}butanoic acid hydrochloride

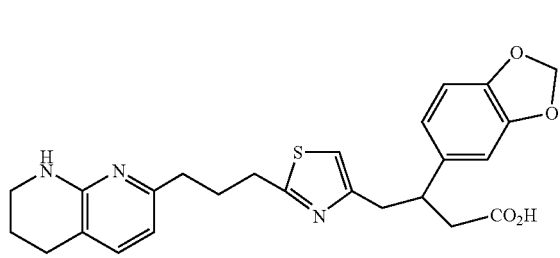

R =

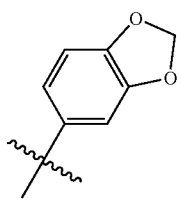

Step 2

Ethyl 3-(1,3-benzodioxol-5-yl)-4-{2-[3-(5,6,7,8-tetrahydro-1,8-naphthyridin-2-yl)propyl]-1,3-thiazol-4-yl}butanoate hydrochloride Yield=68%. $^1$H NMR (DMSO-d$_6$) δ 1.03 (t, 3H), 1.77–1.87 (m, 2H), 2.03–2.12 (m, 2H), 2.50–2.68 (m, 2H), 2.70–2.76 (m, 4H), 2.88–3.01 (m, 4H), 3.38–3.48 (m, 3H), 3.91 (q, 2H), 5.93 (s, 2H), 6.60 (d, 1H), 6.60–6.64 (m, 1H), 6.72–6.76 (m, 1H), 6.84–6.86 (m, 1H), 7.00–7.03 (m, 1H), 7.60 (d, 1H).

Step 3

3-(1,3-benzodioxol-5-yl)-4-{2-[3-(5,6,7,8-tetrahydro-1,8-naphthyridin-2-yl)propyl]-1,3-thiazol-4-yl}butanoic acid hydrochloride Yield=71%. $^1$H NMR (DMSO-d$_6$) δ 1.78–1.87 (m, 2H), 2.00–2.10 (m, 2H), 2.45–2.60 (m, 2H), 2.68–2.75 (m, 4H), 2.85–3.00 (m, 4H), 3.37–3.45 (m, 3H), 5.93 (s, 2H), 6.57 (d, 1H), 6.58–6.63 (m, 1H), 6.72–6.75 (m, 1H), 6.80–6.84 (m, 1H), 6.96–6.98 (m, 1H), 7.58 (d, 1H). Elemental Analysis Calculated for $C_{25}H_{27}N_3O_4S \cdot 1.0$ HCl, $\cdot 2.2$ H$_2$O Expected C, 55.41; H, 6.03; N, 7.76. Found C, 55.24; H, 5.87; N, 7.83.

Example 7

(3S)-3-(1,3-benzodioxol-5-yl)-4-{2-[3-(5,6,7,8-tetrahydro-1,8-naphthyridin-2-yl)propyl]-1,3-thiazol-4-yl}butanoic acid hydrochloride

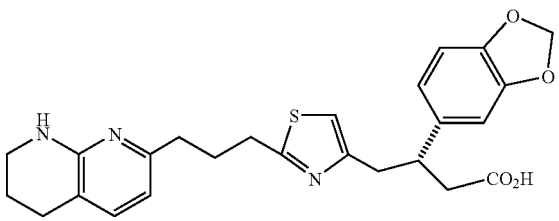

R =

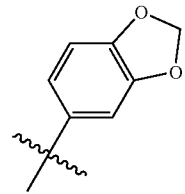

Step 2

(3S)-Ethyl 3-(1,3-benzodioxol-5-yl)-4-{2-[3-(5,6,7,8-tetrahydro-1,8-naphthyridin-2-yl)propyl]-1,3-thiazol-4-yl}butanoate hydrochloride Yield=51%. $^1$H NMR (DMSO-d$_6$) δ 1.03 (t, 3H), 1.77–1.87 (m, 2H), 2.03–2.12 (m, 2H), 2.50–2.68 (m, 2H), 2.70–2.76 (m, 4H), 2.88–3.01 (m, 4H), 3.38–3.48 (m, 3H), 3.91 (q, 2H), 5.93 (s, 2H), 6.60 (d, 1H), 6.60–6.64 (m, 1H), 6.72–6.76 (m, 1H), 6.84–6.86 (m, 1H), 7.00–7.03 (m, 1H), 7.60 (d, 1H).

Step 3

(3S)-3-(1,3-benzodioxol-5-yl)-4-{2-[3-(5,6,7,8-tetrahydro-1,8-naphthyridin-2-yl)propyl]-1,3-thiazol-4-yl}butanoic acid hydrochloride Yield=78%. $^1$H NMR (DMSO-d$_6$) δ 1.78–1.87 (m, 2H), 2.00–2.10 (m, 2H), 2.45–2.60 (m, 2H), 2.68–2.75 (m, 4H), 2.85–3.00 (m, 4H), 3.37–3.45 (m, 3H), 5.93 (s, 2H), 6.57 (d, 1H), 6.58–6.63 (m, 1H), 6.72–6.75 (m, 1H), 6.80–6.84 (m, 1H), 6.96–6.98 (m, 1H), 7.58 (d, 1H). Elemental Analysis Calculated for $C_{25}H_{27}N_3O_4S \cdot 1.0$ HCl, $\cdot 2.2$ H$_2$O C, 55.41; H, 6.03; N, 7.76. Found C, 55.24; H, 5.87; N, 7.83. Specific Rotation −26.4 (1.025 g/dL in MeOH) at 589 nm. X-ray analysis confirms the S stereochemistry

Example 8

3-(4-methylphenyl)-4-{2-[3-(5,6,7,8-tetrahydro-1,8-naphthyridin-2-yl)propyl]-1,3-thiazol-4-yl}butanoic acid hydrochloride

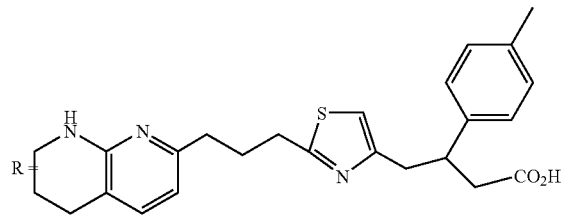

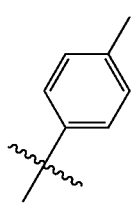

Step 2

Ethyl 3-(4-methylphenyl)-4-{2-[3-(5,6,7,8-tetrahydro-1,8-naphthyridin-2-yl)propyl]-1,3-thiazol-4-yl}butanoate hydrochloride Yield=53%. $^1$H NMR (DMSO-d$_6$) δ 8.08(s, 1H), 7.60(d, 2H), 7.05(m, 5H), 6.60(d, 2H), 3.89(m, 2H), 3.45(m, 3H), 2.95(m, 4H), 2.70(m, 4H), 2.60(m, 2H), 2.20(s, 3H), 2.08(m, 2H), 1.80(m, 2H), 1.03(m, 3H). Mass Spectrum: (MH$^+$)=464.30

Step 3

3-(4-methylphenyl)-4-{2-[3-(5,6,7,8-tetrahydro-1,8-naphthyridin-2-yl)propyl]-1,3-thiazol-4-yl}butanoic acid hydrochloride Yield=80%. $^1$H NMR (DMSO-d$_6$) δ 8.08(s, 1H), 7.56(d, 1H), 7.05(m, 5H), 6.60(d, 1H), 3.45(m, 3H), 3.05(m, 4 h), 2.72(m, 4H), 2.52(m, 2H), 2.50(m, 2H), 2.20(s, 3H), 1.80(m, 2H). Mass Spectrum: (MH$^+$)=436.10.

Example 9

3-(2-methyl-1,3-benzothiazol-5-yl)-4-{2-[3-(5,6,7,8-tetrahydro-1,8-naphthyridin-2-yl)propyl]-1,3-thiazol-4-yl}butanoic acid hydrochloride

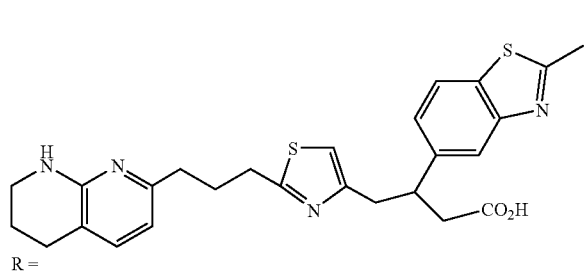

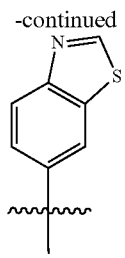

Step 2

Ethyl 3-(2-methyl-1,3-benzothiazol-5-yl)-4-{2-[3-(5,6,7,8-tetrahydro-1,8-naphthyridin-2-yl)propyl]-1,3-thiazol-4-yl}butanoate hydrochloride Yield=67%. $^1$H NMR (DMSO-d$_6$) δ 8.05(s, 1H), 7.85(d, 1H), 7.72(d, 1H), 7.60(d, 1H), 7.25(m, 1H), 7.00(s, 1H), 6.55(d, 1H), 3.90(m, 2H), 3.65(m, 1H), 3.46(m, 2H), 3.05(m, 2H), 2.95(m, 2H), 2.65(s, 3H), 2.62(m, 6H), 2.03(m, 2H), 1.84(m, 2H), 1.05(m, 3H). Mass Spectrum: (MH$^+$)=521.2.

Step 3

3-(2-methyl-1,3-benzothiazol-5-yl)-4-{2-[3-(5,6,7,8-tetrahydro-1,8-naphthyridin-2-yl)propyl]-1,3-thiazol-4-yl}butanoic acid hydrochloride Yield=89%. $^1$H NMR (DMSO-d$_6$) δ 7.95(s, 1H), 7.85(d, 1H), 7.72(d, 1H), 7.60(d, 1H), 7.25(m, 1H), 7.00(s, 1H), 6.55(d, 1H), 3.62(m, 1H), 3.46(m, 2H), 3.05(m, 2H), 2.95(m, 2H), 2.75(s, 3H), 2.68(m, 6H), 2.03(m, 2H), 1.84(m, 2H). Mass Spectrum: (MH$^+$)=493.2.

Example 10

3-(4-chlorophenyl)-4-{2-[3-(5,6,7,8-tetrahydro-1,8-naphthyridin-2-yl)propyl]-1,3-thiazol-4-yl}butanoic acid hydrochloride

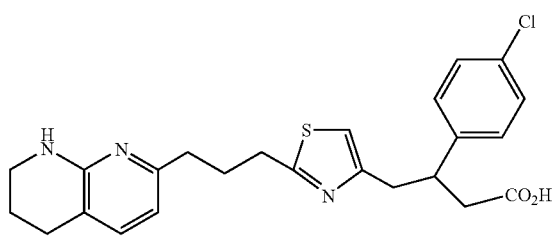

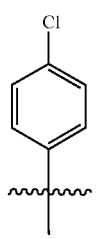

Step 2

Ethyl 3-(4-chlorophenyl)-4-{2-[3-(5,6,7,8-tetrahydro-1,8-naphthyridin-2-yl)propyl]-1,3-thiazol-4-yl}butanoate hydrochloride Yield=66%. $^1$H NMR (DMSO-$d_6$) δ 7.60(d, 1H), 7.30–7.20(m, 4H), 7.02(s, 1H), 6.58(d, 1H), 3.90(q, 2H), 3.55–3.45(m, 1H), 3.45–3.39(m, 2H), 3.05–2.90(m, 4H), 2.75–2.58(m, 6H), 2.12–2.01(m, 2H), 1.87–1.76(m, 2H), 1.05(t, 3H). Mass Spectrum: (MH$^+$)=485.18

Step 3

3-(4-chlorophenyl)-4-{2-[3-(5,6,7,8-tetrahydro-1,8-naphthyridin-2-yl)propyl]-1,3-thiazol-4-yl}butanoic acid hydrochloride Yield=67%. $^1$H NMR (DMSO-$d_6$) δ 7.60(d, 1H), 7.30–7.20(m, 4H), 7.01(s, 1H), 6.60 (d, 1H), 3.55–3.45(m, 1H), 3.45–3.39(m, 2H), 3.05–88(m, 4H), 2.78–2.50(m, 6H), 2.15–2.04(m, 2H), 1.88–1.77(m, 2H). Mass Spectrum: (MH$^+$)=456.15

Example 11

3-Quinolin-2-yl-4-{2-[3-(5,6,7,8-tetrahydro-1,8-naphthyridin-2-yl)propyl]-1,3-thiazol-4-yl}butanoic acid hydrochloride

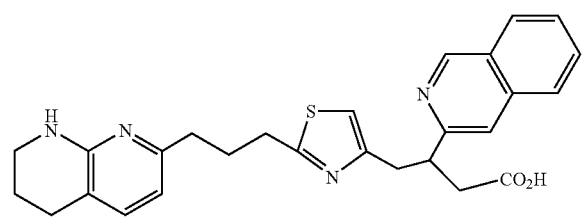

R =

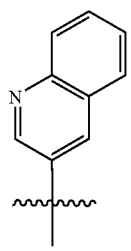

Step 2

Ethyl 3-quinolin-2-yl-4-{2-[3-(5,6,7,8-tetrahydro-1,8-naphthyridin-2-yl)propyl]-1,3-thiazol-4-yl}butanoate hydrochloride The product was isolated crude and used directly in following step.

Step 3

3-Quinolin-2-yl-4-{2-[3-(5,6,7,8-tetrahydro-1,8-naphthyridin-2-yl)propyl]-1,3-thiazol-4-yl}butanoic acid hydrochloride Yield=18%. $^1$H NMR (DMSO-$d_6$) δ 9.42(m, 1H), 9.05(m, 1H), 8.50(m, 1H), 8.25(m, 1H), 8.05(m, 1H), 7.89 (m, 1H),7.60(d, 1H), 7.15(s, 1H), 6.51(d, 2H), 3.95–3.83 (m, 1H), 3.96–3.39(m, 2H), 3.28–3.18(m, 2H), 3.00–2.85(m, 4H), 2.78–2.70(m, 2H), 2.67–2.57(m, 2H), 2.00–1.88(m, 2H), 1.87–1.78 (m, 2H). Mass Spectrum: (MH$^+$)=473.20

Elemental Analysis Calculated for $C_{27}H_{28}N_4O_2S$.2.6 HCl.4.4 $H_2O$ Expected C, 50.15; H, 6.14; N, 8.66. Found C, 50.51; H, 6.52; N, 8.58.

Example 12

3-(3,4-Difluorophenyl)4-{2-[3-(5,6,7,8-tetrahydro-1,8-naphthyridin-2-yl)propyl]-1,3-thiazol-4-yl}butanoic acid hydrochloride

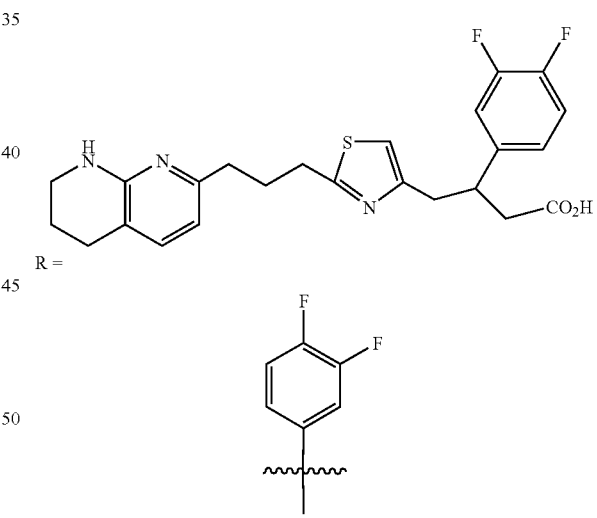

R =

Step 2

Ethyl 3-(3,4-difluorophenyl)-4-{2-[3-(5,6,7,8-tetrahydro-1,8-naphthyridin-2-yl)propyl]-1,3-thiazol-4-yl}butanoate hydrochloride Yield=89%. $^1$H NMR (DMSO-$d_6$) δ 8.05 (s, 1H), 7.6 (d, 1H), 7.25–7.42 (m, 2H), 7.02 (m, 2H), 6.58(d, 1H), 3.93 (m, 2H), 3.52 (m, 1H), 3.45 (m, 2H), 3.00 (m, 2H), 2.95 (m, 2H), 2.75 (m, 4H), 2.68 (m, 2H), 2.08 (m, 2H), 1.83 (m, 2H), 1.02 (m, 3H). Mass Spectrum: (MH$^+$)=486.2.

Step 3

3-(3,4-Difluorophenyl)-4-{2-[3-(5,6,7,8-tetrahydro-1,8-naphthyridin-2-yl)propyl]-1,3-thiazol-4-yl}butanoic acid hydrochloride

Yield=73%. $^1$H NMR (DMSO-d$_6$) δ 7.94 (s, 1H), 7.60 (d, 2H), 7.29 (m, 2H), 7.02 (, 2H), 6.60 (d, 1H), 3.50 (m, 1H), 3.45(m, 2H), 2.97 (m, 4H), 2.73 (m, 4H), 2.60 (m, 2H), 2.05 (m, 2H), 1.85 (m, 2H). Mass Spectrum: (MH$^+$)=458.2.

Example 13

3-(6-Methoxypyridin-3-yl)-4-{2-[3-(5,6,7,8-tetrahydro-1,8-naphthyridin-2-yl)propyl]-1,3-thiazol-4-yl}butanoic acid hydrochloride

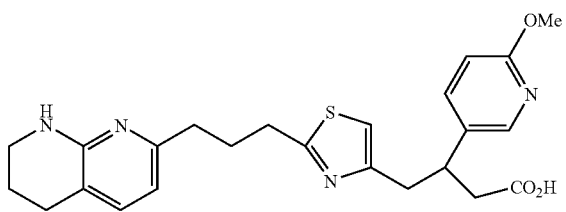

R =

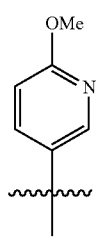

Step 2

Ethyl 3-(6-methoxypyridin-3-yl)-4-{2-[3-(5,6,7,8-tetrahydro-1,8-naphthyridin-2-yl)propyl]-1,3-thiazol-4-yl}butanoate hydrochloride

Yield=63%. $^1$H NMR (DMSO-d$_6$) δ 7.92 (s, 1H), 7.90 (d, 1H), 7.62 (m, 2H), 7.03 (s, 1H), 6.72 (d, 1H), 6.60 (d, 1H), 3.90 (m, 2H), 3.75 (s, 3H), 3.49 (m, 1H), 3.45 (m, 2H), 2.90–3.08 (m, 4H), 2.60–2.79 (m, 6H), 2.05 (m, 2H), 1.80 (m, 2H), 1.05 (t, 3H); Mass Spectrum: (MH$^+$)=481.2.

Step 3

3-(6-Methoxypyridin-3-yl)-4-{2-[3-(5,6,7,8-tetrahydro-1,8-naphthyridin-2-yl)propyl]-1,3-thiazol-4-yl}butanoic acid hydrochloride

Yield=66%. $^1$H NMR (DMSO-d$_6$) δ 8.23 (s, 1H), 7.96 (d, 1H), 7.70 (q, 1H), 7.61 (d, 1H), 7.10 (s, 1H), 6.80 (d, 1H), 6.60 (d, 1H), 3.80 (s, 3H), 3.40–3.60 (m, 3H), 2.90–3.10 (m, 4H), 2.52–2.80 (m, 6H), 2.15 (m, 2H), 1.86 (m, 2H); Mass Spectrum: (MH$^+$)=453.2.

Example 14

(S)-3-(6-Methoxypyridin-3-yl)-4-{2-[3-(5,6,7,8-tetrahydro-1,8-naphthyridin-2-yl)propyl]-1,3-thiazol-4-yl}butanoic acid hydrochloride

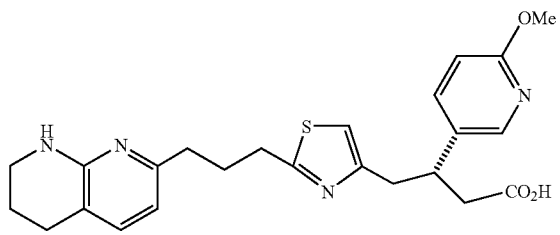

R =

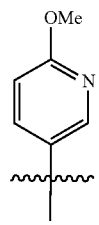

The following compound was chiral chromatographically resolved from Ethyl 3-(6-methoxypyridin-3-yl)-4-{2-[3-(5,6,7,8-tetrahydro-1,8-naphthyridin-2-yl)propyl]-1,3-thiazol-4-yl}butanoate (Scheme 3, Example 13, Step 2). The acid was synthesized in the same manner as Scheme 3, Example 13, Step 3.

Step 2

(S)-Ethyl 3-(6-methoxypyridin-3-yl)-4-{2-[3-(5,6,7,8-tetrahydro-1,8-naphthyridin-2-yl)propyl]-1,3-thiazol-4-yl}butanoate hydrochloride

Yield=43%. $^1$H NMR (DMSO-d$_6$) δ 7.92 (s, 1H), 7.90 (d, 1H), 7.62 (m, 2H), 7.03 (s, 1H), 6.72 (d, 1H), 6.60 (d, H), 3.90 (m, 2H), 3.75 (s, 3H), 3.49 (m, 1H), 3.45 (m, 2H), 2.90–3.08 (m, 4H), 2.60–2.79 (m, 6H), 2.05 (m, 2H), 1.80 (m, 2H), 1.05 (t, 3H); Mass Spectrum: (MH$^+$)=481.2.

Step 3

(S)-3-(6-Methoxypyridin-3-yl)-4-{2-[3-(5,6,7,8-tetrahydro-1,8-naphthyridin-2-yl)propyl]-1,3-thiazol-4-yl}butanoic acid hydrochloride

Yield=70%. $^1$H NMR (DMSO-d$_6$) δ 8.23 (s, 1H), 7.96 (d, 1H), 7.70 (q, 1H), 7.61 (d, 1H), 7.10 (s, 1H), 6.80 (d, 1H), 6.60 (d, 1H), 3.80 (s, 3H), 3.40–3.60 (m, 3H), 2.90–3.10 (m, 4H), 2.52–2.80 (m, 6H), 2.15 (m, 2H), 1.86 (m, 2H); Mass Spectrum: (MH$^+$)=453.2.

Elemental Analysis Calculated for C$_{24}$H$_{28}$N$_4$O$_3$S.HCl.0.4 H$_2$O, C, 58.09; H, 6.05; N, 11.29. Found C, 58.17; H, 6.35; N, 11.44.

Example 15

(3S)-3-(6-Hydroxypyridin-3-yl)-4-{2-[3-(5,6,7,8-tetrahydro-1,8-naphthyridin-2-yl)propyl]-1,3-thiazol-4-yl}butanoic acid hydrochloride

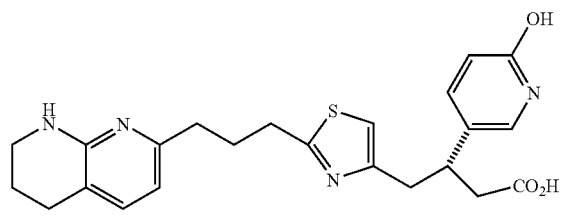

R =

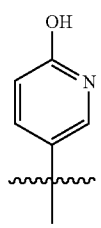

(3S)-3-(6-Hydroxypyridin-3-yl)-4-{2-[3-(5,6,7,8-tetrahydro-1,8-naphthyridin-2-yl)propyl]-1,3-thiazol-4-yl}butanoic acid hydrochloride (3S)-3-(6-methoxypyridin-3-yl)-4-{2-[3-(5,6,7,8-tetrahydro-1,8-naphthyridin-2-yl)propyl]-1,3-thiazol-4-yl}butanoic acid (Scheme 2, Example 14, Step 2) and concentrated ammonia hydroxide solution, the reaction was stirred until LCMS showed the reaction was completed. Purified by HPLC and obtained about 100 mg of final product. $^1$H NMR (DMSO-d$_6$) δ 8.00 (s, 1H), 7.62 (d, 1H), 7.49 (m, 1H), 7.15 (d, 1H), 7.05 (s, 1H), 6.60 (d, 1H), 6.40 (d, 1H), 3.45 (m, 2H), 3.25 (m, 1H), 2.74–3.00 (m, 4H), 2.73 (m, 4H), 2.45–2.60 (m, 2H), 2.10 (m, 2H), 1.85 (m, 2H); Mass Spectrum: (MH$^+$)=438.

Example 16

3-(2-Cyclopropyl-1,3-thiazol-5-yl)-4-{2-[3-(5,6,7,8-tetrahydro-1,8-naphthyridin-2-yl)propyl]-1,3-thiazol-4-yl}butanoic acid hydrochloride

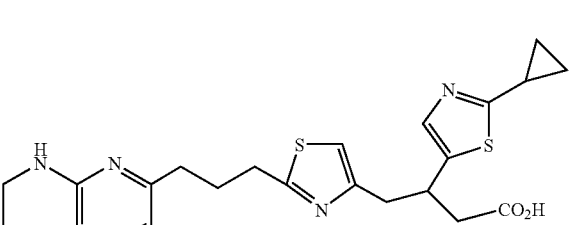

R =

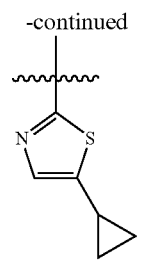

Step 2

Ethyl-3-(2-cyclopropyl-1,3-thiazol-5-yl)-4-{2-[3-(5,6,7,8-tetrahydro-1,8-naphthyridin-2-yl)propyl]-1,3-thiazol-4-yl}butanoate hydrochloride 32% yield. $^1$H NMR (400 MHz, CDCl$_3$) δ 8.15 (s, 1H), 7.82 (s, 1H), 7.31 (d, 1H), 6.47 (d, 1H), 4.35 (m, 1H), 4.05 (q, 2H), 3.48 (m, 2H), 3.38 (m, 4H), 2.90–2.65 (m, 7H), 2.40 (m, 2H), 1.95 (m, 2H), 1.50 (m, 2H), 1.35 (m, 2H), 1.20 (t, 3H).

Step 3

3-(2-Cyclopropyl-1,3-thiazol-5-yl)-4-{2-[3-(5,6,7,8-tetrahydro-1,8-naphthyridin-2-yl)propyl]-1,3-thiazol-4-yl}butanoic acid hydrochloride 70% yield. $^1$H NMR (DMSO-d$_6$) δ 7.92 (br s, 1H), 7.6 (d, 1H), 7.27 (s, 1H), 7.1 (s, 1H), 6.6 (d, 1H), 3.75 (m, 1H), 3.65 (m, 2H), 3.42 (m, 2H), 3.65 (m, 2H), 3.1–2.9 (m, 4H), 2.7 (m, 2H), 2.65–2.53 (m, 2H), 2.28 (m, 1H), 2.08 (m, 2H), 1.8 (m, 2H), 1.05 (m, 2H), 0.85 (m, 2H); Mass Spectrum: (MH$^+$)=469.1.

Example 17

3-[2-(Methoxymethyl)-1,3-thiazol-5-yl]-4-{2-[3-(5,6,7,8-tetrahydro-1,8-naphthyridin-2-yl)propyl]-1,3-thiazol-4-yl}butanoic acid hydrochloride

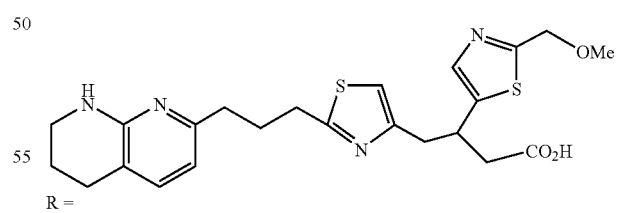

R =

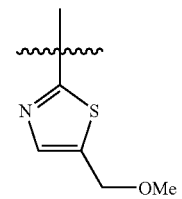

Step 2

Ethyl-3-[2-(methoxymethyl)-1,3-thiazol-5-yl]-4-{2-[3-(5,6,7,8-tetrahydro-1,8-naphthyridin-2-yl)propyl]-1,3-thiazol-4-yl}butanoate hydrochloride

22% yield. $^1$H NMR (CDCl$_3$) δ 7.60 (s, 1H), 7.30 (d, 1H), 6.92 (s, 1H), 6.45 (d, 1H), 4.75 (s, 2H), 4.30 (m, 1H), 4.00 (q, 2H), 3.45 (m, 2H), 3.42 (s, 3H), 3.35–3.20 (m, 4H), 2.85–2.60 (m, 6H), 2.35 (m, 2H), 1.90 (m, 2H), 1.15 (t, 3H).

Step 3

3-[2-(Methoxymethyl)-1,3-thiazol-5-yl]-4-{2-[3-(5,6,7,8-tetrahydro-1,8-naphthyridin-2-yl)propyl]-1,3-thiazol-4-yl}butanoic acid hydrochloride

89% yield. $^1$H NMR (DMSO-d$_6$) δ 7.95 (br s, 1H), 7.59 (d, 1H), 7.4 (s, 1H), 7.08 (s, 1H), 6.6 (d, 1H), 4.55 (s, 2H), 3.8 (m, 1H), 3.4 (m, 2H), 3.3 (s, 3H), 3.1–3.0 (m, 4H), 2.75 (m, 4H), 2.58 (m, 1H), 2.05 (m, 2H), 1.8 (m, 2H); Mass Spectrum: (MH$^+$)=473.1.

Scheme 4

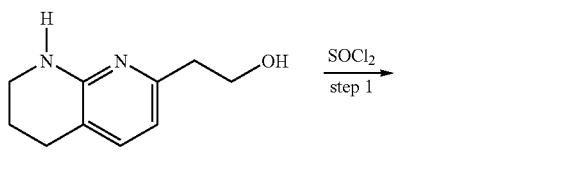

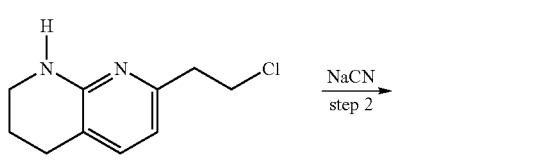

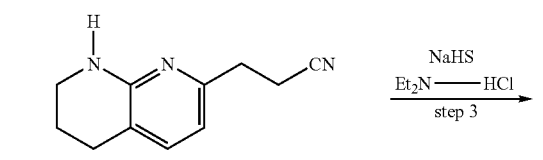

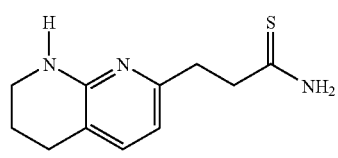

Procedures for Scheme 4

Step 1

7-(2-chloroethyl)-1,2,3,4-tetrahydro-1,8-naphthyridine

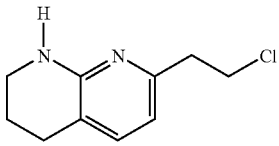

7-(2-hydroxyethyl)-1,2,3,4-tetrahydro-1,8-naphthyridine (5.00 g) was added to thionyl chloride (25 mL) and refluxed for 12 hour in benzene (100 mL). The resulting solution was concentrated and the red oil was dissolved in CH$_2$Cl$_2$ and washed with NaHCO$_3$ (satd). The CH$_2$Cl$_2$ layer was extracted, dried with Na$_2$SO$_4$, and concentrated in vacuo to afford 4.99 g (90%) of a tan solid. $^1$H NMR (DMSO-d$_6$) δ 7.06 (d, 1H), 6.35 (br s, 1H), 6.33 (d, 1H), 3.86 (t, 2H), 3.25 (m, 2H), 2.87 (t, 2H), 2.62 (t, 2H), 1.75 (pentet, 2H).

Step 2

3-(5,6,7,8-tetrahydro-1,8-naphthyridin-2-yl)propanenitrile

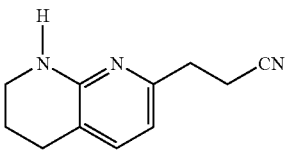

7-(2-chloroethyl)-1,2,3,4-tetrahydro-1,8-naphthyridine (500 mg) and NaCN (150 mg) were dissolved in DMF (in 15 mL) and the mixture was heated at 85° C. for 6 hrs. Cooled to 25° C. and the reaction was diluted with H$_2$O, extracted with CHCl$_3$, and the solution was washed with H$_2$O, dried with MgSO$_4$. The solution was concentrated to a yellow oil. Column purification (Ethyl acetate: Hexane=1:1) to yield a yellow solid 100 mg (8.9%). $^1$H NMR (DMSO-d$_6$) δ 7.06 (d, 1H), 6.45 (m, 2H), 3.33 (1, 2H), 2.75 (m, 4H), 2.63 (t, 2H), 1.75 (m, 2H).

Step 3

3-(5,6,7,8-tetrahydro-1,8-naphthyridin-2-yl)propanethioamide

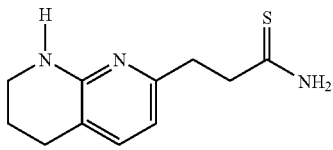

Reagents 3-(5,6,7,8-tetrahydro-1,8-naphthyridin-2-yl)propanenitrile (100 mg), sodium hydrogen sulfide hydrate (360 mg), diethylamine hydrochloride (530 mg) were mixed in DMF (10 mL). The mixture was warmed to 55° C. and stirred at this temperature for about 24 h. The mixture was allowed to cool and then diluted with water (30 mL) followed by extraction with ethyl acetate (3×25 mL). The extracts were combined and washed with water (3×20 mL). The organic phase was dried (magnesium sulfate) and filtered. The solution was concentrated and column purification (CHCl$_3$: MeOH=10:1) to yield a yellow solid 101 mg (89%). $^1$H NMR (DMSO-d$_6$) δ 9.30 (d, 2H), 7.10 (d, 2H), 6.35 (m, 2H), 3.25 (m, 2H), 2.80 (m, 2H), 2.75 (m, 2H), 2.64 (m, 2H), 1.72 (m, 2H).

Example 18

3-(1,3-benzodioxol-5-yl)-4-{2-[2-(5,6,7,8-tetrahydro-1,8-naphthyridin-2-yl)ethyl]-1,3-thiazol-4-yl}butanoic acid

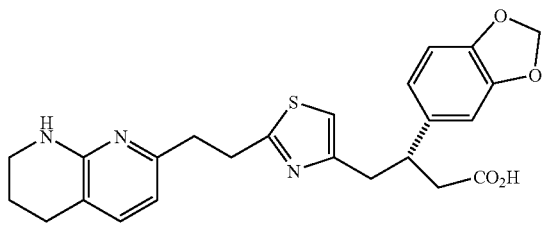

The following compound was synthesized in the same manner as Scheme 3, using 3-(5,6,7,8-tetrahydro-1,8-naphthyridin-2-yl)propanethioamide and the appropriate α-chloroketone prepared in Scheme 2

Ethyl 3-(1,3-benzodioxol-5-yl)-4-{2-[2-(5,6,7,8-tetrahydro-1,8-naphthyridin-2-yl)ethyl]-1,3-thiazol-4-yl}butanoate Yield=58%. $^1$H NMR (DMSO-d$_6$) δ 1.03 (t, 3H), 1.77–1.87 (m, 2H), 2.03–2.12 (m, 2H), 2.50–2.68 (m, 2H), 2.70–2.76 (m, 4H), 2.88–3.01 (m, 4H), 3.38–3.48 (m, 3H), 3.91 (q, 2H), 5.93 (s, 2H), 6.60 (d, 1H), 6.60–6.64 (m, 1H), 6.72–6.76 (m, 1H), 6.84–6.86 (m, 1H), 7.00–7.03 (m, 1H), 7.60 (d, 1H). Mass Spectrum: (MH$^+$)=480.1.

3-(1,3-benzodioxol-5-yl)-4-{2-[2-(5,6,7,8-tetrahydro-1,8-naphthyridin-2-yl)ethyl]-1,3-thiazol-4-yl}butanoic acid Yield=84%. $^1$H NMR (DMSO-d$_6$) δ 8.04 (s, 1H), 7.55 (d, 1H), 7.0 (s, 1H), 6.70 (d, 1H), 6.65 (d, 1H), 6.60 (m, 2H), 3.50–3.30 (m, 5H), 3.15 (m, 2H), 3.00–2.82 (m, 2H), 2.72 (t, 2H), 2.50 (m, 2H), 1.80 (m, 2H); Mass Spectrum: (M$^+$) =452.1.

Elemental Analysis Calculated for C$_{24}$H$_{25}$N$_3$O4S.2.0 HCl.2.5H$_2$O Expected C, 50.62; .H, 5.66; N, 7.38. Found C, 50.45; H, 5.73; N, 7.36.

Scheme 5

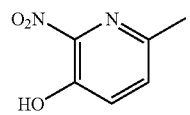 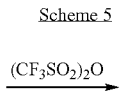

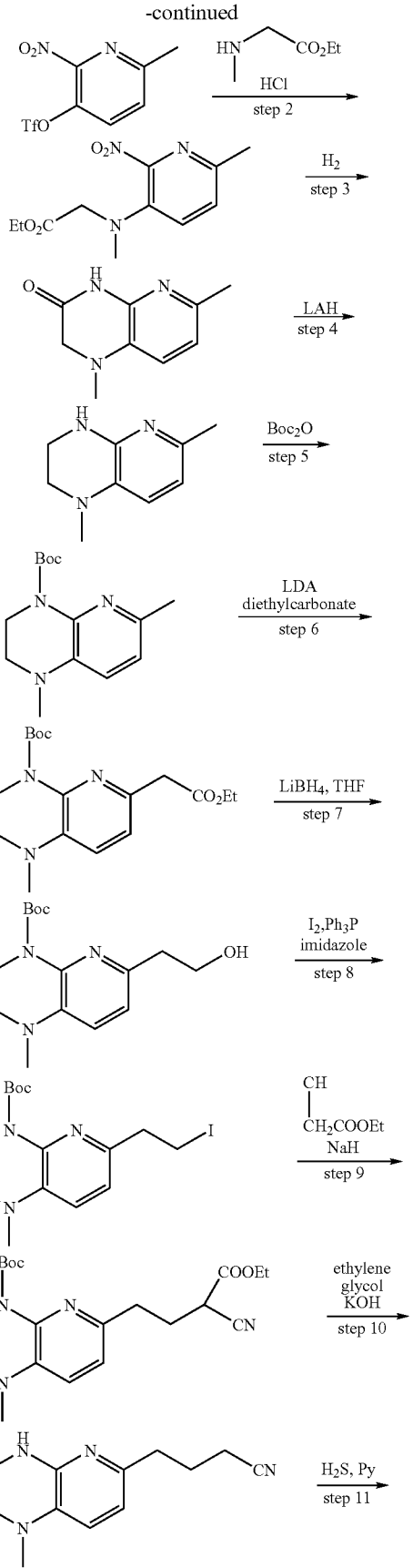

-continued

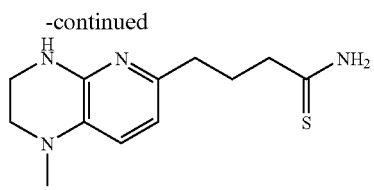

Procedures for Scheme 5

Step 1

6-Methyl-2-nitropyridin-3-yl trifluoromethanesulfonate

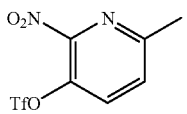

To a solution of 3-hydroxy-6-methyl-2-nitropyridine (2 g, 12.97 mmol, 1 eq) in $CH_2Cl_2$ (150 mL) at 0° C. under $N_2$ was added triethylamine (2.68 mL, 19.27 mmol, 1.48 eq) and followed by trifluoromethanesulfonic anhydride (2.62 mL, 15.57 mmol, 1.2 eq). The mixture was stirred for 2 hours at 0° C. and then quenched with water. The organic layer was separated, washed with water and dried over MgSO4. After filtration and concentration at reduced pressure, the crude mixture was purified by flash chromatography on silica gel (15% EA/Hex) to afford the desired product (3.65 g, 98% yield) as a yellow oil. H NMR (CDCl$_3$) δ 2.70 (s, 3H), 7.59 (d, 1H), 7.81 (d, 2H).

Step 2

Ethyl N-methyl-N-(6-methyl-2-nitropyridin-3-yl)glycinate

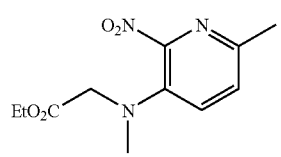

To a solution of 6-methyl-2-nitropyridin-3-yl trifluoromethanesulfonate (7.00 g, 24.47 mmol, 1 eq) in toluene (40 mL) at room temperature under $N_2$ was added sarcosine ester hydrochloride (9.4 g, 61.2 mmol, 2.5 eq) and followed by triethylamine (8.51 mL, 61.2 mmol, 2.5 eq). The mixture was refluxed overnight under $N_2$. The reaction was cooled to room temperature and quenched with water. The mixture was extracted three times with ethyl acetate and all organic extracts were combined, washed with brine, dried over $Na_2SO_4$. After filtration and concentration at reduced pressure, the crude mixture was purified by flash chromatography on silica gel (20% EA/Hex) to afford the desired product (4.3 g, 69% yield) as brown oil. H NMR (CDCl$_3$) δ 1.02 (t, 3H), 2.50 (s, 3H), 2.95 (s, 3H), 3.88 (s, 2H), 4.20 (q, 2H), 7.27 (d, 1H), 7.49(d, 2H).

Step 3

1,6-Dimethyl-1,4-dihydropyrido[2.3-b]pyrazin-3 (2H)-one

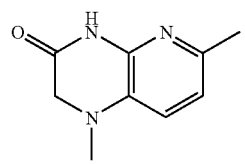

6-Methyl-2-nitropyridin-3-yl trifluoromethanesulfonate (4.3 g, 17 mmol) was hydrogenated in ethanol solution at room temperature using $H_2$ at 5 psi and 20% Pd(OH)$_2$/C catalyst for 2 hour. Upon completion of the reaction, the catalyst was filtered off and the filtrate was concentrated under reduced pressure. The product was crystallized out from 50% EA/Hex solution as yellow crystalline solid. The mother liquid was concentrated and purified by flash chromatography on silica gel (50% EA/Hex). (1.44 g, 46% yield) H NMR (CDCl$_3$) δ 2.26 (s, 3H), 2.70 (s, 3H), 3.18 (t, 2H), 3.58 (m, 2H), 6.34 (d, 1H), 6.57(d, 2H).

Step 4

1,6-Dimethyl-1,2,3,4-tetrahydropyrido[2,3-b]pyrazine

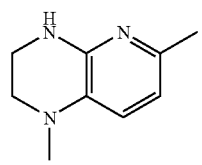

LiAlH$_4$ (214 mg, 5.64 mmol) was slowly added to 10 mL anhydrous THF in a round-bottom flask fitted with a stir bar and a condenser. After stirring for 10 minutes, a solution of 1,6-dimethyl-1,4-dihydropyrido[2,3-b]pyrazin-3(2H)-one (500 mg, 2.82 mmol) in 5 mL anhydrous THF was added drop wise. Upon completion of the addition, the reaction mixture was refluxed for 16 hours. The reaction was cooled to room temperature and quenched with 1 M NaOH solution until the mixture had become a milky yellow color. The precipitate was filtered off and washed 3 times with $CH_2Cl_2$. The filtrate and washings were combined, washed with brine, dried over MgSO$_4$. Filtered and concentrated under reduced pressure to give the desired product as light yellow oil, which solidified on standing. (420 mg, 91% yield). H NMR (CDCl$_3$) δ 2.27 (s, 3H), 2.80 (s, 3H), 3.17 (t, 2H), 3.58 (m, 2H), 6.36 (d, 1H), 6.56 (d, 2H).

Step 5

Tert-butyl 1,6-dimethyl-2,3-dihydropyrido[2,3-b]pyrazine-4(1H)-carboxylate

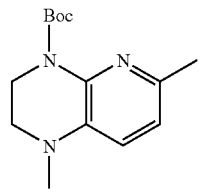

A solution of 1,6-dimethyl-1,2,3,4-tetrahydropyrido[2,3-b]pyrazine (1.14 g, 7 mmol), di-tert-butyl dicarbonate (2.29 g, 10.5 mmol), DMAP (100 mg) and triethylamine (1.46 mL, 10.5 mmol) in 30 mL THF was refluxed 72 hours under $N_2$. The reaction mixture was allowed to cool to room temperature and diluted with ethyl acetate. The mixture was washed with brine, dried over $Na_2SO_4$. After filtration and concentration at reduced pressure, the crude mixture was purified by flash chromatography on silica gel (40% EA/Hex) to afford the desired product (1.60 g, 90% yield) as yellow oil. H NMR (CDCl$_3$) δ 1.51 (s, 9H), 2.40 (s, 3H), 2.90 (s, 3H), 3.28 (t, 2H), 3.83 (m, 2H), 6.78 (d, 1H), 6.83(d, 2H).

Step 6

Tert-butyl 6-(2-ethoxy-2-oxoethyl)-1-methyl-2,3-dihydropyrido[2,3-b]pyrazine-4(1H)-carboxylate

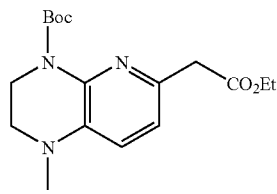

Lithium diisopropylamide solution (5 mL, 10 mmol, 2.0 M in THF/ethylbenzene/heptane) was added drop wise to a chilled (−78° C.), stirred solution of tert-butyl 1,6-dimethyl-2,3-dihydropyrido[2,3-b]pyrazine-4(1H)-carboxylate (950 mg, 3.61 mmol) and diethyl carbonate (1.62 mL, 13.36 mmol) in 20 mL dry THF under nitrogen atmosphere. After 1 hour the reaction was quenched with saturated $NH_4Cl$ solution and warmed to room temperature. The mixture was extracted three times with ethyl acetate and all organic extracts were combined, dried over $Na_2SO_4$, and concentrated under reduced pressure to get the crude product, which was purified by chromatography on silica gel (eluent: 30% ethyl acetate/hexane). The desired fractions were combined and concentrated under reduced pressure to get the desired product F (1.05 g, 87% yield) as a yellow solid. H NMR (CDCl$_3$) δ 1.25 (t, 3H), 1.50 (s, 9H), 2.78 (s, 3H), 3.38 (t, 2H), 3.68(s, 2H), 3.84 (t, 2H), 4.14 (q, 2H), 6.86 (d, 1H), 6.95(d, 2H).

Step 7

Tert-butyl 6-(2-hydroxyethyl)-1-methyl-2,3-dihydropyrido[2,3-b]pyrazine-4(1H)-carboxylate

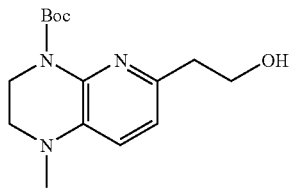

To a solution of tert-butyl 6-(2-ethoxy-2-oxoethyl)-1-methyl-2,3-dihydropyrido[2,3-b]pyrazine-4(1H)-carboxylate (26.5 g, 79.01 mmol)) in dry THF (50 mL) at room temperature was added, LiBH$_4$ (2.0 M in THF, 59.26 mL), and the resulting mixture was heated to reflux. After 16 hours the mixture was cooled to 0° C. and carefully quenched with water. The mixture was extracted three times with ethyl acetate. The combined organic extracts were dried over MgSO$_4$, filtered, and concentrated under reduced pressure to get the crude product, which was chromatographed on silica gel (eluent: (1:1) hexane/ethyl acetate) to afford the desired product (17.3 g, 74%) H NMR (CDCl$_3$) δ 1.55 (s, 9H), 2.73 (t, 2H), 2.80 (s, 3H), 3.30 (t, 2H), 3.78(t, 2H), 3.85 (t, 2H), 6.76 (d, 1H), 6.85 (d, 2H), 7.28 (s, 1H).

Step 8

Tert-butyl 6-(2-iodoethyl)-1-methyl-2,3-dihydropyrido[2.3-b]pyrazine-4(1H)-carboxylate

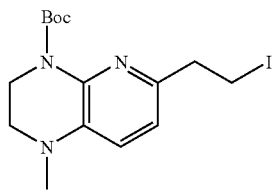

The mixture of tert-butyl 6-(2-hydroxyethyl)-1-methyl-2,3-dihydropyrido[2,3-b]pyrazine-4(1H)-carboxylate (5.6 g, 19.09 mmol), triphenylphosphine (6.51 g, 24.82 mmol), imidazole (1.82 g, 26.72 mmol), and a mixture of $CH_3CN$ and dry ether (1:1) was cooled to 0° C. Iodine (6.78 g, 26.72 mmol) was slowly added. The resulting mixture was stirred for 2 hour and then ether (150 mL) was added, washed successively with saturated aqueous $Na_2S_2O_3$ and brine, dried over $Na_2SO_4$ and concentrated under reduced pressure. The residue was purified by flash chromatography (silica, 20% EtOAC/Hex) to afford a yellow solid (6.6 g, 86% yield). H NMR (CDCl$_3$) δ 1.55 (s, 9H), 2.93 (s, 3H), 3.18 (t, 2H), 3.30 (t, 2H), 3.458(t, 2H), 3.85 (t, 2H), 6.85(q, 2H). LC-MS (M+H) 404.

Step 9

Tert-butyl 6-(3-cyano-4-ethoxy-4-oxobutyl)-1-methyl-2,3-dihydropyrido[2,3-b]pyrazine-4(1H)-carboxylate

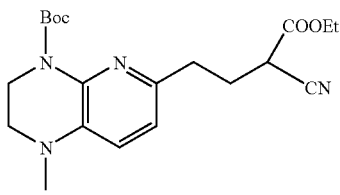

NaH (620 mg, 24.55 mmol) was suspended in DMF (203 mL) at 0° C. under $N_2$. Ethyl cyanoacetate (2.6 mL, 24.55 mmol) was added and the resulting mixture stirred for 30 min at 0° C. Tert-butyl 6-(2-iodoethyl)-1-methyl-2,3-dihydropyrido[2,3-b]pyrazine-4(1H)-carboxylate (6.6 g, 16.37 mmol) in DMF (10 mL) was introduced to the reaction mixture and stirred for 2 hours at room temperature. The mixture was cooled to 0 and quenched with water and extracted with EtOAc (3×). The organic layers were washed with brine, dried over $Na_2SO_4$ and concentrated in vacuo. The residue was purified by flash chromatography (silica, 90% EtOAC/Hex) to afford colorless oil (5.78 g, 91% yield). H NMR (CDCl$_3$) δ 1.35 (q, 3H), 1.55 (s, 9H), 2.38 (m, 2H), 2.89 (t, 2H), 2.93 (s, 3H), 3.32 (t, 2H), 3.85 (t, 2H), 3.90(m, 1H), 4.30 (q, 2H), 6.85(d, 2H). LC-MS (M+H) 389.

Step 10

4-(1-Methyl-1,2,3,4-tetrahydropyrido[2,3-b]pyrazin-6-yl)butanenitrile

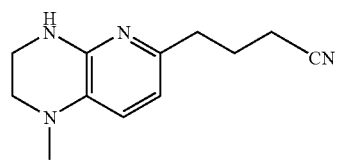

A mixture of tert-butyl 6-(3-cyano-4-ethoxy-4-oxobutyl)-1-methyl-2,3-dihydropyrido[2,3-b]pyrazine-4(1H)-carboxylate (5.78 g, 14.88 mmol) and KOH (powder, 1.25 g, 22.32 mmol) in ethylene glycol (30 mL) under $N_2$ was heated at 150° C. for 3 hours. The mixture was cooled to 0° C. and portioned between water and EtOAc. The organic phase was washed with brine, dried over $Na_2SO_4$ and concentrated in vacuo. Flash chromatography (silica, 100% EtOAc) yielded a colorless oil (2.2 g, 66% yield). H NMR (CDCl$_3$) δ 2.00 (t, 2H), 2.32 (t, 2H), 2.63 (t, 23H), 2.32 (s, 3H), 3.20 (t, 2H), 3.56 (t, 2H), 6.40 (d, 12H), 6.58(d, 1H), 4.20 (t, 2H), 6.41 (d, 1H), 6.89 (d, 1H).

Step 11

4-(1-Methyl-1,2,3,4-tetrahydropyrido[2,3-b]pyrazin-6-yl)propanethioamide

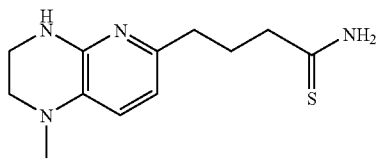

A mixture of 4-(1-methyl-1,2,3,4-tetrahydropyrido[2,3-b]pyrazin-6-yl)butanenitrile (0.76 g, 3.51 mmol), triethylamine (0.05 ml), and pyridine (15 mL) was loaded to a pressure tube. $H_2S$ gas was charged into the tube for 5 minutes. The tube was sealed for two weeks. The reaction solution was concentrated in vacuo to give a crude product that was carried to next step without further purification. LC-MS (M+H) 251.

Example 19

3-(1,3-Benzodioxol-5-yl)-4-{2-[3-(1-methyl-1,2,3,4-tetrahydropyrido[2,3-b]pyrazin-6-yl)propyl]-1,3-thiazol-4-yl}butanoic acid

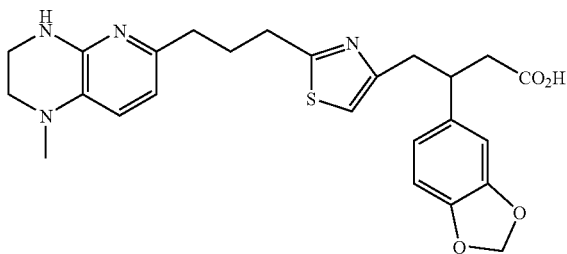

The mixture of 4-(1-methyl-1,2,3,4-tetrahydropyrido[2,3-b]pyrazin-6-yl) propanethioamide, (Scheme 5, Step 11), (0.10 g, 0.40 mmole), ethyl 3-(1,3-benzodioxol-5-yl)-6-chloro-5-oxohexanoate, Scheme 2, Example F, (0.13 g, 0.44 mmole) and dioxane (20 mL) was heated to reflux for 7 hours. The reaction solution was concentrated and the residue was purified on HPLC using water/acetonitrile gradient 5–50% in 30 min to give ethyl ester intermediate. The intermediate was stirred in 1 N NaOH in ethanol (15 ml) overnight. Solvent was removed and the residue was purified on HPLC using water/acetonitrile gradient 5–50% in 30 min to yield 38 mg desired product (19% yield). $^1$H NMR (CD$_3$OD) δ 2.05 (m, 2H), 2.50–2.70 (m, 4H), 2.95 (s, 3H), 3.00–3.15 (m, 4H), 3.30 (m, 2H), 3.50 (m, 1H), 3.65 (t, 2H), 5.90 (s, 2H), 6.59–6.65 (m, 4H), 6.90–6.94 (m, 2H). FAB-MS:(MH+)=481

Elemental Analysis: Calcd. for $C_{25}H_{28}N_4O_4S.3.5$ TFA: Expected C, 43.69; H, 3.61; N, 6.37. Found: C, 43.85; H, 3.87; N, 6.13.

Example 20

3-(6-Methoxypyridin-3-yl)-4-{2-[3-(1-methyl-1,2,3,4-tetrahydropyrido[2,3-b]pyrazin-6-yl)propyl]-1,3-thiazol-4-yl}butanoic acid

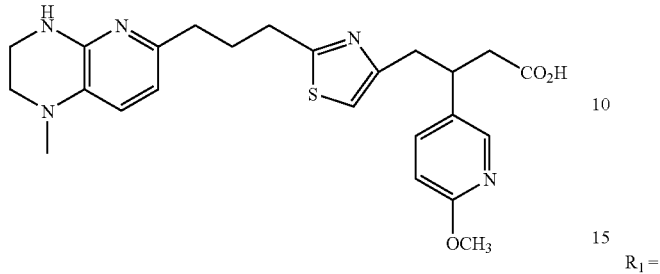

The mixture 4-(1-methyl-1,2,3,4-tetrahydropyrido[2,3-b]pyrazin-6-yl) propanethioamide, (Scheme 5, Step 11), (364 mg, 1.45 mmol), and ethyl 6-chloro-3-(6-methoxypyridin-3-yl)-5-oxohexanoate, Scheme 2, Example L (480 mg, 1.60 mmole) and dioxane (20 mL) was heated to reflux for 7 hours. The reaction solution was concentrated and the residue was purified on reverse phase HPLC using water/acetonitrile gradient 20–90% in 30 min to give acetate intermediate. The intermediate was stirred in 1 N NaOH in ethanol (15 mL) overnight. Solvent was removed and the residue was purified on reverse phase HPLC using water/acetonitrile gradient 10–50% in 30 min to yield 60 mg desired product (9% yield). $^1$H NMR (CD$_3$CN) δ 2.05 (m, 2H), 2.60 (m, 2H), 2.75 (m, 2H), 2.90(s, 3H), 3.08–3.26 (m, 4H), 3.43 (t, 2H), 3.58 (m, 1H), 3.60 (t, 2H), 3.90 (s, 3H), 6.50 (d, 1H), 6.80 (d, 1H), 6.95 (d, 1H), 7.05 (s, 1H), 7.84 (m, 1H), 7.95 (d, 1H). FAB-MS:(MH+)=468

Elemental Analysis: Calcd. for C$_{24}$H$_{29}$N$_5$O$_3$S.4.8 TFA. 3.0H$_2$O: Expected C, 37.75; H, 3.75; N, 6.55. Found: C, 37.44; H, 3.41; N, 6.21.

Scheme 6

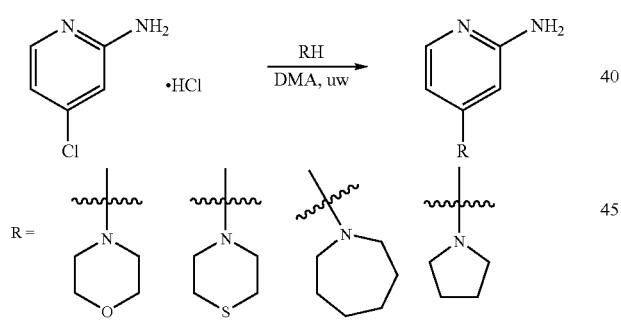

Procedure for Scheme 6

4-chloropyridin-2-amine

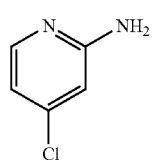

4-chloropyridin-2-amine was synthesized according to procedures outlined in Sundberg, Richard; Jiang, Songchun; Organic Preparation and Procedure; 29 (1), 1997, 117–122.

Example 1

4-morpholin-4-ylpyridin-2-amine

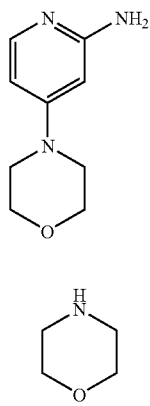

$R_1 =$ 4-chloropyridin-2-amine (800 mg, 6.22 mmol) was combined with morpholine (8.0 mL) in 2 mL DMA in a sealed vessel. This mixture was heated in the microwave (CSA Discover) for 5 minutes at 200° C. Upon cooling, the reaction was concentrated in vacuo and purified via silica gel chromatography (eluent: 95/5/0.5 CH$_2$Cl$_2$/MeOH/NH$_4$OH) to give 837 mg of the product as a yellow solid. Yield: 75%.

$^1$H NMR (DMSO-d$_6$) δ 7.70–7.64 (m, 1H), 6.59–6.54 (m, 1H), 6.05–6.00 (m, 1H), 3.74–3.65 (m, 4H), 3.45–3.37 (m, 4H).

Mass Spectral Data Calculated Mass: 179.20 Found Mass: 180.11 (for MH$^+$).

Elemental Analysis Calculated for C$_9$H$_{13}$N$_3$O$_1$.0.1 H$_2$O C, 59.72; H, 7.35; N, 23.21. Found C, 59.66; H, 7.25; N, 23.20.

Example 2

4-thiomorpholin-4-ylpyridin-2-amine

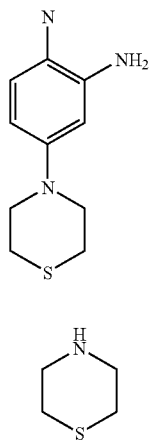

$R =$

This compound was prepared according to the method described in SCHEME 6, EXAMPLE 1, using the appropriate amine, thiomorpholine. Yield: 47% H NMR (DMSO-d$_6$) δ 7.61–7.55 (m, 1H), 6.12–6.06 (m, 1H), 5.84–5.78 (m, 1H), 3.86–3.80 (m, 2H), 3.65–3.57 (m, 4H), 2.60–2.53 (m, 4H).

Mass Spectral Data Calculated Mass: 195.29 Found Mass: 196.09 (for MH$^+$).

Elemental Analysis Calculated for C$_9$H$_{13}$N$_3$S.0.2 H$_2$O C, 54.35; H, 6.79; N, 21.13. Found C, 54.51; H, 6.78; N, 20.99.

Example 3

4-Azepan-1-ylpyridin-2-amine

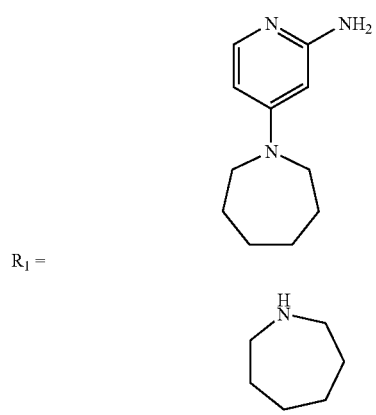

R$_1$ =

This compound was prepared according to the method described in SCHEME 6, EXAMPLE 1, using the appropriate amine, Hexamethyleneimine. Yield: 40% $^1$H NMR (DMSO-d$_6$) δ 7.53–7.49 (m, 1H), 5.95–5.90 (m, 1H), 5.67–5.63 (m, 1H), 3.40–3.30 (m, 8H), 1.73–1.64 (m, 4H), 1.48–1.42 (m, 4H).

Example 4

4-Pyrrolidin-1-ylpyridin-2-amine

R =

This compound was prepared according to the method described in SCHEME 6, EXAMPLE 1, using the appropriate amine, pyrrolidine. Yield: 77% $^1$H NMR (DMSO-d$_6$) δ 7.54–7.49 (m, 1H), 5.84–5.79 (m, 1H), 5.52–5.48 (m, 1H), 3.22–3.15 (m, 4H), 1.95–1.85 (m, 4H).

Mass Spectral Data Calculated Mass: 163.22 Found Mass: 164.12 (for MH$^+$).

Elemental Analysis Calculated for C$_9$H$_{13}$N$_3$.0.3 H$_2$O C, 64.11; H, 8.13; N, 24.92. Found C, 63.98; H, 7.70; N, 24.68.

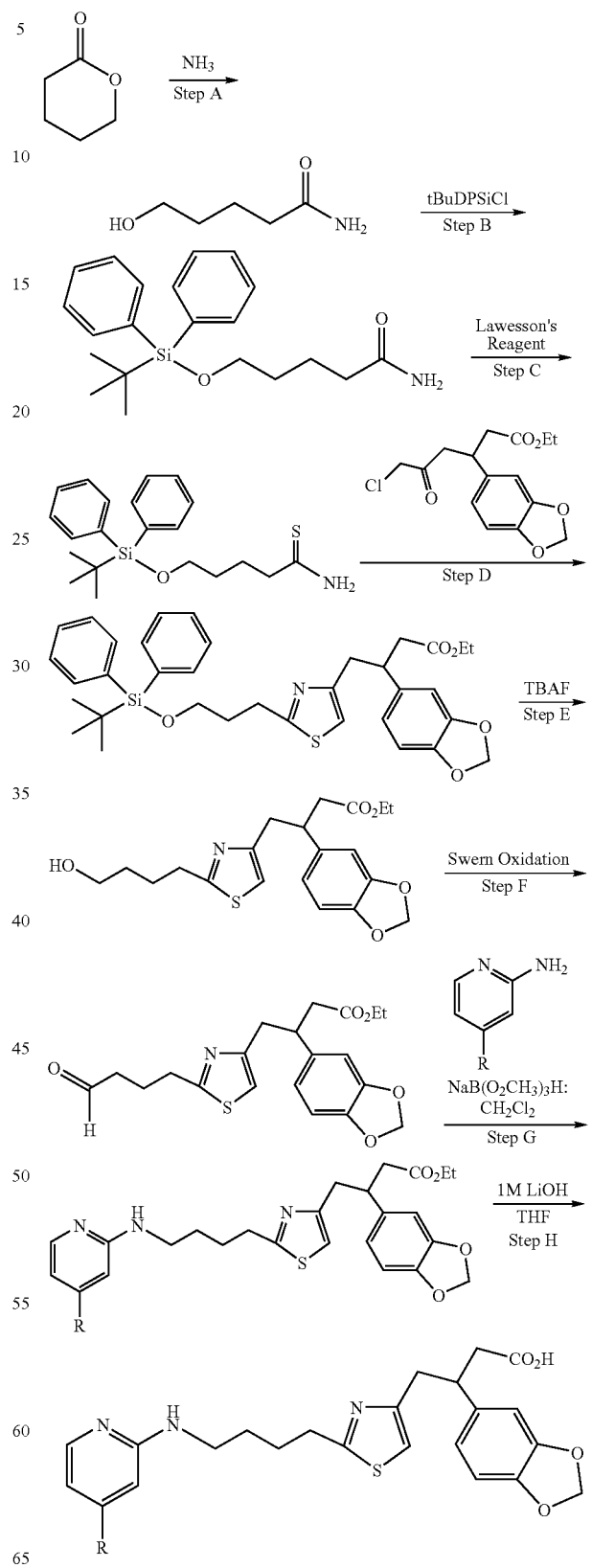

Scheme 7

Procedures for Scheme 7

Step A

5-Hydroxypentanamide

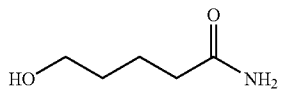

Tetrahydro-2H-pyran-2-one (20 g) was dissolved in EtOH (50 mL) and placed in a sealed bomb. An excess of ammonia (gas) was charged into the bomb. The bomb was heated to 80° C. for 6 hrs at 250 psi. Upon concentration in vacuo, the crude white solid was filtered and dried to obtain 15.76 g. Yield: 67% $^1$H NMR (DMSO-$d_6$) δ 7.2 (br s, 1H), 6.65 (br s, 1H), 4.35 (t, 1H), 3.38 (q, 2H), 2.04 (t, 2H), 1.5 (p, 2H), 1.4 (p, 2H);

Step B

5-{[Tert-butyl(diphenyl)silyl]oxy}pentanamide

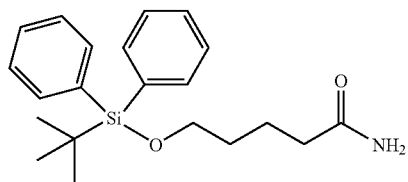

5-Hydroxypentanamide (5.0 g, 42.7 mmol) was dissolved in DMF (50 mL). TBDPSi—Cl (13.74 g, 50.0 mmol) and imidazole (3.40 g, 50.0 mmol) was added, and the reaction was stirred for 48 hrs at ambient temperature. The reaction was concentrated in vacuo, and the residue dissolved in ethyl acetate. The organics were washed with H$_2$O and brine, dried over MgSO4, filtered, and concentrated in vacuo, and purified via silica gel chromatography (eluent: 1:1 Hexane: Ethyl Acetate) to give the product as a white solid. Yield: 14.59 g (96%) $^1$H NMR (DMSO-$d_6$) δ 7.62 (m, 4H), 7.45 (m, 6H), 7.22 (br s, 1H), 6.68 (br s, 1H), 3.64 (t, 2H), 2.04 (t, 2H), 1.55 (m, 4H), 0.98 (s, 9H);

Step C

5-{[Tert-butyl(diphenyl)silyl]oxy}pentanethioamide

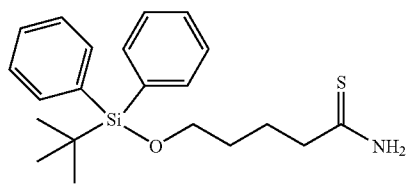

Lawesson's reagent (8.19 g, 20.25 mmol) was heated to reflux in benzene (100 mL) for 1 hr. Cool to just below reflux temperature, and add a solution of 5-{[tert-butyl(diphenyl) silyl]oxy}pentanamide (7.20 g, 20.25 mmol in 50 mL ben- zene). Stir at room temperature for 2 hrs. Concentrate in vacuo to a chunky oil and purified via silica gel chroma- tography (eluent: 9:1 Hexane:Ethyl Acetate) to give the product as a yellow-green oil. Yield: 6.50 g (62%) $^1$H NMR (DMSO-$d_6$) δ7.65–7.60 (m, 4H), 7.49–7.41 (m, 6H), 3.68–3.63 (t, 2H), 2.50–2.44 (t, 2H), 1.80–1.70 (m, 2H), 1.60–1.51 (m, 2H), 1.00 (s, 9H).

Step D (3S)-Ethyl 3-(1,3-benzodioxol-5-yl)-4-[2-(4-{[tert- butyl(diphenyl)silyl]oxy}butyl)-1,3-thiazol-4-yl] butanoate

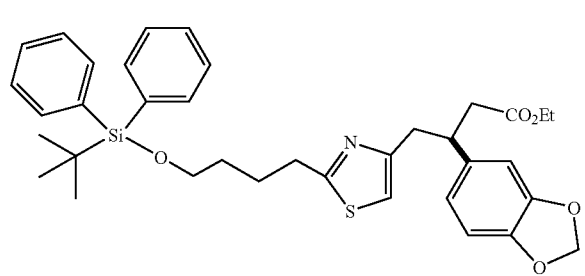

Dissolve 5-{[tert-butyl(diphenyl)silyl] oxy}pentanethioamide (4.97 g, 13.37 mmol) in 1,4-dioxane (50 mL). Add magnesium carbonate hydroxide pentahydrate (3.25 g, 0.5 mmol) and (3S)-ethyl 3-(1,3-benzodioxol-5-yl)- 6-chloro-5-oxohexanoate (see Scheme 2, Example M) (4.18 g, 13.37 mmol). Heat to 60° C. for 5 hrs. Upon cooling, the reaction was filtered through a pad of celite and concentrated in vacuo, and purified via silica gel chromatography (eluent: 9:1 Hexane:Ethyl Acetate) to give the product as a yellow oil. Yield: 6.55 g (78%) $^1$H NMR (DMSO-$d_6$) δ7.64–7.58 (m, 4H), 7.48–7.39 (m, 6H), 6.95–6.93 (m, 1H), 6.85–6.82 (m, 1H), 6.73–6.69 (m, 1H), 5.92 (s, 2H), 3.93–3.85 (q, 2H), 3.70–3.64 (t, 2H), 3.46–3.38 (m, 1H), 3.00–2.85 (m, 4H), 2.68–2.53 (m, 2H), 1.83–1.74 (m, 2H), 1.62–1.53 (m, 2H), 1.08–0.99 (t, 3H), 0.99 (s, 9H).

Step E (3S)-Ethyl 3-(1,3-benzodioxol-5-yl)-4-[2-(4-hy- droxybutyl)-1,3-thiazol-4-yl]butanoate

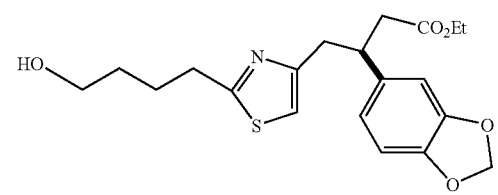

(3S)-Ethyl 3-(1,3-benzodioxol-5-yl)-4-[2-(4-{[tert-butyl (diphenyl)silyl]oxy}butyl)-1,3-thiazol-4-yl]butanoate 6.55 g, 10.39 mmol) was dissolved in THF (20 mL) and tetrabutyl ammonium fluoride (1M, 23.39 mL, 23.39 mmol) was added. The reaction was stirred at ambient temperature for 2 hours. Dilute with diethyl ether, and wash with water and brine. The organic layer was dried over MgSO4, filtered, and concentrated in vacuo and purified via silica gel chroma- tography (eluent: 4:1 Hexane:Ethyl Acetate) to give the product as a colorless oil. Yield: 3.08g (76%) $^1$H NMR (DMSO-$d_6$) δ6.95–6.92 (m, 1H), 6.85–6.83 (m, 1H), 6.75–6.71 (m, 1H), 6.63–6.59 (m, 1H), 5.94 (s, 2H), 3.95–3.85 (q, 2H), 3.46–3.38 (m, 3H), 2.98–2.85 (m, 4H), 2.68–2.51 (m, 2H), 1.75–1.65 (m, 2H), 1.50–1.41 (m, 2H), 1.08–1.02 (t, 3H).

Step F (3S)-Ethyl 3-(1,3-benzodioxol-5-yl)-4-[2-(4-oxobutyl)-1,3-thiazol-4-yl]butanoate

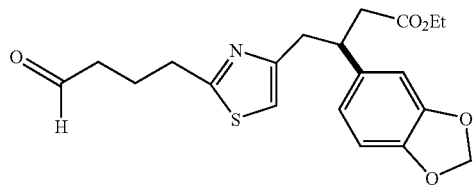

Dimethyl sulfoxide (1.47 mL, 3.15 mmol) was cooled in 5 mL CH$_2$Cl$_2$ to –70° C. for 10 min. The oxalyl chloride (2.0M in CH$_2$Cl$_2$, 4.9 mL, 9.85 mmol) was added, and the reaction was allowed to stir at –70° C. for 1 hr. A solution of (3S)-Ethyl 3-(1,3-benzodioxol-5-yl)-4-[2-(4-hydroxybutyl)-1,3-thiazol-4-yl]butanoate (2.57 g, 6.56 mmol) in CH$_2$Cl$_2$ (5 mL) was added to the reaction and stirred at –70° C. for 1 hr. Add triethylamine (5.96 mL, 6.52 mmol) and allow to warm to room temperature. Dilute with ethyl acetate, wash with water, 1 N HCl, water, and brine. The organic layer was dried over MgSO4, filtered, and concentrated in vacuo and purified via silica gel chromatography (eluent: 3:1 Hexane:Ethyl Acetate) to give the product as a colorless oil. Yield: 1.95g (76%) $^1$H NMR (DMSO-$d_6$) δ9.68–9.65 (m, 1H), 6.98–6.95 (m, 1H), 6.75–6.71 (m, 1H), 6.63–6.58 (m, 1H), 5.94 (s, 2H), 3.96–3.88 (q, 2H), 3.47–3.38 (m, 1H), 3.00–2.85 (m, 4H), 2.68–2.48 (m, 4H), 1.97–1.88 (m, 2H), 1.08–1.01 (t, 3H).

Example 1

Step G (3S)-Ethyl 3-(1,3-benzodioxol-5-yl)-4-(2-{4-[(4-morpholin-4-ylpyridin-2-yl)amino]butyl}-1,3-thiazol-4-yl)butanoate hydrochloride

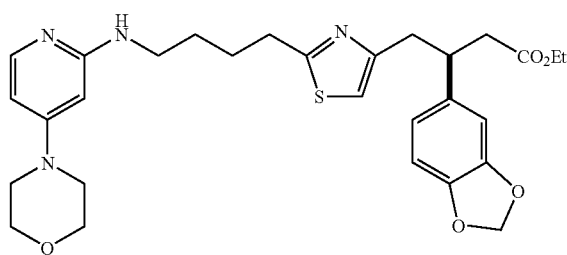

Dissolve (3S)-Ethyl 3-(1,3-benzodioxol-5-yl)-4-[2-(4-oxobutyl)-1,3-thiazol-4-yl]butanoate (230 mg, 0.6 mmol) and 4-morpholin-4-ylpyridin-2-amine (88 mg, 0.5 mmol) prepared according to Scheme 6, Example 1, in CH$_2$Cl$_2$. Add 3 mL THF and add NaBH(OAc)$_3$. Stir at room temperature for 18 hours. Add 1.0 eq NaBH(OAc)$_3$ and stir 24 hrs. The reaction was concentrated in vacuo and purified via reverse phase HPLC using a gradient of 10–60% CH$_3$CN/H$_2$O/0.5% HCl over 30 minutes to obtain the crude desired product.

LC/MS Data Calculated Mass: 552.69 Found Mass: 553.20 (for MH$^+$).

Step H (3S)-3-(1,3-benzodioxol-5-yl)-4-(2-{4-[(4-morpholin-4-ylpyridin-2-yl)amino]butyl}-1,3-thiazol-4-yl)butanoic acid hydrochloride

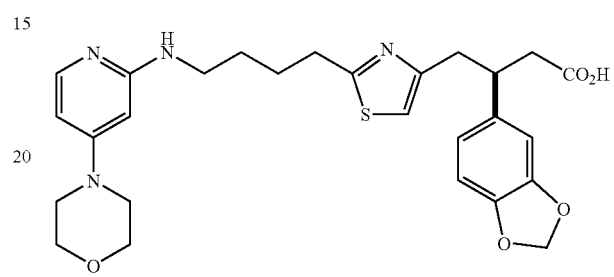

(3S)-Ethyl 3-(1,3-benzodioxol-5-yl)-4-(2-{4-[(4-morpholin-4-ylpyridin-2-yl)amino]butyl}-1,3-thiazol-4-yl)butanoate hydrochloride (0.50 mmol) was dissolved in THF (2 mL) at 0° C. 1M LiOH (2.5 mL) was added, and the reaction was warmed to room temperature and stirred for 20 hours. The reaction was acidified to pH=1 with conc. HCl and concentrated in vacuo. The residue was purified via reverse phase HPLC using a gradient of 5–50% CH$_3$CN/H$_2$O/0.5% HCl over 30 minutes to obtain the desired product. Yield: 83 mg, 28% over 2 steps. $^1$H NMR (DMSO-$d_6$) δ7.63–7.68 (m, 1H), 7.01–7.04 (m, 1H), 6.85–6.82 (m, 1H), 6.75–6.71 (m, 1H), 6.65–6.59 (m, 1H), 6.59–6.54 (m, 1H), 6.03–5.98 (m, 1H), 5.97 (s, 2H), 3.73–3.66 (m, 4H), 3.52–3.45 (m, 4H), 3.50–3.38 (m, 5H), 3.33–3.25 (m, 2H), 3.06–2.87 (m, 4H), 2.62–2.46 (m, 2H), 1.84–1.73 (m, 2H), 1.65–1.55 (m, 2H).

Mass Spectral Data Calculated Mass: 524.63 Found Mass: 525.22 (for MH$^+$).

Elemental Analysis Calculated for $C_{27}H_{32}N_4O_5S \cdot 2.2$ HCl,$\cdot 3.1$ H$_2$O C, 49.63; H, 6.20; N, 8.57. Found C, 49.41; H, 6.29; N, 8.47.

Example 2

(3S)-3-(1,3-benzodioxol-5-yl)-4-(2-{4-[(4-pyrrolidin-1-ylpyridin-2-yl)amino]butyl}-1,3-thiazol-4-yl)butanoic acid hydrochloride

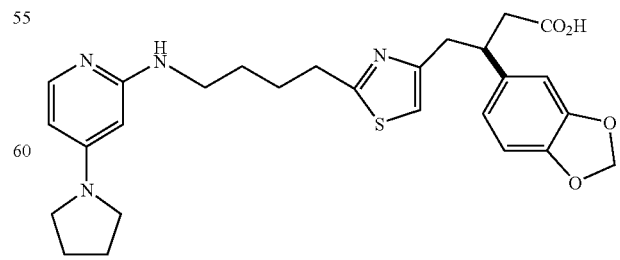

The title compound was prepared according to the method described in SCHEME 7, EXAMPLE 1, using 4-pyrrolidin- 1-ylpyridin-2-amine (Scheme 6, Example 4) for Step G. Yield: 17% over 2 steps. $^1$H NMR (DMSO-d$_6$) δ7.64–7.57 (m, 1H), 7.17–7.11 (m, 1H), 6.88–6.85 (m, 1H), 6.77–6.73 (m, 1H), 6.66–6.61 (m, 1H), 6.27–6.20 (m, 1H), 5.94 (s, 2H), 5.65–5.62 (m, 1H), 3.52–3.39 (m, 4H), 3.36–3.23 (m, 5H), 3.14–2.92 (m, 4H), 2.63–2.48 (m, 2H), 2.00–1.93 (m, 4H), 1.87–1.75 (m, 2H), 1.65–1.55 (m, 2H).

Mass Spectral Data Calculated Mass: 508.63 Found Mass: 509.24 (for MH$^+$).

Elemental Analysis Calculated for C$_{27}$H$_{32}$N$_4$O$_4$S.3.0 HCl,.3.1 H$_2$O C, 50.27; H, 5.94; N, 8.69. Found C, 50.13; H, 6.09; N, 8.61.

Example 3

(3S)-3-(1,3-benzodioxol-5-yl)-4-(2-{4-[(4-thiomorpholin-4-ylpyridin-2-yl)amino]butyl}-1,3-thiazol-4-yl)butanoic acid hydrochloride The title compound was prepared according to the method described in SCHEME 7, EXAMPLE 1, using 4-thiomorpholin-4-ylpyridin-2-amine (Scheme 6, Example 2) for Step G. Yield: 40% over 2 steps. $^1$H NMR (DMSO-d$_6$) δ7.66–7.60 (m, 1H), 7.06–7.03 (m, 1H), 6.86–6.82 (m, 1H), 6.75–6.73 (m, 1H), 6.65–6.60 (m, 1H), 6.59–6.54 (m, 1H), 6.02–5.98 (m, 1H), 5.94 (s, 2H), 3.91–3.84 (m, 4H), 3.48–3.39 (m, 1H), 3.34–3.25 (m, 2H), 3.09–2.89 (m, 4H), 2.70–2.63 (m, 4H), 2.61–2.48 (m, 2H), 1.85–1.75 (m, 2H), 1.65–1.55 (m, 2H).

Mass Spectral Data Calculated Mass: 540.70 Found Mass: 541.22 (for MH$^+$).

Elemental Analysis Calculated for C$_{27}$H$_{32}$N$_4$O$_4$S$_2$.2.0 HCl,.2.0 H$_2$O C, 49.92; H, 5.90; N, 8.62. Found C, 49.94; H, 6.24; N, 8.60.

Scheme 8

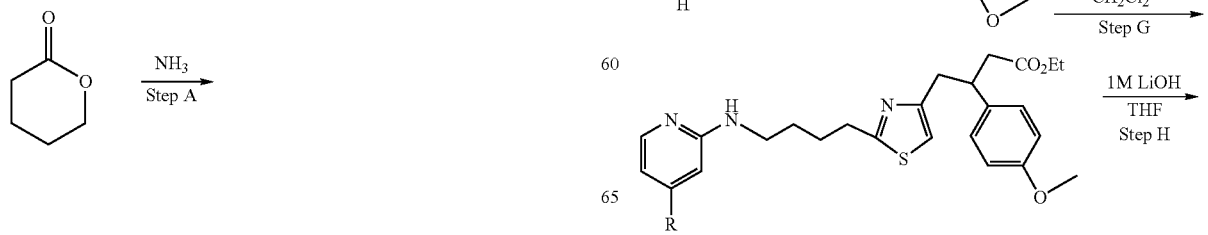

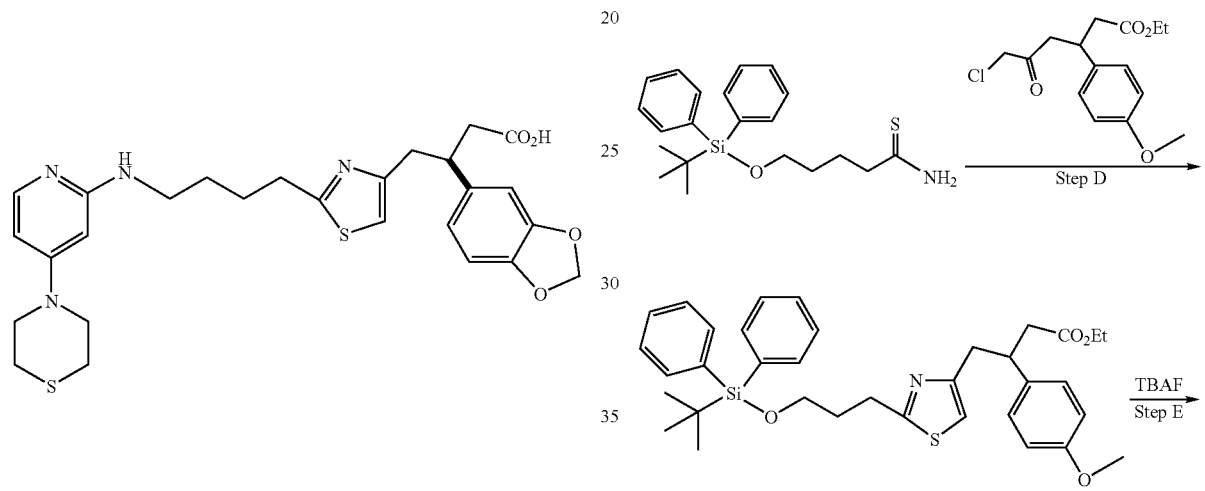

-continued

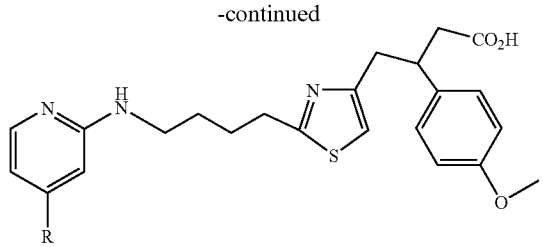

Procedures for Scheme 8

Step D

Ethyl 4-[2-(4-{[tert-butyl(diphenyl)silyl]oxy}butyl)-1,3-thiazol-4-yl]-3-(6-methoxypyridin-3-yl)butanoate

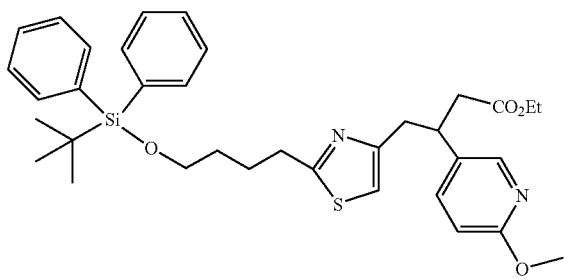

The title compound was prepared according to the method described in SCHEME 7, EXAMPLE 1, Step D, using ethyl 6-chloro-3-(6-methoxypyridin-3-yl)-5-oxohexanoate in SCHEME 2, Step L. Yield: 67% $^1$H NMR (DMSO-$d_6$) δ7.92–7.88 (m, 1H), 7.65–7.55 (m, 5H), 7.48–7.39 (m, 6H), 6.96–6.94 (m, 1H), 6.70–6.65 (m, 1H), 3.95–3.87 (q, 2H), 3.75 (s, 3H), 3.70–3.64 (t, 2H), 3.51–3.45 (m, 1H), 3.05–2.86 (m, 4H), 2.75–2.55 (m, 2H), 1.82–1.72 (m, 2H), 1.60–1.52 (m, 2H), 1.05–0.99 (t, 3H), 0.99 (s, 9H).

Step E

Ethyl 4-[2-(4-hydroxybutyl)-1,3-thiazol-4-yl]-3-(6-methoxypyridin-3-yl)butanoate

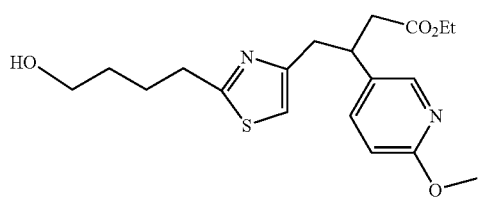

The title compound was prepared according to the method described in SCHEME 7, EXAMPLE 1, Step E. Yield: 97% $^1$H NMR (DMSO-$d_6$) δ7.92–7.89 (m, 1H), 7.61–7.56 (m, 1H), 6.96–6.94 (m, 1H), 6.72–6.67 (m, 1H), 4.45–4.40 (t, 1H), 3.96–3.89 (q, 2H), 3.77 (s, 3H), 3.51–3.30 (m, 3H), 3.05–2.88 (m, 4H), 2.75–2.57 (m, 2H), 1.75–1.63 (m, 2H), 1.50–1.40 (m, 2H), 1.07–1.02 (t, 3H).

Step F

Ethyl 3-(6-methoxypyridin-3-yl)-4-[2-(4-oxobutyl)-1,3-thiazol-4-yl]butanoate

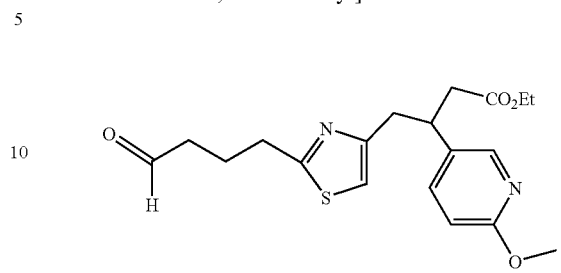

The title compound was prepared according to the method described in SCHEME 8, EXAMPLE 1, Step F. Yield: 76% $^1$H NMR (DMSO-$d_6$) δ7.92–7.89 (m, 1H), 7.61–7.56 (m, 1H), 7.00–6.97 (m, 1H), 6.73–6.68 (m, 1H), 3.96–3.88 (q, 2H), 3.77 (s, 3H), 3.52–3.42 (m, 1H), 3.05–2.89 (m, 4H), 2.75–2.57 (m, 2H), 2.52–2.46 (m, 2H), 1.95–1.86 (m, 2H), 1.06–1.01 9t, 3H).

Example 1

3-(6-Methoxypyridin-3-yl)-4-(2-{4-[(4-morpholin-4-ylpyridin-2-yl)amino]butyl}-1,3-thiazol-4-yl)butanoic acid hydrochloride

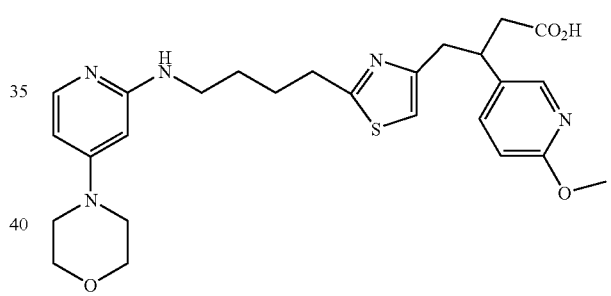

Step G

Dissolve ethyl 3-(6-methoxypyridin-3-yl)-4-[2-(4-oxobutyl)-1,3-thiazol-4-yl]butanoate (374mg, 1.0 mmol) and 4-morpholin-4-ylpyridin-2-amine (150 mg, 0.836 mmol) prepared according to Scheme 6, Example 1, in CH$_2$Cl$_2$. Add NaBH(OAc)$_3$ (251 mg, 1.12 mmol) and stir at room temperature for 18 hours. The reaction was concentrated in vacuo and purified via reverse phase HPLC using a gradient of 10–60% CH$_3$CN/H$_2$O/0.5% HCl over 30 minutes to obtain the crude desired product.

Step H

The crude ester was dissolved in THF (3mL) at 0° C. 1M LiOH (4 mL) was added, and the reaction was allowed to stir for 18 hrs. The reaction was concentrated in vacuo and purified via reverse phase HPLC using a gradient of 10–60% CH$_3$CN/H$_2$O/0.5% HCl over 30 minutes to obtain desired product. Yield: 130 mgs, 24% over2 steps. $^1$H NMR (DMSO-$d_6$) δ8.00–7.98 (m, 1H), 7.78–7.72 (m, 1H), 7.68–7.62 (m, 1H), 7.18–7.15 (m, 1H), 6.88–6.82 (m, 1H), 6.60–6.55 (m, 1H), 6.07–6.03 (m, 1H), 3.82 (s, 3H), 3.73–3.65 (m, 4H), 3.59–3.48 (m, 1H), 3.51–3.45 (m, 4H), 3.14–2.95 (m, 4H), 2.73–2.56 (m, 2H), 1.85–1.75 (m, 2H), 1.65–1.55 (m, 2H).

Mass Spectral Data Calculated Mass: 511.64 Found Mass: 512.00 (for MH$^+$).

Elemental Analysis Calculated for $C_{26}H_{33}N_5O_4S.3.0$ HCl,.2.0 H$_2$O C, 47.53; H, 6.14; N, 10.66. Found C, 47.63; H, 6.25; N, 10.56.

Example 2

3-(6-methoxypyridin-3-yl)-4-(2-{4-[(4-thiomorpholin-4-ylpyridin-2-yl)amino]butyl}-1,3-thiazol-4-yl)butanoic acid hydrochloride

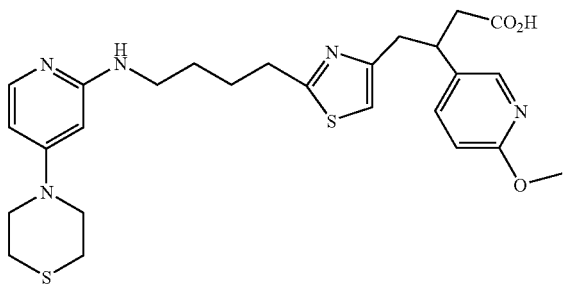

The title compound was prepared according to the method described in SCHEME 8, EXAMPLE 1, using 4-thiomorpholin-4-ylpyridin-2-amine (Scheme 6, Example 2) for Step G. Yield: 28% over 2 steps. $^1$H NMR (DMSO-d$_6$) δ7.99–7.95 (m, 1H), 7.77–7.71 (m, 1H), 7.63–7.55 (m, 1H), 7.18–7.15 (m, 1H), 6.87–6.81 (m, 1H), 6.55–6.50 (m, 1H), 6.02–5.97 (m, 1H), 3.87–3.82 (m, 4H), 3.80 (s, 3H), 3.55–3.45 (m, 1H), 3.11–2.95 (m, 4H), 2.68–2.52 (m, 6H), 1.33–1.22 (m, 2H), 1.60–1.51 (m, 2H).

Mass Spectral Data Calculated Mass: 527.70 Found Mass: 528.00 (for MH$^+$).

Elemental Analysis Calculated for $C_{26}H_{33}N_5O_3S_2.3.5$ HCl,.2.0 H$_2$O C, 44.02; H, 6.04; N, 9.87. Found C, 43.94; H, 6.34; N, 9.80.

Example 3

3-(6-Methoxypyridin-3-yl)-4-(2-{4-[(4-pyrrolidin-1-ylpyridin-2-yl)amino]butyl}-1,3-thiazol-4-yl)butanoic acid hydrochloride

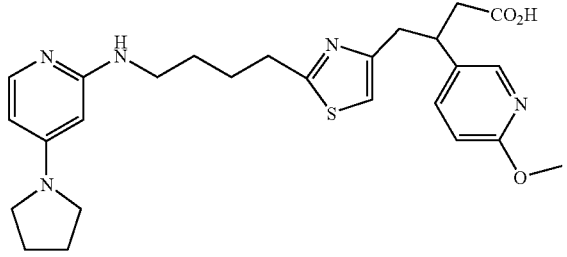

The title compound was prepared according to the method described in SCHEME 8, EXAMPLE 1, using 4-pyrrolidin-1-ylpyridin-2-amine (Scheme 6, Example 4) for Step G. Yield: 13% over 2 steps. $^1$H NMR (DMSO-d$_6$) δ7.99–7.95 (m, 1H), 7.72–7.65 (m, 1H), 7.63–7.58 (m, 1H), 7.11–7.08 (m, 1H), 6.84–6.78 (m, 1H), 6.28–6.21 (m, 1H), 5.66–5.59 (m, 1H), 3.81 (s, 3H), 3.55–3.46 (m, 1H), 3.46–3.37 (m, 2H), 3.32–3.22 (m, 4H), 3.11–2.92 (m, 4H), 2.70–2.52 (m, 2H), 2.02–1.92 (m, 4H), 1.85–1.75 (m, 2H), 1.65–1.55 (m, 2H).

Mass Spectral Data Calculated Mass: 495.64 Found Mass: 496 (for MH$^+$).

Elemental Analysis Calculated for $C_{26}H_{33}N_5O_3S.3.8$ HCl,.1.3 H$_2$O C, 47.49; H, 6.04; N, 10.65. Found C, 47.68; H, 6.40; N, 10.59.

Example 4

4-(2-{4-[(4-azepan-1-ylpyridin-2-yl)amino]butyl}-1,3-thiazol-4-yl)-3-(6-methoxypyridin-3-yl)butanoic acid hydrochloride

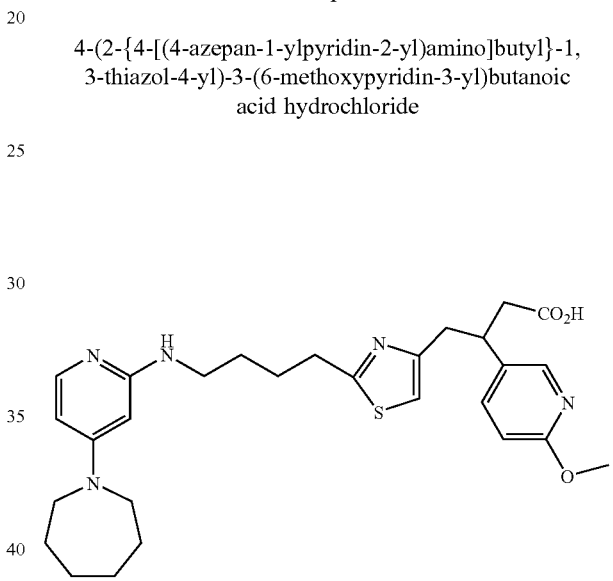

The title compound was prepared according to the method described in SCHEME 8, EXAMPLE 1, using 4-azepan-1-ylpyridin-2-amine (Scheme 6, Example 3) for Step G. Yield: 18% over 2 steps. $^1$H NMR (DMSO-d$_6$) δ8.04–8.00 (m, 1H), 7.83–7.78 (m, 1H), 7.60–7.54 (m 1H), 7.25–7.22 (m, 1H), 6.93–6.87 (m, 1H), 6.43–6.38 (m, 1H), 5.88–5.82 (m, 1H), 3.84 (s, 3H), 3.61–3.50 (m, 5H), 3.34–3.24 (m, 2H), 3.15–2.99 (m, 4H), 2.72–2.57 (m, 2H), 1.86–1.76 (m, 2H), 1.76–1.64 (m, 4H), 1.63–1.53 (m, 2H), 1.50–1.43 (m, 4H).

Mass Spectral Data Calculated Mass: 523.69 Found Mass: 524 (for MH$^+$).

Elemental Analysis Calculated for $C_{28}H_{37}N_6O_3S.3.0$ HCl,.1.7 H$_2$O C, 50.67; H, 6.59; N, 10.55. Found C, 50.70; H, 6.89; N, 10.47.

Select examples of $\alpha_v\beta_3$ and/or $\alpha_v\beta_5$ integrin antagonists are depicted in Table 1 below along with their corresponding plasma level upon oral dosing (AUC-PO) level.

ns
TABLE 1

| Structure | Rat AUC/Dose (ug-/mL/mg/Kg) |
|---|---|
| (structure) | 6.81 |
| (structure) | 0.0634 |
| (structure) | |
| (structure) | |
| (structure) | |
| (structure) | |

TABLE 1-continued
| Structure | Rat AUC/Dose (ug-/m/L/mg/Kg) |
|---|---|
| 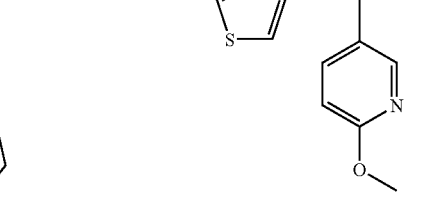 | |
| 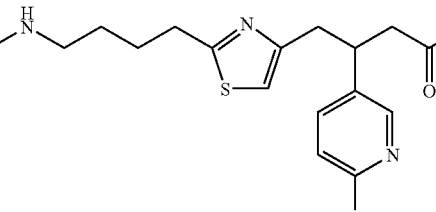 | |
| Structure | Name | Rat PK-AUC/dose (ug-h/m/L/mg/Kg) |
|---|---|---|
| 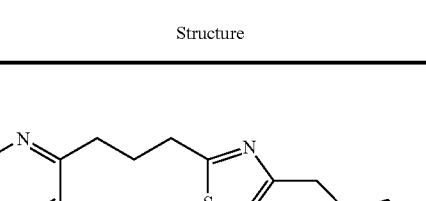 | 3-(1,3-benzodioxol-5-yl)4{2-[3-(5,6,7,8-tetrahydro-1,8-naphthyridin-2-yl)propyl]-1,3-thiazol-4-yl}butanoic acid | 6.8 |
| 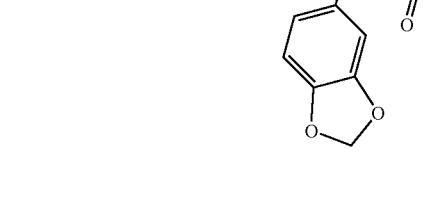 | 3-(3,5-dimethoxyphenyl)-4-{2-[3-(5,6,7,8-tetrahydro-1,8-naphthyridin-2-yl)propyl]-1,3-thiazol-4-yl}butanoic acid | 2.2 |

-continued

| Structure | Name | Rat PK-AUC/dose (ug-h/m/L/mg/Kg) |
|---|---|---|
| 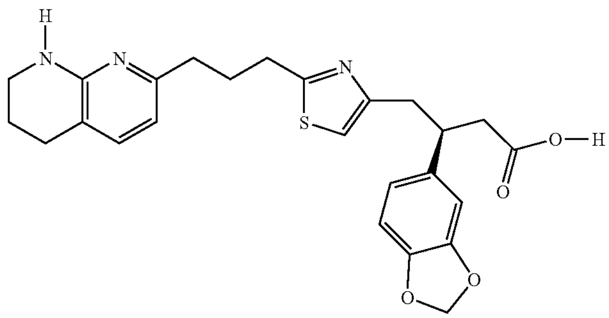 | (3S)-3-(1,3-benzodioxol-5-yl)-4-{2-[3-(5,6,7,8-tetrahydro-1,8-naphthyridin-2-yl)propyl]-1,3-thiazol-4-yl}butanoic acid | 8.7 |
| 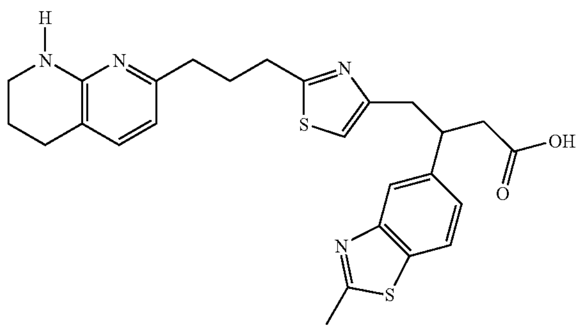 | 3-(2-methyl-1,3-benzothiazol-5-yl)-4-{2-[3-(5,6,7,8-tetrahydro-1,8-naphthyridin-2-yl)propyl]-1,3-thiazol-4-yl}butanoic acid | 2.5 |
| 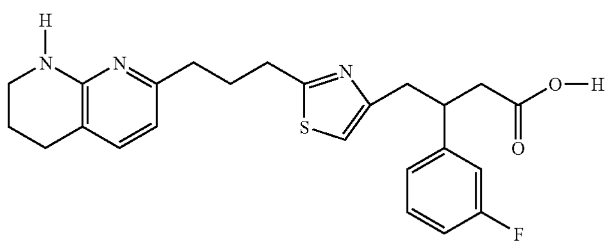 | 3-(3-fluorophenyl)-4-{2-[3-(5,6,7,8-tetrahydro-1,8-naphthyridin-2-yl)propyl]-1,3-thiazol-4-yl}butanoic acid | |
| 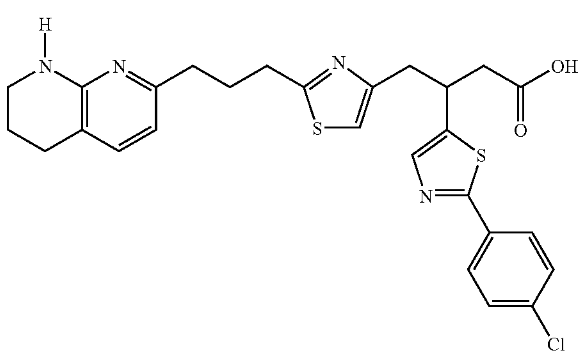 | 3-[2-(4-chlorophenyl)-1,3-thiazol-5-yl]-4-{2-[3-(5,6,7,8-tetrahydro-1,8-naphthyridin-2-yl)propyl]-1,3-thiazol-4-yl}butanoic acid | |
| 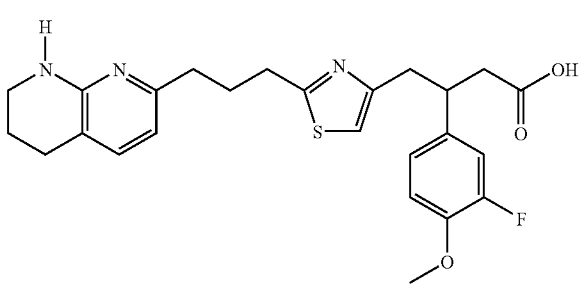 | 3-(3-fluoro-4-methoxyphenyl)-4-{2-[3-(5,6,7,8-tetrahydro-1,8-naphthyridin-2-yl)propyl]-1,3-thiazol-4-yl}butanoic acid | 1.8 |

| Structure | Name | Rat PK-AUC/dose (ug-h/m/L/mg/Kg) |
|---|---|---|
| 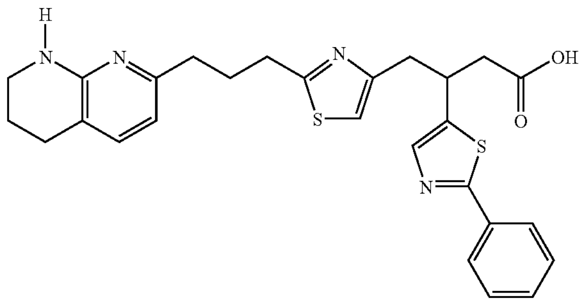 | 3-(2-phenyl-1,3-thiazol-5-yl)-4-{2-[3-(5,6,7,8-tetrahydro-1,8-naphthyridin-2-yl)propyl]-1,3-thiazol-4-yl}butanoic acid | |
| 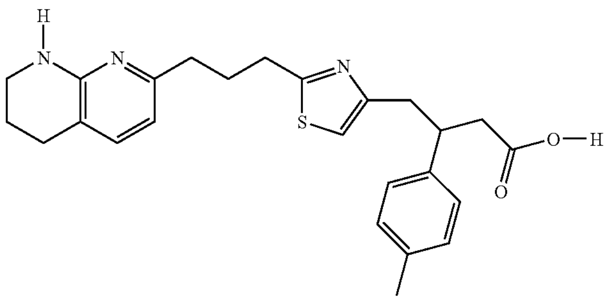 | 3-(4-methylphenyl)-4-{2-[3-(5,6,7,8-tetrahydro-1,8-naphthyridin-2-yl)propyl]-1,3-thiazol-4-yl}butanoic acid | |
| 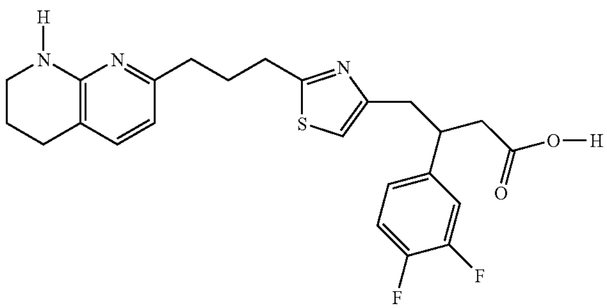 | 3-(3,4-difluorophenyl)-4-{2-[3-(5,6,7,8-tetrahydro-1,8-naphthyridin-2-yl)propyl]-1,3-thiazol-4-yl}butanoic acid | |
| 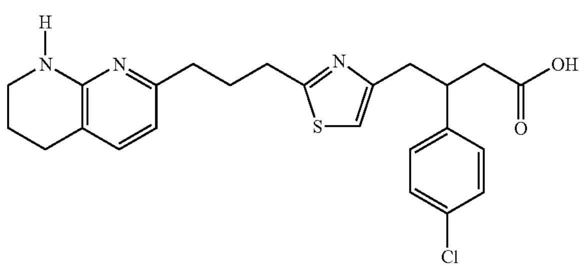 | 3-(4-chlorophenyl)-4-{2-[3-(5,6,7,8-tetrahydro-1,8-naphthyridin-2-yl)propyl]-1,3-thiazol-4-yl}butanoic acid | |
| 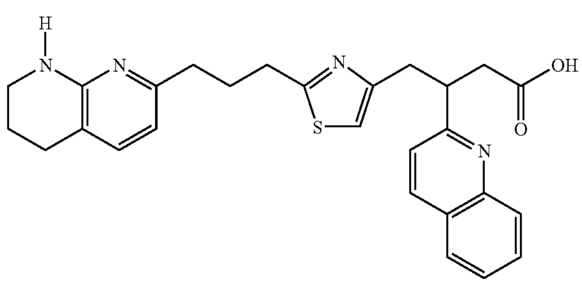 | 3-quinolin-2-yl-4-{2-[3-(5,6,7,8-tetrahydro-1,8-naphthyridin-2-yl)propyl]-1,3-thiazol-4-yl}butanoic acid | |

-continued

| Structure | Name | Rat PK-AUC/dose (ug-h/m/L/mg/Kg) |
|---|---|---|
| 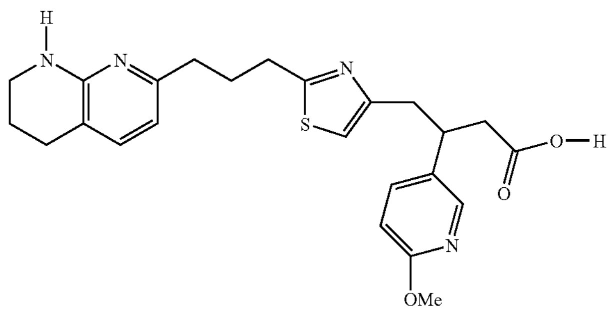 | 3-(6-methoxypyridin-3-yl)-4-{2-[3-(5,6,7,8-tetrahydro-1,8-naphthyridin-2-yl)propyl]-1,3-thiazol-4-yl}butanoic acid | 1.6 |
| 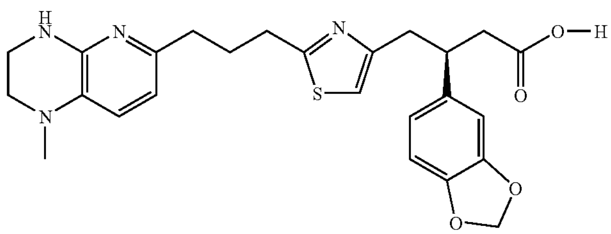 | (3S)-3-(1,3-benzodioxol-5-yl)-4-{2-[3-(1-methyl-1,2,3,4-tetrahydropyrido[2,3-b]pyrazin-6-yl)propyl]-1,3-thiazol-4-yl}butanoic acid | |
| 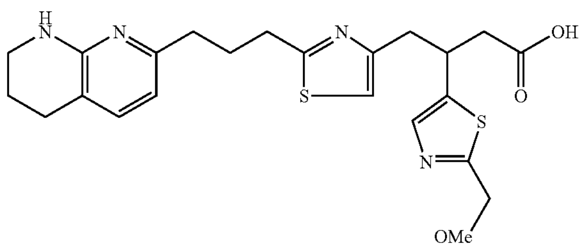 | 3-[2-(methoxymethyl)-1,3-thiazol-5-yl]-4-{2-[3-(5,6,7,8-tetrahydro-1,8-naphthyridin-2-yl)propyl]-1,3-thiazol-4-yl}butanoic acid | |
| 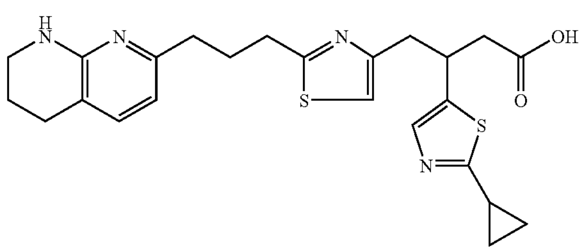 | 3-(2-cyclopropyl-1,3-thiazol-5-yl)-4-{2-[3-(5,6,7,8-tetrahydro-1,8-naphthyridin-2-yl)propyl]-1,3-thiazol-4-yl}butanoic acid | 1.7 |
| 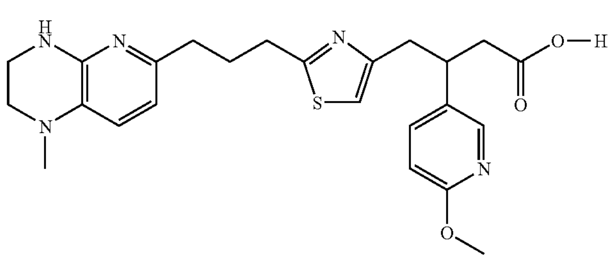 | 3-(6-methoxypyridin-3-yl)-4-{2-[3-(1-methyl-1,2,3,4-tetrahydropyrido[2,3-b]pyrazin-6-yl)propyl]-1,3-thiazol-4-yl}butanoic acid | |

-continued

| Structure | Name | Rat PK-AUC/dose (ug-h/m/L/mg/Kg) |
|---|---|---|
| 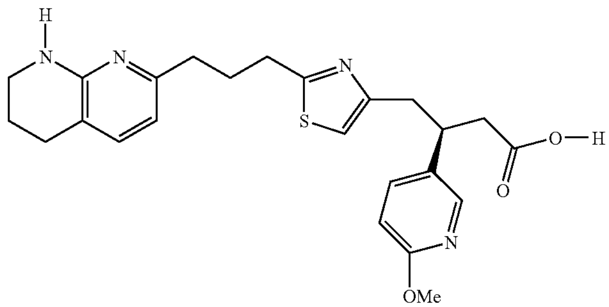 | (3S)-3-(6-methoxypyridin-3-yl)-4-{2-[3-(5,6,7,8-tetrahydro-1,8-naphthyridin-2-yl)propyl]-1,3-thiazol-4-yl}butanoic acid | |
| 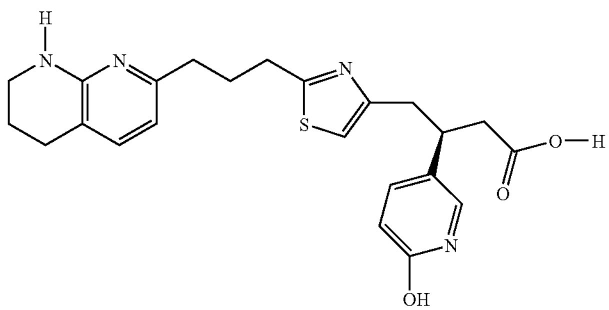 | (3S)-3-(6-hydroxypyridin-3-yl)-4-{2-[3-(5,6,7,8-tetrahydro-1,8-naphthyridin-2-yl)propyl]-1,3-thiazol-4-yl}butanoic acid | |
| 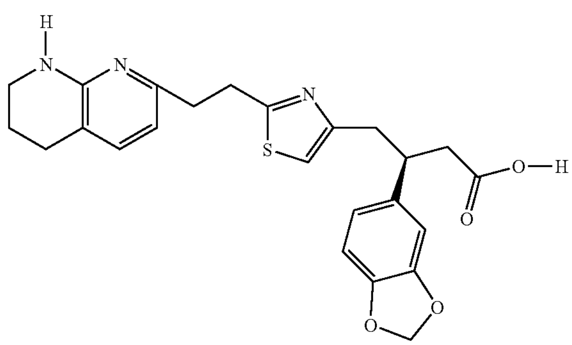 | (3S)-3-(1,3-benzodioxol-5-yl)-4-{2-[2-(5,6,7,8-tetrahydro-1,8-naphthyridin-2-yl)ethyl]-1,3-thiazol-4-yl}butanoic acid | |

What is claimed is:

1. A compound corresponding to Formula I:

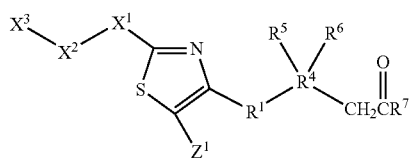

(I)

or a pharmaceutically acceptable salt thereof, wherein:

$R^1$ is selected from the group consisting of —CH($R^2$)—, —N($R^3$)—, —O—, —S—, —S(O)$_2$—, and —C(O)—;

$Z^1$ is selected from the group consisting of hydrogen, heteroaryl, and optionally substituted alkyl or aryl, wherein the substituent is selected from the group consisting of alkyl, halogen, hydroxy, alkoxy, amino, alkylamino, dialkylamino, cyano, acyl, —S—, —SO—, —SO$_2$—, sulfonamido, aryl, and heteroaryl;

$X^1$ is a carbon chain of 1 to 3 carbon atoms with or without a carbon-carbon unsaturated bond; $X^1$ is selected from the group consisting of —O—, —S—, —SO—, —SO$_2$—, —N—, and —CH$_2$—;

$R^2$ is H, hydroxy, or alkoxy;

$R^3$ is selected from the group consisting of hydrogen, heteroaryl, optionally substituted alkyl or aryl, wherein the substituent is selected from the group consisting of alkyl, halogen, hydroxy, alkoxy, amino, alkylamino, dialkylamino, cyano, acyl, —S—, —SO—, —SO$_2$, sulfonamido, aryl, and heteroaryl;

$R^4$ is carbon or nitrogen;

$R^5$ is selected from the group consisting of hydrogen, heteroaryl, and optionally substituted alkyl or aryl, wherein the substituent is selected from the group consisting of alkyl, halogen, hydroxy, alkoxy, amino, alkylamino, dialkylamino, cyano, acyl, —S—, —SO—, —SO$_2$, sulfonamido, aryl, and heteroaryl;

$R^6$ is selected from the group consisting of hydrogen, heteroaryl, an electron pair, and optionally substituted alkyl or aryl, wherein the substituent is selected from the group consisting of alkyl, halogen, hydroxy, alkoxy, amino, alkylamino, dialkylamino, cyano, acyl, —S—, —SO—, —SO$_2$, sulfonamido, aryl, and heteroaryl;

R$^7$ is hydroxy or alkoxy;

X$^3$ is selected from the group consisting of:

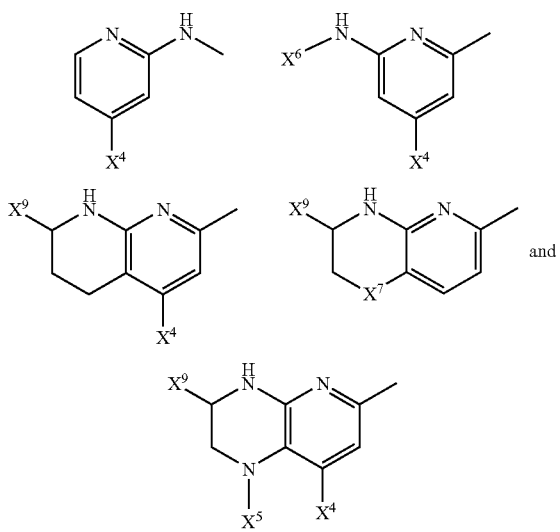

wherein:
- X$^4$ is selected from the group consisting of hydrogen, hydroxy, alkoxy, amino, alkylamino, dialkylamino, cyclicamino, heterocyclo, —N—SO$_2$R$^x$ wherein R$^x$ is alkyl or aryl, and optionally substituted hydrocarbyl, wherein the substituent is selected from the group consisting of alkyl, halogen, hydroxy, alkoxy, amino, alkylamino, dialkylamino, cyano, acyl, —S—, —SO—, —SO$_2$—, sulfonamido, aryl, and heteroaryl;
- X$^5$, X$^6$, and X$^8$ are independently selected from the group consisting of hydrogen, heterocyclo, and optionally substituted hydrocarbyl, wherein the substituent is selected from the group consisting of alkyl, halogen, hydroxy, alkoxy, amino, alkylamino, dialkylamino, cyano, acyl, —S—, —SO—, —SO$_2$—, sulfonamido, aryl, and heteroaryl;
- X$^7$ is selected from the group consisting of —CH$_2$, —CH$_2$O—, —OCH$_2$—, —S—, —SO—, —SO$_2$—, —O—, —C(O)—, —CH(OH)—, —NH—, and —NX$^8$; and
- X$^9$ is =O or —OH.

2. A compound corresponding to Formula II:

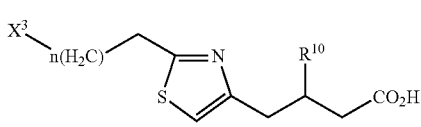

or a pharmaceutically acceptable salt thereof, wherein:
- n is 1–3;
- R$^{10}$ is selected from the group consisting of aryl, aralkyl, heteroaralkyl, and heteroaryl;

X$^3$ is selected from the group consisting of:

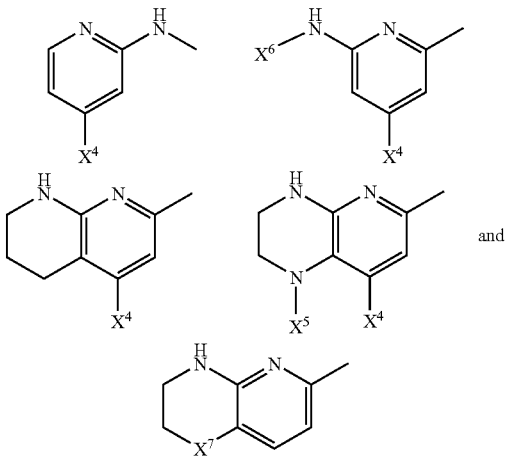

X$^4$ is hydrogen, hydroxy, alkoxy, amino, heterocyclo, and optionally substituted hydrocarbyl, wherein the substituent is selected from the group consisting of alkyl, halogen, hydroxy, alkoxy, amino, alkylamino, dialkylamino, cyano, acyl, —S—, —SO—, —SO$_2$—, sulfonamido, aryl, and heteroaryl;

X$^5$, X$^6$, and X$^8$ are independently hydrogen, heterocyclo, or optionally substituted hydrocarbyl, wherein the substituent is selected from the group consisting of alkyl, halogen, hydroxy, alkoxy, amino, alkylamino, dialkylamino, cyano, acyl, —S—, —SO—, —SO$_2$—, sulfonamido, aryl, and heteroaryl; and X$^7$ is —CH$_2$, —CH$_2$O—, —OCH$_2$—, —S—, —O—, —C(O)—, —CH(OH)—, —NH—, or —NX$^8$.

3. The compound of claim 2 wherein R$^{10}$ is optionally substituted by one or more substituents selected from the group consisting of alkyl, haloalkyl, aryl, heteroaryl, halogen, alkoxyalkyl, aminoalkyl, hydroxy, nitro, alkoxy, hydroxyalkyl, thioalkyl, amino, alkylamino, arylamino, alkylsulfonamide, acyl, acylamino, alkylsulfone, sulfonamide, allyl, alkenyl, methylenedioxy, ethylenedioxy, alkynyl, carboxamide, cyano, and —(CH$_2$)$_m$COR wherein m is 0–2 and R is hydroxy, alkoxy, alkyl and amino.

4. The compound of claim 2 wherein the compound is the "S" isomer.

5. The compound of claim 1 or 2 wherein the compound or a pharmaceutically acceptable salt thereof is selected from the group consisting of:

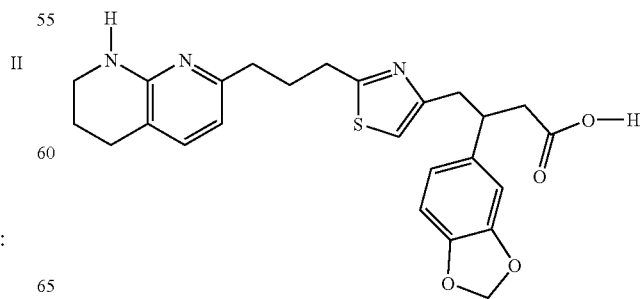

a) 3-(1,3-benzodioxol-5-yl)-4-{2-[3-(5,6,7,8-tetrahydro-1,8-naphthyridin-2-yl)propyl]-1,3-thiazol-4-yl}butanoic acid d) 3-(2-methyl-1,3-benzothiazol-5-yl)-4-{2-[3-(5,6,7,8-tetrahydro-1,8-naphthyridin-2-yl)propyl]-1,3-thiazol-4-yl}butanoic acid

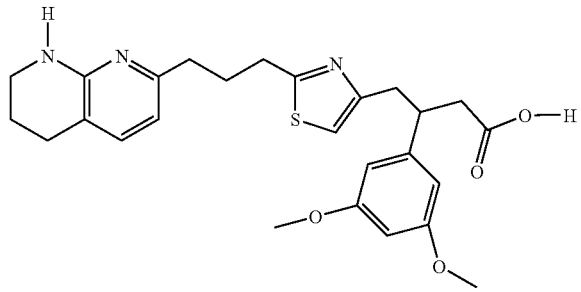

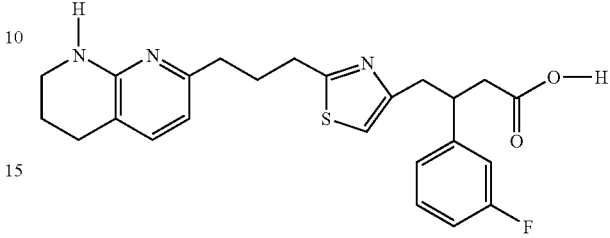

b) 3-(3,5-dimethoxyphenyl)-4-{2-[3-(5,6,7,8-tetrahydro-1,8-naphthyridin-2-yl)propyl]-1,3-thiazol-4-yl}butanoic acid e) 3-(3-fluorophenyl)-4-{2-[3-(5,6,7,8-tetrahydro-1,8-naphthyridin-2-yl)propyl]-1,3-thiazol-4-yl}butanoic acid

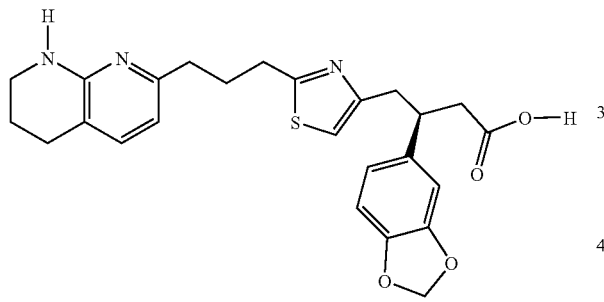

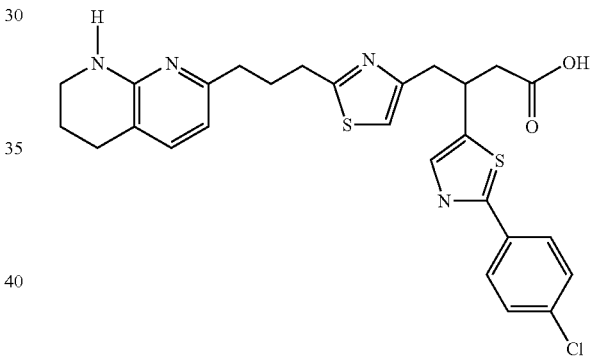

c) (3S)-3-(1,3-benzodioxol-5-yl)-4-{2-[3-(5,6,7,8-tetrahydro-1,8-naphthyridin-2-yl)propyl]-1,3-thiazol-4-yl}butanoic acid f) 3-[2-(4-chlorophenyl)-1,3-thiazol-5-yl]-4-{2-[3-(5,6,7,8-tetrahydro-1,8-naphthyridin-2-yl)propyl]-1,3-thiazol-4-yl}butanoic acid

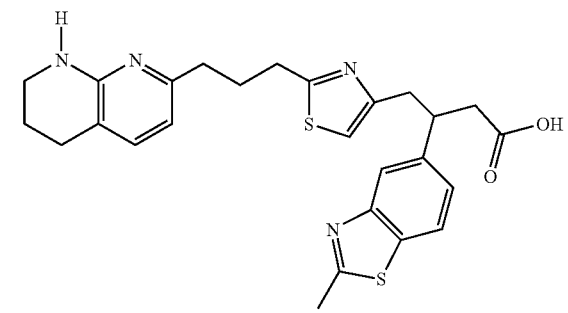

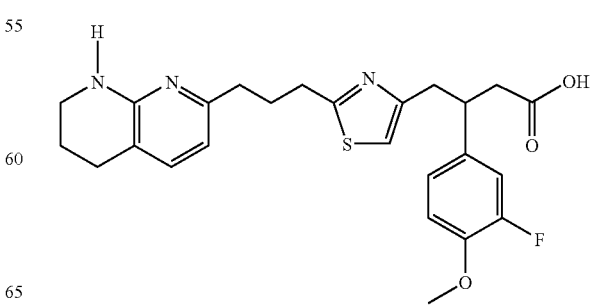

g) 3-(3-fluoro-4-methoxyphenyl)-4-{2-[3-(5,6,7,8-tetrahydro-1,8-naphthyridin-2-yl)propyl]-1,3-thiazol-4-yl}butanoic acid

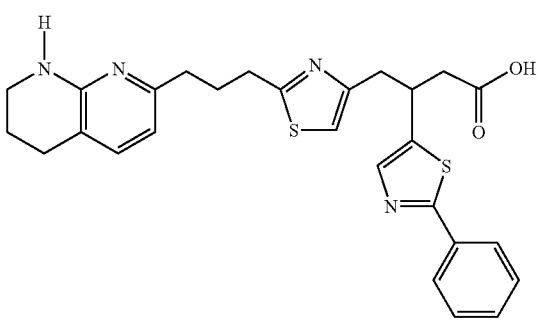

h) 3-(2-phenyl-1,3-thiazol-5-yl)-4-{2-[3-(5,6,7,8-tetrahydro-1,8-naphthyridin-2-yl)propyl]-1,3-thiazol-4-yl}butanoic acid

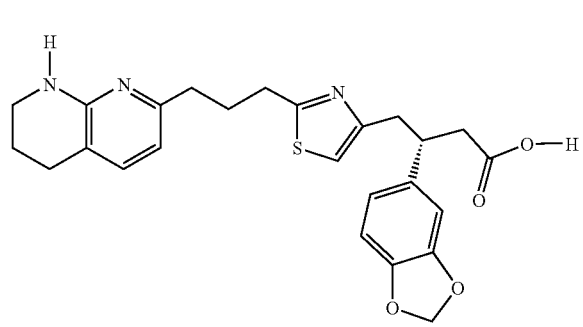

i) (3R)-3-(1,3-benzodioxol-5-yl)-4-{2-[3-(5,6,7,8-tetrahydro-1,8-naphthyridin-2-yl)propyl]-1,3-thiazol-4-yl}butanoic acid

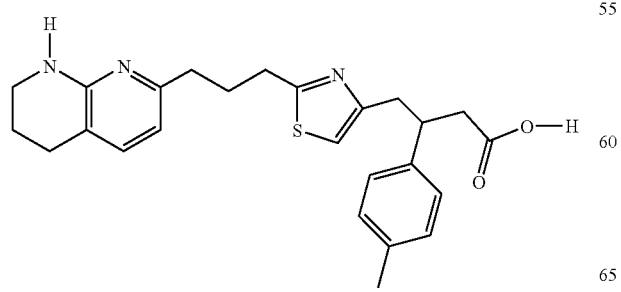

j) 3-(4-methylphenyl)-4-{2-[3-(5,6,7,8-tetrahydro-1,8-naphthyridin-2-yl)propyl]-1,3-thiazol-4-yl}butanoic acid

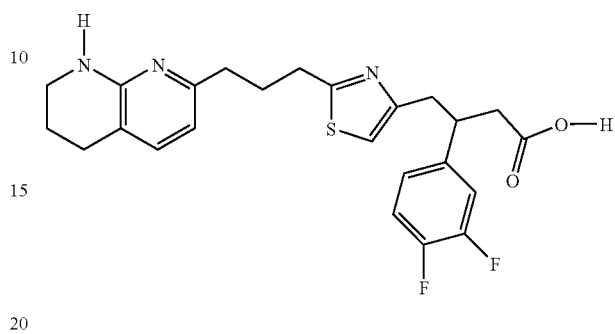

k) 3-(3,4-difluorophenyl)-4-{2-[3-(5,6,7,8-tetrahydro-1,8-naphthyridin-2-yl)propyl]-1,3-thiazol-4-yl}butanoic acid

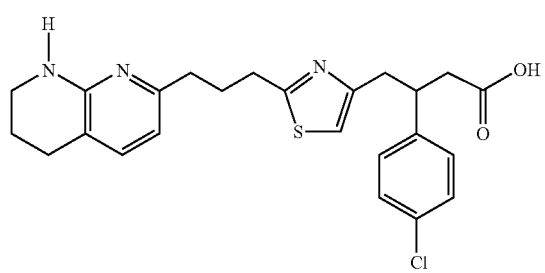

l) 3-(4-chlorophenyl)-4-{2-[3-(5,6,7,8-tetrahydro-1,8-naphthyridin-2-yl)propyl]-1,3-thiazol-4-yl}butanoic acid

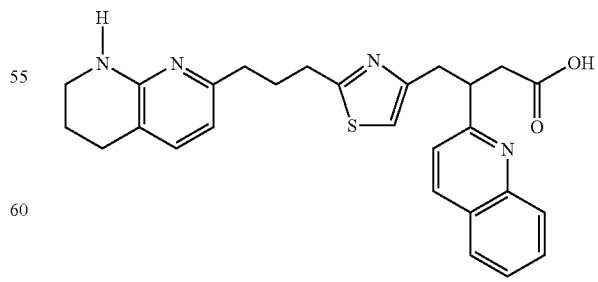

m) 3-quinolin-2-yl-4-{2-[3-(5,6,7,8-tetrahydro-1,8-naphthyridin-2-yl)propyl]-1,3-thiazol-4-yl}butanoic acid

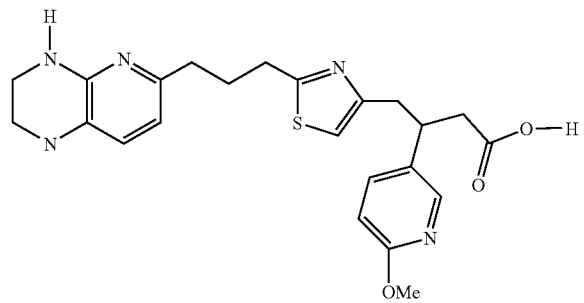

n) 3-(6-methoxypyridin-3-yl)-4-{2-[3-(5,6,7,8-tetrahydro-1,8-naphthyridin-2-yl)propyl]-1,3-thiazol-4-yl}butanoic acid

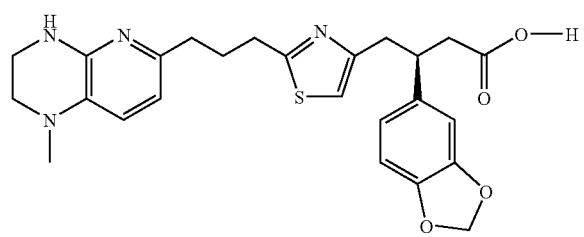

o) (3S)-3-(1,3-benzodioxol-5-yl)-4-{2-[3-(1-methyl-1,2,3,4-tetrahydropyrido[2,3-b]pyrazin-6-yl)propyl]-1,3-thiazol-4-yl}butanoic acid p) (3S)-3-(1,3-benzodioxol-5-yl)-4-(2-{4-[(4-morpholin-4-ylpyridin-2-yl)amino]butyl}-1,3-thiazol-4-yl)butanoic acid

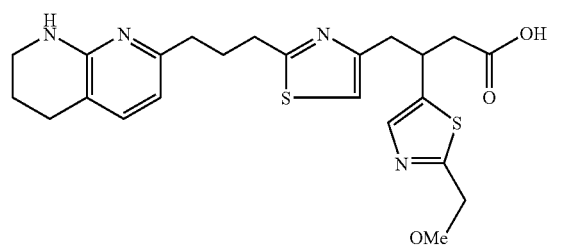

q) 3-[2-(methoxymethyl)-1,3-thiazol-5-yl]-4-{2-[3-(5,6,7,8-tetrahydro-1,8-naphthyridin-2-yl)propyl]-1,3-thiazol-4-yl}butanoic acid

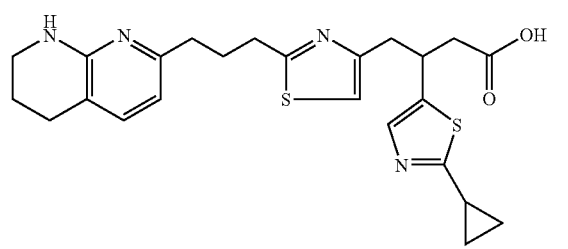

r) 3-(2-cyclopropyl-1,3-thiazol-5-yl)-4-{2-[3-(5,6,7,8-tetrahydro-1,8-naphthyridin-2-yl)propyl]-1,3-thiazol-4-yl}butanoic acid

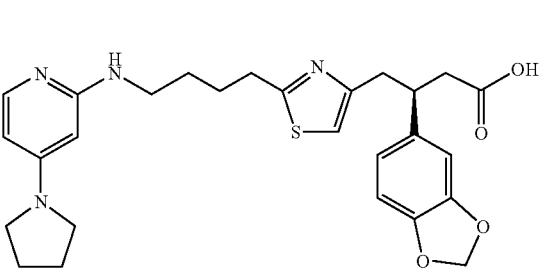

s) (3S)-3-(1,3-benzodioxol-5-yl)-4-(2-{4-[(4-pyrrolidin-1-ylpyridin-2-yl)amino]butyl}-1,3-thiazol-4-yl)butanoic acid

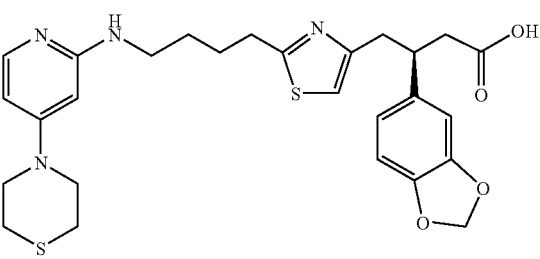

t) (3S)-3-(1,3-benzodioxol-5-yl)-4-(2-{4-[(4-thiomorpholin-4-ylpyridin-2-yl)amino]butyl}-1,3-thiazol-4-yl)butanoic acid

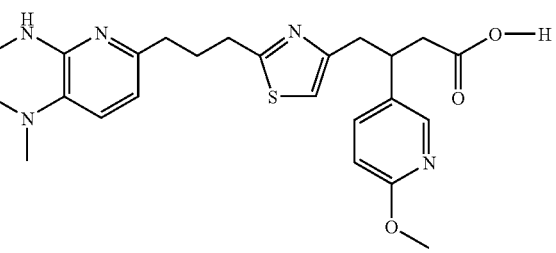

u) 3-(6-methoxypyridin-3-yl)-4-{2-[3-(1-methyl-1,2,3,4-tetrahydropyrido[2,3-b]pyrazin-6-yl)propyl]-1,3-thiazol-4-yl}butanoic acid

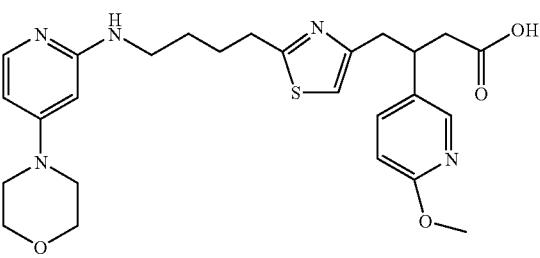

v) 3-(6-methoxypyridin-3-yl)-4-(2-{4-[(4-morpholin-4-ylpyridin-2-yl)amino]butyl}-1,3-thiazol-4-yl)butanoic acid

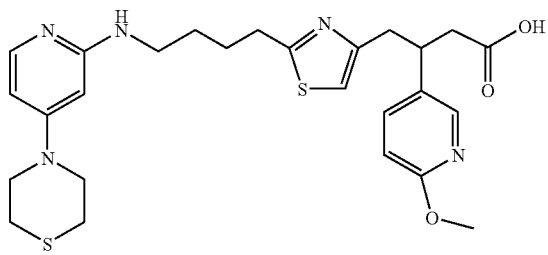

w) 3-(6-methoxypyridin-3-yl)-4-(2-{4-[(4-thiomorpholin-4-ylpyridin-2-yl)amino]butyl}-1 3-thiazol-4-yl)butanoic acid

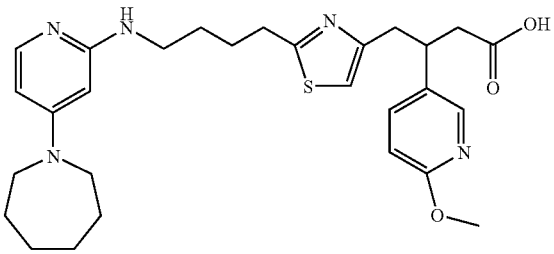

x) 4-(2-{4-[(4-azepan-1-ylpyridin-2-yl)amino]butyl}-1,3-thiazol-4-yl )-3-(6-methoxypyridin-3-yl)butanoic acid

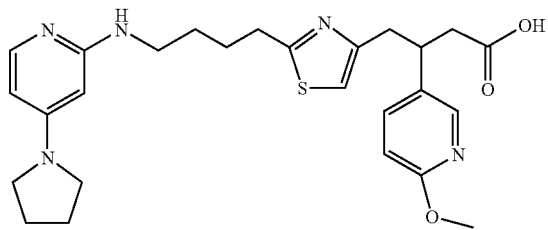

y) 3-(6-methoxypyridin-3-yl)-4-(2-{4-[(4-pyrrolidin-1-ylpyridin-2-yl)amino]butyl}-1,3-thiazol-4-yl)butanoic acid

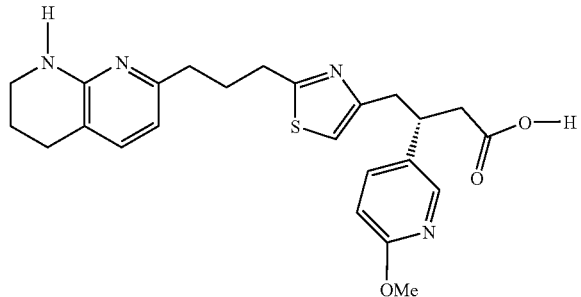

z) (3R)-3-(6-methoxypyridin-3-yl)-4-{2-[3-(5,6,7,8-tetrahydro-1,8-naphthyridin-2-yl)propyl]-1,3-thiazol-4-yl}butanoic acid

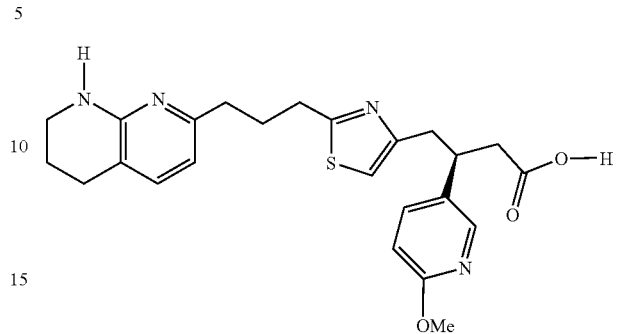

aa) (3R)-3-(6-methoxypyridin-3-yl)-4-{2-[3-(5,6,7,8-tetrahydro-1,8-naphthyridin-2-yl)propyl]-1,3-thiazol-4-yl}butanoic acid

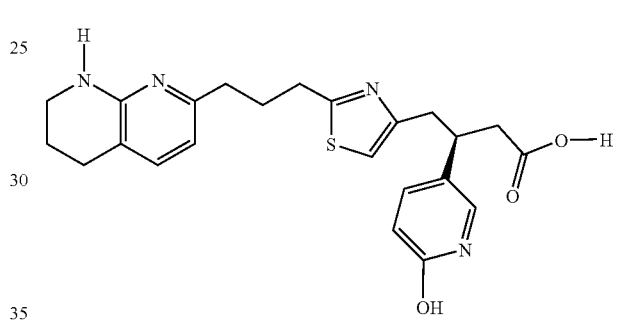

bb) (3S)-3-(6-hydroxypyridin-3-yl)-4-{2-[3-(5,6,7,8-tetrahydro-1,8-naphthyridin-2-yl)propyl]-1,3-thiazol-4-yl}butanoic acid

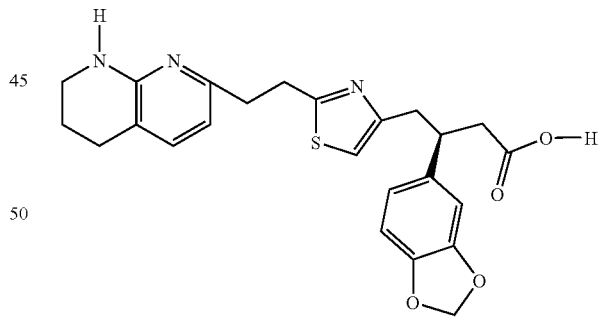

cc) (3S)-3-(1,3-benzodioxol-5-yl)-4-{2-[2-(5,6,7,8-tetrahydro-1,8-naphthyridin-2-yl)ethyl]-1,3-thiazol-4-yl}butanoic acid.

6. A pharmaceutical composition comprising a therapeutically effective amount of a compound of claim 1 or 2 and a pharmaceutically acceptable carrier.

* * * * *